US012761203B2

(12) United States Patent
Karydis et al.

(10) Patent No.: US 12,761,203 B2
(45) Date of Patent: Oct. 13, 2026

(54) PORTABLE AGRICULTURAL ROBOT FOR CONTINUOUS APPARENT SOIL ELECTRICAL CONDUCTIVITY MEASUREMENTS TO IMPROVE IRRIGATION PRACTICES

(71) Applicant: The Regents of the University of California, Oakland, CA (US)

(72) Inventors: Konstantinos Karydis, Laguna Beach, CA (US); Elia Scudiero, Riverside, CA (US); Merrick Campbell, Riverside, CA (US); Dimitrios Chatziparaschis, Riverside, CA (US); Keran Ye, Riverside, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 441 days.

(21) Appl. No.: 18/203,517

(22) Filed: May 30, 2023

(65) Prior Publication Data

US 2023/0400446 A1 Dec. 14, 2023

Related U.S. Application Data

(60) Provisional application No. 63/346,676, filed on May 27, 2022.

(51) Int. Cl.

| | |
|---|---|
| ***G01N 33/24*** | (2006.01) |
| ***A01B 69/04*** | (2006.01) |

(Continued)

(52) U.S. Cl.

CPC ......... *G01N 33/246* (2013.01); *A01B 69/008* (2013.01); *A01G 25/167* (2013.01); (Continued)

(58) Field of Classification Search

CPC .. G01N 33/246; G01N 33/245; A01B 69/008; A01B 79/005; A01G 25/167; (Continued)

(56) References Cited

U.S. PATENT DOCUMENTS

| | | | | |
|---|---|---|---|---|
| 11,035,838 | B2 | 6/2021 | Willness | |
| 2018/0356389 | A1* | 12/2018 | Willness .................. | G01C 9/06 |

(Continued)

OTHER PUBLICATIONS

Campbell et al. ("A Portable Agricultural Robot for Continuous Apparent Soil Electrical Conductivity Measurements to Improve Irrigation Practices," 2021 IEEE 17th International Conference on Automation Science and Engineering (CASE), Lyon, France, 2021, pp. 2228-2234,) (Year: 2021).*

(Continued)

*Primary Examiner* — Christian T Bryant

(74) *Attorney, Agent, or Firm* — Viksnins Harris Padys Malen LLP

(57) ABSTRACT

Apparatus and methods for determining soil moisture. An apparatus includes a mobile platform to traverse an agricultural field, a sensor physically coupled to the mobile platform, the sensor to make one or more soil apparent electrical conductivity measurements, and a control system mounted on the chassis and communicatively coupled to the sensor. A method includes navigating an agricultural field with a mobile platform, generating a real-time position and orientation for the mobile platform, performing one or more soil apparent electrical conductivity measurements from a sensor physically coupled to the mobile platform, synchronizing the one or more soil apparent electrical conductivity measurements with the real-time position, geospatial mapping and autonomously logging the one or more soil apparent electrical conductivity measurements, and processing each of the one or more soil apparent electrical conductivity measurements to generate a soil moisture value.

14 Claims, 38 Drawing Sheets

(51) Int. Cl.

| | |
|---|---|
| ***A01B 79/00*** | (2006.01) |
| ***A01G 25/16*** | (2006.01) |
| ***G05D 1/00*** | (2024.01) |
| ***G05D 1/245*** | (2024.01) |
| ***G05D 1/248*** | (2024.01) |
| ***G05D 1/648*** | (2024.01) |
| ***G05D 105/80*** | (2024.01) |
| ***G05D 107/20*** | (2024.01) |
| ***G05D 109/10*** | (2024.01) |
| ***G05D 111/50*** | (2024.01) |
| ***G05D 111/67*** | (2024.01) |

(52) U.S. Cl.

CPC .......... *G05D 1/0088* (2013.01); *A01B 79/005* (2013.01); *G01N 33/245* (2024.05); *G05D 1/245* (2024.01); *G05D 1/248* (2024.01); *G05D 1/648* (2024.01); *G05D 2105/87* (2024.01); *G05D 2107/21* (2024.01); *G05D 2109/10* (2024.01); *G05D 2111/54* (2024.01); *G05D 2111/67* (2024.01)

(58) Field of Classification Search

CPC .. G05D 1/0088; G05D 1/245; G05D 2111/54; G05D 2111/67; G05D 1/248; G05D 1/648; G05D 2105/87; G05D 2107/21; G05D 2119/10; G05D 2109/10

See application file for complete search history.

(56) References Cited

U.S. PATENT DOCUMENTS

| | | | | |
|---|---|---|---|---|
| 2021/0103728 | A1* | 4/2021 | Young | G06V 20/56 |
| 2021/0259149 | A1* | 8/2021 | Zemenchik | A01B 79/005 |
| 2022/0111960 | A1* | 4/2022 | Tran | B64D 1/18 |
| 2022/0142039 | A1* | 5/2022 | Eichhorn | A01B 63/111 |

OTHER PUBLICATIONS

Barawid, O. , et al., "Development of an autonomous navigation system using a two-dimensional laser scanner in an orchard application", Biosystems Engineering 96(2), 139-149 (2007).

Beaudette, D. , et al., "Soil-web: An online soil survey for California, Arizona, and Nevada", Computers & Geosciences 35(10), 2119-2128 (2009).

Calamita, G. , et al., "Field test of a multi-frequency electromagnetic induction sensor for soil moisture monitoring in southern italy test sites", Journal of Hydrology 529, 316-329 (2015).

Cordoba, M. , et al., "Protocol for multivariate homogeneous zone delineation in precision agriculture", Biosystems Engineering 143, 95-107 (2016).

Corwin, D. , et al., "Field-scale apparent soil electrical conductivity", Soil Science Society of America Journal 84(5), 1405-1441 (2020).

De Leeuw, W. , et al., "A multi rosbot laboratory setup for experimenting autonomous driving maneuvers", 2020 28th Mediterranean Conference on Control and Automation (MED) IEEE, 532-537 (2020).

Endres, F. , et al., "3-d mapping with an rgb-d camera", IEEE Transactions on Robotics 30(1), 11 pages (2012).

Fentanes, J. , et al., "Kriging-based robotic exploration for soil moisture mapping using a cosmic-ray sensor", Journals of Fields Robotics 37(1), 122-136 (2020).

Hiremath, S. , et al., "Laser range finder model for autonomous navigation of a robot in a maize field using a particle filter", Computers and Electronics in Agriculture 100, 41-50 (2014).

Huang, J. , et al., "Time-lapse monitoring of soil water content using electromagnetic conductivity imaging", Soil Use and Management 33(2), 191-204 (2016).

Huang, A. , et al., "Visual odometry and mapping for autonomous flight using an rgb-d camera", Robotics Research, 235-252 (2017).

Julier, S. , et al., "New extension of the kalman filter to nonlinear systems", Signal Processing Sensor Fusion, and Target Recognition VI 3068, International Society for Optics and Photonics, 182-193 (1997).

Lesch, S. , et al., "Apparent soil electrical conductivity mapping as an agricultural management tool in arid zone soils", Computers and Electronics in Agriculture 46, 351-378 (2005).

Malavazi, F. B. , et al., "Lidar-only based navigation algorithm for an autonomous agricultural robot", Computers and Electronics in Agriculture 154, 71-79 (2018).

Nielsen, D. , et al., "Spatial variability of field-measured soil-water properties", Hilgardia 42, 215-259 (1973).

Perdue, S. , "2018 Irrigation and Water Management Survey", Census of Agriculture 3, 269 pages, 2017, Issued Nov. 2019.

Philips, A. , et al., "Integrated sensing of soil moisture at the field-scale: Measuring, modeling and sharing for improved agricultural decision support", Computers and Electronics 107, 73-88 (2014).

Ruckelshausen, A. , et al., "BoniRob: an autonomous field robot platform for individual plant phenotyping", Precision Agriculture 9, 841-847 (2009).

Senthil, P. , et al., "Automated robotic moisture monitoring in agricultural fields", International Seminar on Intelligent Technology and Its Applications (ISITLA), 375-380 (2018).

Skaggs, T. , et al., "Comparison of hydrus-2d simulations of drip irrigation with experimental observations", Journal of Irrigation and Drainage Engineering 130, 304-310 (2004).

Skaggs, T. , et al., "Drip irrigation water distribution patterns: Effects of emitter rate, pulsing, and antecedent water", Soil Science of Society of America Journal 74(6), 1886-1896 (2010).

Sudduth, K. , et al., "Accuracy issues in electromagnetic induction sensing of soil electrical conductivity for precision agriculture", Computers and Electronics in Agriculture 31, 239-264 (2001).

Topp, G. , et al., "Electromagnetic determination of soil water content: Measurements in coaxial transmission lines", Water Resource Research 16(3), 574-582 (1980).

Vellidis, G. , et al., "A dynamic variable rate irrigation control system", Proceedings of the 13th International Conference on Precision Agriculture, St. Louis, Missouri, vol. 31, 9 pages (2016).

Vellidis, G. , et al., "Development and assessment of a smartphone application for irrigation scheduling in cotton", Computers and Electronics in Agriculture 127, 249-259 (2016).

Wellington, C. , et al., "A generative model of terrain for autonomous navigation in vegetation", The International Journal of Robotics Research 25(12), 1287-1304 (2006).

Zhang, N. , et al., "Precision agriculture—a world-wide overview", Computers and Electronics in Argiculture 36(2), 113-132 (2002).

* cited by examiner

PORTABLE AGRICULTURAL ROBOT FOR CONTINUOUS APPARENT SOIL ELECTRICAL CONDUCTIVITY MEASUREMENTS TO IMPROVE IRRIGATION PRACTICES

CROSS-REFERENCE TO RELATED APPLICATION

This application claims priority to U.S. Provisional Application No. 63/346,676, filed on May 27, 2022. The entire content of the application referenced above is hereby incorporated by reference herein.

STATEMENT REGARDING FEDERALLY SPONSORED RESEARCH

This invention was made with government support under 2021-67022-33453 awarded by National Institute of Food and Agriculture, USDA. The government has certain rights in the invention.

FIELD

The present disclosure generally relates to agricultural apparatus and methods. More particularly, and without limitation, the present disclosure relates to a mobile platform and methods for determining soil moisture.

BACKGROUND

Precision agriculture is an increasingly adopted farming practice that aims to administer agronomic inputs (e.g., irrigation, fertilizers, pesticides) when, where, and in the amount needed. To inform such management, networks of ground and remote sensors are used to accurately characterize soil-plant-environment processes. Precision irrigation, specifically, can increase grower revenue and decrease the environmental footprint of agriculture by applying water directly where and when required from the ideal source. Accurate estimates of water available to plant roots throughout the soil profile can be obtained with soil sensors. However, only 12% of growers in the USA use root-zone soil measurements to trigger and budget irrigation events. The growers that utilize these measurements rely on an expensive network of decentralized sensors. These sensors generally measure only a few points across large swathes of land and provide an incomplete picture of irrigation practices. Such lean sampling fails to capture soil spatial variability, which is a key component of plant-water-environment relationships. Knowledge of soil moisture (SM) spatial variability can improve precision irrigation.

Capturing continuous measurements with a robotic system helps remove several current barriers to entry that prevent the wider adoption of soil moisture measurements. Geospatial electromagnetic induction (EMI) measurements of soil apparent electrical conductivity (ECa) are a reliable proxy for SM spatial variability. Barriers to the use of this technology include the cost of carrying out reliable EMI surveys and calibrating the sensor readings to SM estimations. Concurrent in-situ measurements of soil moisture can calibrate field-scale ECa geospatial surveys to accurately map root-zone soil moisture using physically-based stochastic modeling. Then site-specific ECa-to-SM calibrations are elaborated by experts using concurrent SM data from in-situ SM monitoring stations or from soil cores.

However, integrating an EMI soil sensor with a robotic platform presents several challenges. The EMI sensors use a paired emitter to induce a magnetic field in the soil and receiver to measure such field. The soil ECa is derived from these electromagnetic measurements. Though continuous robotic measurements would benefit irrigation models, this configuration introduces the possibility that metal and electronic components of the robot can interfere with the sensor measurement. The placement and orientation of the sensor on the platform is critical since the mere presence of the robot in proximity to the sensor can interfere with the sensor reading. Sensor placement is also constrained by the robot's size, weight, and power (SWaP) requirements to be both portable and effective at traversing uneven terrain.

In typical applications, SM surveys with EMI sensors are carried out manually either by walking the sensor in the field, or by driving field vehicles with a trailing sensor (see FIG. 1A and FIG. 1B). Both approaches are time-consuming, labor-intensive, and limit broad-scale adoption of this technology for frequent SM mapping. Established standard operation procedures recommend that ECa measurements should not be carried out on very dry soils, especially in arid, semi-arid and Mediterranean climates where the space between tree rows of micro-irrigated orchards are generally very dry because irrigation only wets soils very close to the drip emitters. Depending on soil type and irrigation strategy, moist soil is often found up to 1-1.5 m away from drip emitters. In these orchard systems, ECa measurements should thus be carried out close to the trees, along the drip-lines. Previous research on SM sensing robots use larger platforms and very expensive sensor technology such as cosmic-ray sensors. This limits how close the sensors can get to the region of interest and how frequently the surveys can be conducted. Thus, small, portable, and cost-effective SM survey robots may improve ECa measurement accuracy by bringing the EMI sensor closer to the tree roots and increase survey frequency.

Soil apparent electrical conductivity (ECa) is a vital metric in Precision Agriculture and Smart Farming, as it is used for optimal water content management, geological mapping, and yield prediction. Several existing methods seeking to estimate soil electrical conductivity are available, including physical soil sampling, ground sensor installation and monitoring, and the use of sensors that can obtain proximal ECa estimates. However, such methods can be either very laborious and/or too costly for practical use over larger field canopies. Robot-assisted ECa measurements, in contrast, may offer a scalable and cost-effective solution.

In general, soil conductivity is mainly estimated in-situ, using three distinctive methods; moisture meters (hydrometers) installed into the ground, time-domain reflectometers, and measurement of soil electromagnetic induction (EMI). In the first two cases, growers install and use decentralized sensor arrays to gather information from selected points on the field. A main drawback of these approaches is that they provide discrete measurements and hence sparse information over the complete field, which may lead to less efficient agricultural tactics and higher costs while aiming to scale over larger fields. On the other side, ECa is measured geospatially (on-the-go) with Electrical Resistivity methods and EMI sensors. The EMI measurements of soil apparent electrical conductivity can be performed in a continuous manner and proximally, whereby a farm worker walks through the field holding the EMI sensor or a field vehicle that carries the sensor is driven around (FIG. 1A and FIG. 1B). In this way, a more spatially-dense belief about field irrigation is formed as the sensor can either gather continuous measurements of selected regions within the field or sparse measurements from specific points. FIG. 1A depicts an instance from a manual survey of soil moisture in an olive tree field, with the use of the GF CMD-Tiny EMI instrument. Despite the benefits afforded by continuous EMI soil measurements, a noteworthy drawback is that such surveys may not scale well in larger fields as they can become quite labor-intensive depending on the broader area of inspection and weather conditions (e.g., heat fatigue). The standard of practice (besides manual operation) is to use an ATV (FIG. 1B) that carries a (often larger) sensor; however, due to its size, it may be hard to get the sensor close to the tree roots where estimating soil apparent electrical conductivity is most crucial.

For these and other reasons there is a need for an integrated robotic soil sensor platform that can serve as a reliable and accurate platform for performing continuous ECa measurements as part of a SM survey.

SUMMARY

Consistent with the disclosed embodiments, an apparatus includes a mobile platform, a sensor physically coupled to the mobile platform, and a control system mounted on the chassis and communicatively coupled to the sensor. The mobile platform includes a chassis; the mobile platform to traverse an agricultural field. The sensor is physically coupled to the mobile platform. The sensor, in operation, makes one or more soil apparent electrical conductivity measurements in the agricultural field. In some embodiments, the mobile platform has an optimal chassis to sensor distance that is optimum for avoiding electrical interference between the sensor and the chassis. The sensor is positioned at an operational distance from the chassis that is less than the optimal chassis to sensor distance. In some embodiments, the control system provides geo-referencing and autonomous logging of the one or more soil apparent electrical conductivity measurements. In some embodiments, the mobile platform includes an adjustable platform to hold the sensor. In some embodiments, the sensor is physically coupled to the mobile platform using carbon-fiber rods. In some embodiments, the mobile platform has a direction of travel, the sensor is oriented substantially perpendicular to the direction of travel. In some embodiments, the apparatus includes a ground clearance distance that defines an operational distance between the sensor and the agricultural field of between about forty-five and fifty-five millimeters. In some embodiments, the mobile platform includes wheels to contact the agricultural field. In some embodiments, the sensor is tuned such that the one or more soil apparent electrical conductivity measurements have high-accuracy to a soil depth of about 0.7 meters. In some embodiments, the agricultural field includes terrain deviations and the mobile platform includes an approach angle α and a departure angle β selected to enable the mobile platform to traverse the agricultural field and make useful measurements. In some embodiments, the agricultural field includes micro-irrigated orchard systems. In some embodiments, the terrain deviations are about twenty-five millimeters or less.

Consistent with the disclosed embodiments, a method for identifying a substantially optimal position for positioning a sensor on a mobile platform is disclosed. The method includes identifying a first distance from the mobile platform to allow for reduced electromagnetic interference from the mobile platform. The method also includes identifying a second distance from the ground to allow for reduced vibration and fluctuating measurements in a non-uniform terrain, the substantially optimal position for locating the sensor being a location defined by the first distance and the second distance that enables obtaining a plurality of apparent electrical conductivity measurements that have standard deviations that closely match standard deviations of manually obtained measurements. In some embodiments, identifying a first distance from the mobile platform to allow for reduced electromagnetic interference from the robot includes identifying a distance of about sixty centimeters. In some embodiments, identifying a second distance from the ground to allow for reduced vibration and fluctuating measurements in a non-uniform terrain comprises selecting a height of about six centimeters.

Consistent with the disclosed embodiments, a method is disclosed. The method includes navigating an agricultural field with a mobile platform. The method includes generating a real-time position and orientation for the mobile platform. The method includes performing one or more soil apparent electrical conductivity measurements of the agricultural field from a sensor physically coupled to the mobile platform. The method includes synchronizing the one or more soil apparent electrical conductivity measurements with the real-time position. The method includes geospatial mapping and autonomously logging the one or more soil apparent electrical conductivity measurements. The method includes processing the one or more soil apparent electrical conductivity measurements to generate one or more soil moisture values.

In some embodiments, navigating the agricultural field with the mobile platform includes traversing a root zone under tree canopies of an olive grove. In some embodiments, navigating the agricultural field with the mobile platform comprises navigating a muddy agricultural field. In some embodiments, the method further includes delivering high-linearity scores in real survey scenarios at a citrus grove under different irrigation levels by scoring more than about 90% in Pearson correlation coefficient in both plot measurements and estimated apparent electrical conductivity maps generated by kriging interpolation. In some embodiments, the method further includes utilizing a simulation software package that provides estimation of terrain traversability in relation to identifying substantially optimal sensor placement. In some embodiments, navigating the agricultural field with the mobile platform includes generating platform control commands from a waypoint-based trajectory planner. In some embodiments, navigating the agricultural field with the mobile platform comprises navigating along one or more drip lines in the agricultural field. In some embodiments, the method further comprising scheduling irrigation for the agricultural field based on the soil moisture values. In some embodiments, processing the one or more soil apparent electrical conductivity measurements to generate the one or more soil moisture values includes including a correction factor in the processing to account for the mobile platform influencing the one or more soil apparent electrical conductivity measurements. In some embodiments, the method further includes displaying the soil moisture value in real time. In some embodiments, the method further includes determining the maximum practical sensor mounting distance $d_h$ and angles α and β that allow the robot to traverse uneven terrain with deviations of plus or minus about 25 millimeters from level after mounting the sensor on the mobile robot without tipping, stalling, or colliding the sensor into the ground.

DETAILED DESCRIPTION

Reference will now be made in detail to exemplary embodiments, discussed with regards to the accompanying drawings. In some instances, the same reference numbers will be used throughout the drawings and the following description to refer to the same or like parts. Unless otherwise defined, technical and/or scientific terms have the meaning commonly understood by one of ordinary skill in the art. The disclosed embodiments are described in sufficient detail to enable those skilled in the art to practice the disclosed embodiments. It is to be understood that other embodiments may be utilized and that changes may be made without departing from the scope of the disclosed embodiments. For example, unless otherwise indicated, method steps disclosed in the figures can be rearranged, combined, or divided without departing from the envisioned embodiments. Similarly, additional steps may be added or steps may be removed without departing from the envisioned embodiments. Thus, the materials, methods, and examples are illustrative only and are not intended to be necessarily limiting.

Disclosed is a ground mobile robot equipped with a customized and adjustable platform to hold an Electromagnetic Induction (EMI) sensor to perform semi-autonomous and on-demand ECa measurements under various field conditions. The platform is designed to be easily re-configurable in terms of sensor placement; results from testing for traversability and robot-to-sensor interference across multiple case studies help establish appropriate tradeoffs for sensor placement. Further, a developed simulation software package enables rapid and accessible estimation of terrain traversability in relation to desired EMI sensor placement. Extensive experimental evaluation across different fields demonstrate that the obtained robot-assisted ECa measurements are of high linearity compared with the ground truth (data collected manually by a handheld EMI sensor) by scoring more than 90% in Pearson correlation coefficient in both plot measurements and estimated soil apparent electrical conductivity maps generated by kriging interpolation. The robotic solution supports autonomous behavior development in the field since it utilizes the Robot Operating System (ROS) navigation stack along with the Real-Time Kinematic (RTK) GNSS positioning data and features various ranging sensors.

Key Features of Integrated Robotic Soil Sensor Platform

A. Measuring Soil Conductivity

Figure 2:
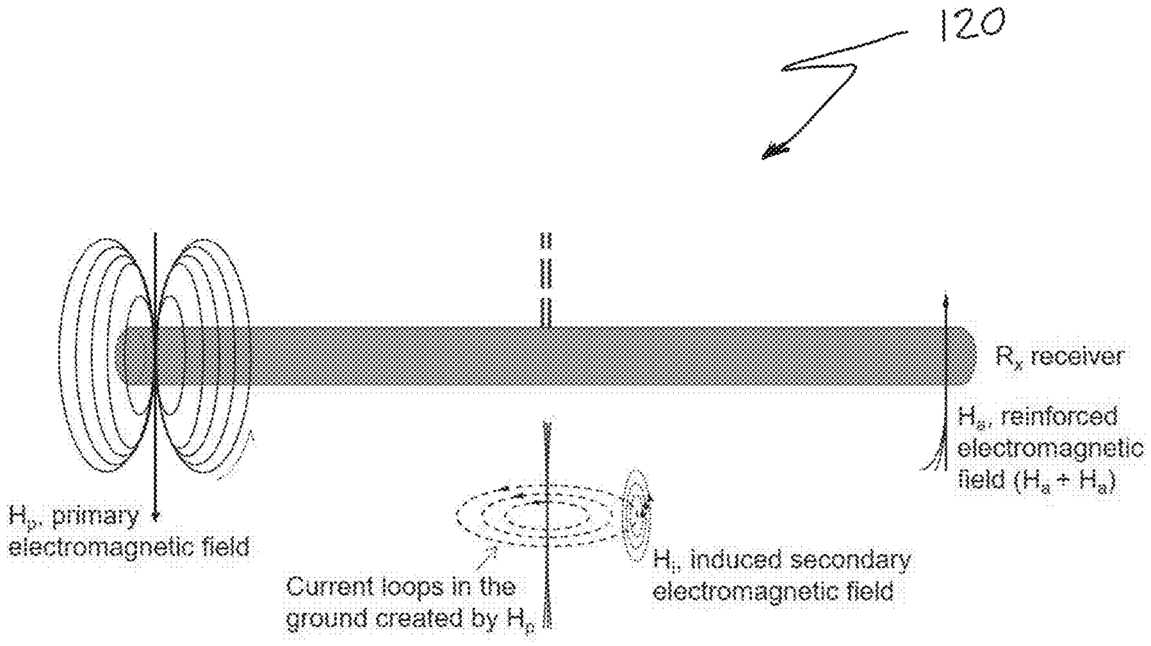
FIG. 2: Schematic of the operation of the CMD-Tiny probe sensor. This sensor can measure apparent conductivity up to 1000 mS/m with a resolution of 0.1 mS/m with an accuracy of ±4% at 50 mS/m.

Apparent soil electrical conductivity (ECa) measures the bulk conductivity of the soil and the resulting measurement is a complex interaction of salinity, water content, and soil composition. Though the interactions may be complex, soil moisture can be reliably inferred from ECa measurements when ground-truth data are used. During operation, the EMI sensor generates a primary electric field that induces eddy currents into moist soil. These currents generate a secondary magnetic field that is then measured by the sensor's receiver. FIG. 2 depicts the sensor's operating principle. Measured ECa values serve as a reliable proxy for soil moisture when the sensor is properly calibrated.

In some embodiments, a CMD-Tiny (GF Instruments) conductivity sensor, which is a small-form sensor, is integrated with the ROSbot platform. The sensor has diameter 42.5 mm and length 500 mm and weighs 424 g (i.e., only 4% of ROSbot's total payload capacity of 10 kg). The sensor is paired with a data logger that also provides power to the former.

B. Performing Roboticized ECa Measurements

Figure 3:
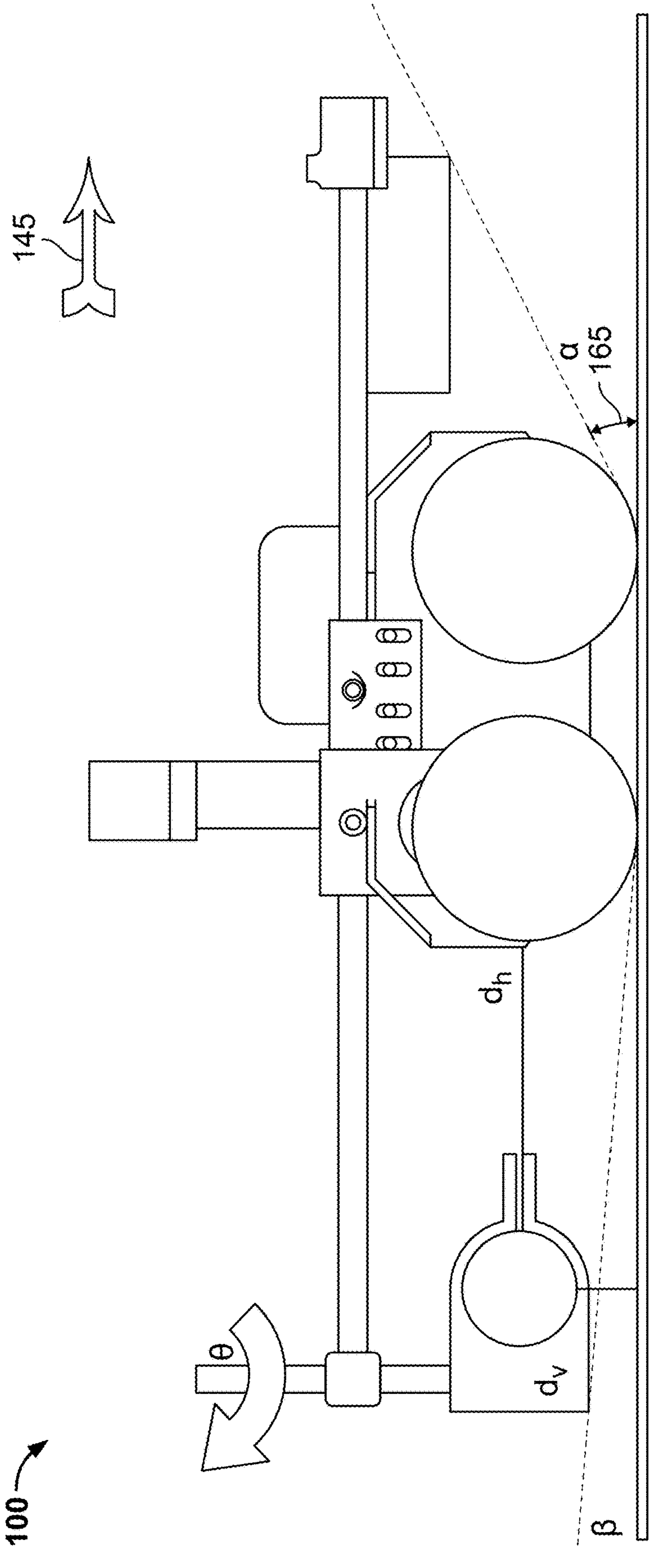
FIG. 3: One embodiment of the apparatus—a robotic platform is shown. Design parameters $d_h$, $d_v$, θ, α and β are described. The light grey arrow denotes the forward-looking direction of the robot.

The ROSbot 2.0 Pro (Husarion Robotics) is adopted as the mobile platform to deploy in the field. This compact and light-weight robot contains the necessary integrated hardware to enable stable maneuverability, remote control, and autonomous navigation. As shown in FIG. 3 the sensor 120, an EMI sensor in this embodiment, is orientated with respect to the robot with angle θ, installed with ground clearance $d_v$, and located away from the robot's back with distance $d_h$ to improve the SM measurement accuracy and reduce the robot's interference. The parameters also constrain the approach angle α and the departure angle β which could limit the capability of overcoming obstacles in the uneven terrain. With careful design parameter selection (discussed below), the fully-equipped robot can traverse common field terrains with deviation of ±25 mm.

C. System Software Architecture

The platform's software architecture is built upon ROS to enable automatic geospatial mapping of ECa measurements and soil moisture content in micro-irrigated orchard systems. The software consists of navigation and ECa modules that are interpreted as several ROS nodes. The navigation module utilizes an external GNSS receiver and ROSbot's odometry information fused from motor encoders and IMU to compute the robot's real-time pose (i.e. position and orientation) with an Extended Kalman Filter. Robot control commands are generated from either manual inputs or a waypoint-based trajectory planner. In field testing teleoperation was used; in some embodiments, autonomous navigation in the field can be enabled by integrating measurements from the onboard LiDAR and RGB-D camera activated for online obstacle avoidance. The ECa module extracts SM information from the EMI sensor and synchronizes the data with spatial coordinates from the navigation module. Geospatial SM data are displayed in real time and simultaneously logged into local CSV files for post-processing with ArcMap 10.8 (ESRI, Redlands, CA).

Experimental Methods and Results

A. Overview of Experimental Procedures

Development and testing of the integrated robotic soil sensor platform was conducted over four experimental stages.

1) First, a series of distinct sampling measurement were performed across diverse fields to validate repeatability and effect of distance, $d_h$, between the sensor and the main robot chassis so as to minimize EMI interference. 2) Having identified a mapping between distance ($d_h$) and EMI interference to measurements, the second stage involved integration of the sensor onto the robot in a way that the approach ($\alpha$) and departure ($\beta$) angles are such that the robot can navigate mild uneven terrain. 3) Following the platform design as per the first two stages, repeated roboticized ECa measurements were performed over discrete sampling points in the field and compared against manually-conducted measurements at the same spots in order to validate measurement repeatability and accuracy of the roboticized ECa measurements. 4) The efficacy of the overall roboticized approach was evaluated in collecting continuous ECa data, and the results compared against manually-collected continuous samples, over the same field.

B. Preliminary Sensor Placement Tests

Objective: Identify a mapping between sensor and main robot chassis distance and EMI interference, and determine viable sensor placement configurations minimizing the latter.

Figure 4:
FIG. 4: In field tests to identify EMI interference, the sensor was operated in a manual configuration to record a series of measurements at multiple distances and fixed orientation (either 0° or 90°) from the robot, over diverse fields. Here is shown an instance from testing over irrigated turf at $d_h$=25 mm and θ=0°.

Setup: The robot was placed at different locations of interest, and at different times and days to establish a rich basis, and several discrete ECa measurements were taken at fixed distance intervals from the robot, $d_h$=25, 30, 36, 41, 46, 51, 56, 61 cm, and at two orientations, $\theta$=0°, 90°. Control measurements without the robot present were also taken at all sampled locations. The test environments included grass, bare-soil, and tree roots found at the Agricultural Experimental Station of the University of California, Riverside, and at the USDA-ARS U.S. Salinity Laboratory, also in Riverside, California. Table I (Conductivity Measurements (mS/m) at Varying Distances dh (cm) Over Various Test Configurations) lists all test cases, and FIG. 4 depicts an example from testing on irrigated turf. Measurements were performed with the CMD-Tiny sensor in the 'high' mode, which is tuned by the manufacturer to provide high-accuracy ECa measurements in [0, 0.7] m soil depth.

Figure 5:
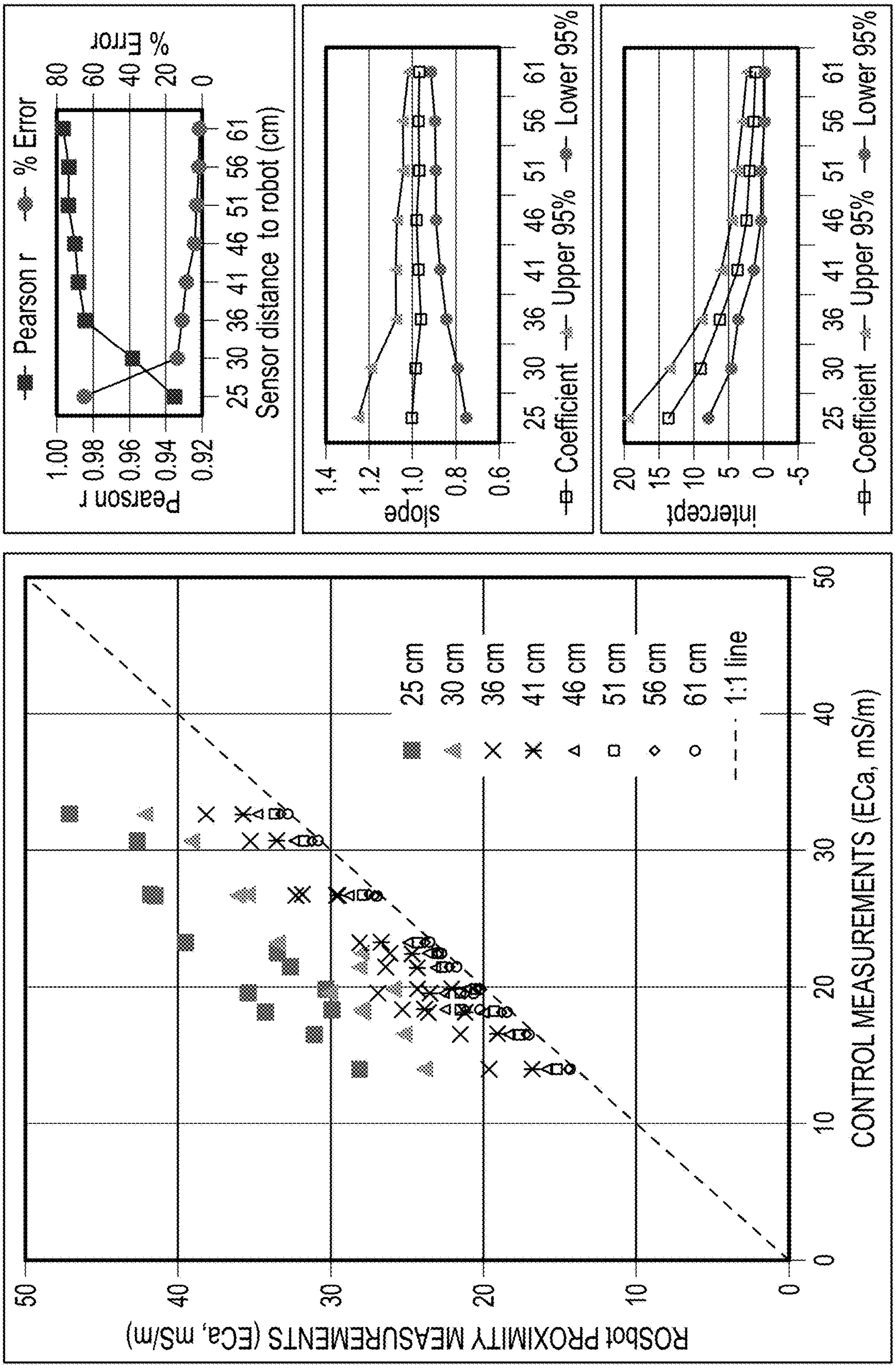
FIG. 5: For the different field locations, ECa measurements were averaged for each distance $d_h$. The resulting average values were plotted against the 1:1 control line to determine the constant linear offset. Values that have a line with a slope of 1, parallel to the 1:1 line, and a Pearson correlation close to 1 can be treated as constant linear offsets. Distances greater than 46 cm represent the best candidates for linear offsets, while additional measurements are needed to determine the true relationship at closer distances.

Results: Testing reveals that the (ideal) horizontal distance $d_h$ for the sensor would need to be at least 457 mm away from the main robot chassis in order to not to have a statistically significant influence on the EMI sensor measurements. At closer distances, the robot affects the sensor measurements, but it does not saturate the sensor. Table I (Conductivity Measurements (mS/m) at Varying Distances $d_h$ (cm) Over Various Test Configurations) contains the soil conductivity measurements at different test configurations. The column marked with denotes the control measurement at that location where the robot was not present. FIG. 5 shows how the ECa measurements differ from the 1:1 control line along with the Pearson coefficient and regression slope and intercept for each distance. As the control vs ROSbot measurements all had a slope very close to 1, the influence of the ROSbot on the sensor measurements was considered constant in the range of conductivity measured in this experiment.

TABLE I

Conductivity Measurements (mS/m) at Varying Distances $d_h$ (cm) Over Various Test Configurations

| | Distance | | | | | | | | |
|---|---|---|---|---|---|---|---|---|---|
| Test Configuration | ∞ | 25 | 30 | 36 | 41 | 46 | 51 | 56 | 61 |
| Citrus Grove, θ = 0° | 26.7 | 41.8 | 35.4 | 31.9 | 29.5 | 28.8 | 27.9 | 27.5 | 27.2 |
| | 19.8 | 30.3 | 25.9 | 24.3 | 22.1 | 21.1 | 20.8 | 20.4 | 20.1 |
| | 21.4 | 32.7 | 28.1 | 26.4 | 24.3 | 23.1 | 22.7 | 22.2 | 21.7 |
| | 18.3 | 29.9 | 28 | 25.3 | 23.9 | 22.5 | 21.5 | 21.1 | 20.2 |
| | 18.1 | 34.3 | 27.9 | 23.6 | 21.2 | 20 | 19.3 | 18.8 | 18.4 |
| | 22.4 | 33.5 | 28 | 26.1 | 24.7 | 23.6 | 22.9 | 23 | 22.7 |
| | 19.5 | 35.4 | 30.1 | 26.9 | 23.5 | 22.5 | 21.5 | 21.1 | 20.6 |
| Irrigated Turf, θ = 0° | 30.6 | 42.7 | 39.1 | 35.3 | 33.5 | 32.4 | 31.8 | 31.3 | 30.8 |
| | 32.6 | 47.1 | 42.2 | 38.2 | 35.7 | 34.8 | 33.7 | 33.3 | 32.8 |
| | 26.6 | 41.5 | 36.1 | 32.3 | 29.6 | 28.8 | 27.9 | 27.1 | 26.9 |
| | 28.2 | 42.9 | 37.8 | 33.5 | 31.6 | 30.4 | 29.7 | 29.2 | 28.9 |
| | 32.2 | 47.5 | 41.6 | 38.7 | 35.7 | 34.8 | 33.9 | 33.2 | 33.0 |
| | 28.7 | 39.2 | 35.1 | 33.1 | 31.3 | 30.4 | 29.8 | 29.5 | 28.9 |
| Irrigated Turf, θ = 90° | 28.3 | 31.2 | 30.2 | 29.4 | 29.1 | 28.5 | 28.6 | 28.4 | 28.3 |
| | 32.4 | 35.5 | 33.9 | 33.2 | 33.0 | 32.8 | 32.8 | 32.7 | 32.6 |
| | 28.8 | 31.1 | 29.7 | 29.1 | 28.8 | 28.6 | 28.7 | 28.6 | 28.4 |
| Tree roots, θ = 0° | 14.9 | 26.3 | 23.2 | 20.1 | 18.3 | 17.0 | 16.3 | 15.8 | 15.3 |
| | 13.9 | 28.1 | 23.9 | 19.6 | 16.8 | 15.9 | 15.2 | 14.4 | 14.3 |
| | 16.5 | 31.1 | 25.2 | 21.5 | 19.1 | 18.3 | 17.6 | 17.2 | 16.9 |

TABLE I-continued

Conductivity Measurements (mS/m) at Varying Distances $d_h$ (cm) Over Various Test Configurations

| Test Configuration | Distance ∞ | 25 | 30 | 36 | 41 | 46 | 51 | 56 | 61 |
|---|---|---|---|---|---|---|---|---|---|
| Tree roots, θ = 90° | 14.7 | 18.3 | 16.6 | 15.7 | 15.2 | 14.9 | 14.9 | 14.7 | 14.7 |
| Bare Soil, θ = 0° | 23.2 | 39.5 | 33.5 | 28.1 | 26.7 | 24.9 | 24.3 | 23.8 | 23.5 |
| | 22.4 | 35.0 | 31.3 | 28.1 | 25.9 | 24.8 | 23.9 | 23.4 | 23.1 |
| | 17.2 | 25.4 | 23.4 | 21.2 | 19.9 | 19.1 | 18.5 | 18.2 | 17.9 |
| Bare Soil, θ = 90° | 22.4 | 25.2 | 23.9 | 23.3 | 22.9 | 22.7 | 22.6 | 22.5 | 22.5 |
| | 18.5 | 20.9 | 20.1 | 19.6 | 19.2 | 19 | 18.9 | 18.9 | 18.9 |

With reference to Table I (Conductivity Measurements (mS/m) at Varying Distances dh (cm) Over Various Test Configurations), measurements were taken to determine the effect of the sensor angle θ. Data suggest that the ideal orientation of the sensor would be 90°, that is the sensor should be mounted sideways and parallel to the direction of motion of the robot. However, this configuration would make the robotic platform unstable; hence, we elected to proceed with the horizontal sensor orientation (i.e., the sensor is mounted perpendicular to the direction of motion).

Mounting the sensor at the ideal distance from the robot would significantly impact its mobility, hence the sensor is mounted at a closer distance (as described below) and identify a correction offset (as we described below) to account for the small, yet noticeable effect of the robot on the sensor's measurements. While the ideal placement would eliminate sensor bias, current best practices often mount the ECa sensors with metal brackets to farm equipment, which introduces a measurement bias. Though further refinement of the robotic system could reduce bias, our platform conforms to standard practices.

Finally, in the field, the measured values did not noticeably change within the resolution of the measurements when the sensor was placed on top of a short spacer (6.35 mm) or a taller one (80 mm). To provide a large margin for the departure angle (as we described below), $d_v$=50 mm was used, which will provide sufficient ground clearance without obstructing the LiDAR's field of view.

C. Vehicle Integration & Traversal Tests

Objective: Determine the maximum practical sensor mounting distance $d_h$ and angles α and β that allow the robot to traverse uneven terrain with deviations of plus or minus 25 mm from level after mounting the sensor without tipping, stalling, or colliding the sensor into the ground.

Figure 6:
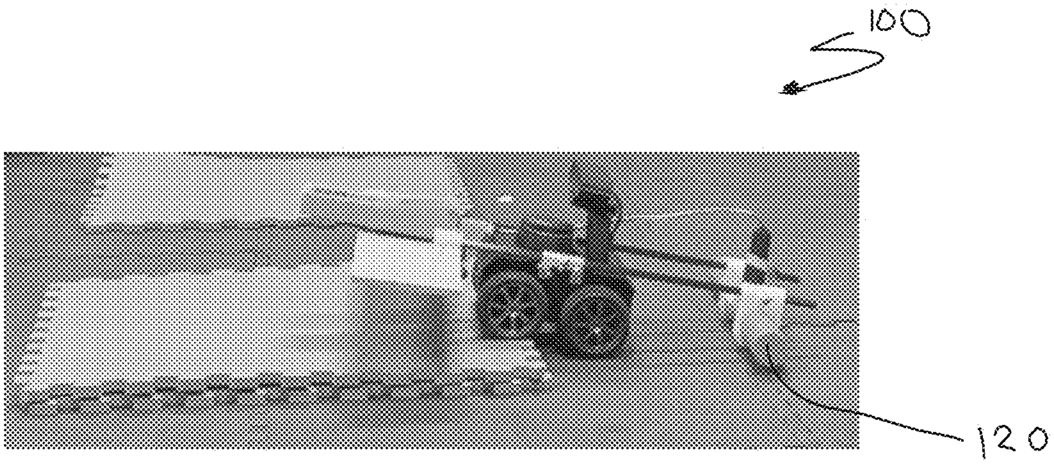
FIG. 6: To test the system's maneuverability with the sensor attached, an obstacle course was created with several stacks of 12.5 mm thick foam tiles for a total height of 25 mm. The robot was driven over the tiles at various angles and speeds to ensure no unwanted portion of the system made contact with the ground.

Setup: After completing the integration of the sensor and its data logger (mounted at the back and front of the robot; see FIG. 6), traversal tests were conducted in the lab using foam obstacles on a foam surface to confirm that the robot could indeed navigate the desired terrain (FIG. 6). Sensor mounting components were designed so that the sensor distance $d_h$ can be adjusted during the traversal tests.

The sensor was mounted using a combination of carbon fiber rods and custom 3D printed brackets. The assembly using carbon fiber rods is an appropriate means to suspend the sensor behind the robotic platform since the rods have high strength-to-weight ratio, and are rigid and non-metallic. The lightweight nature of carbon fiber aids the design goal of maximum portability. Rigidity is beneficial because it minimizes the likelihood that the cantilever sensor arm will vibrate or flex while the robot is traversing obstacles. Finally, metal support rods were not an option since they would affect the conductivity measurements. Use of metal fasteners was minimized to reduce interference with the sensor, though they could not be completely avoided for the sensor mounting.

Results: While the ideal integration configuration would have no interference between the robotic platform and the sensor, the sensor placement is constrained by the need to have approach (α) and departure (β) angles that allow the robot to traverse a field with deviations of plus or minus 25 mm from level terrain. As such, the ideal distance $d_h$ determine below is not possible to achieve. Instead, the maximum distance that prevented tipping while still allowing the vehicle to traverse the desired terrain was empirically determined at $d_h$=235 mm.

Following the tests discussed in this and the previous section, and with reference to FIG. 3, the selected system mechanical parameters are summarized in Table II (Implemented System Mechanical Parameters).

TABLE II

Implemented System Mechanical Parameters

| $d_h$ | $d_v$ | θ | α | β |
|---|---|---|---|---|
| 235 mm | 50 mm | 0° | 18.4° | 12.2° |

D. Comparative Roboticized- and Manually-collected ECa Measurement Tests

Objective 1: Quantify the impact the mounting distance $d_h$=235 mm has on the ECa measurements.

Objective 2: Determine if the introduced measurement bias is linear or nonlinear.

Setup: A row of olive trees was selected as a comparison region between roboticized- and manually-collected data. First, the robot with integrated sensor was driven down the row multiple times to collect ECa measurements along with GNSS coordinates. Then, the same measurements were collected by a human carrying the sensor. These paired measurements can be compared to determine if there are any transients from the robot during operation that could impact the EMI measurement. These tests also served to validate the robot's ability to traverse the field terrain, though these observations were qualitative not quantitative.

Figure 7:
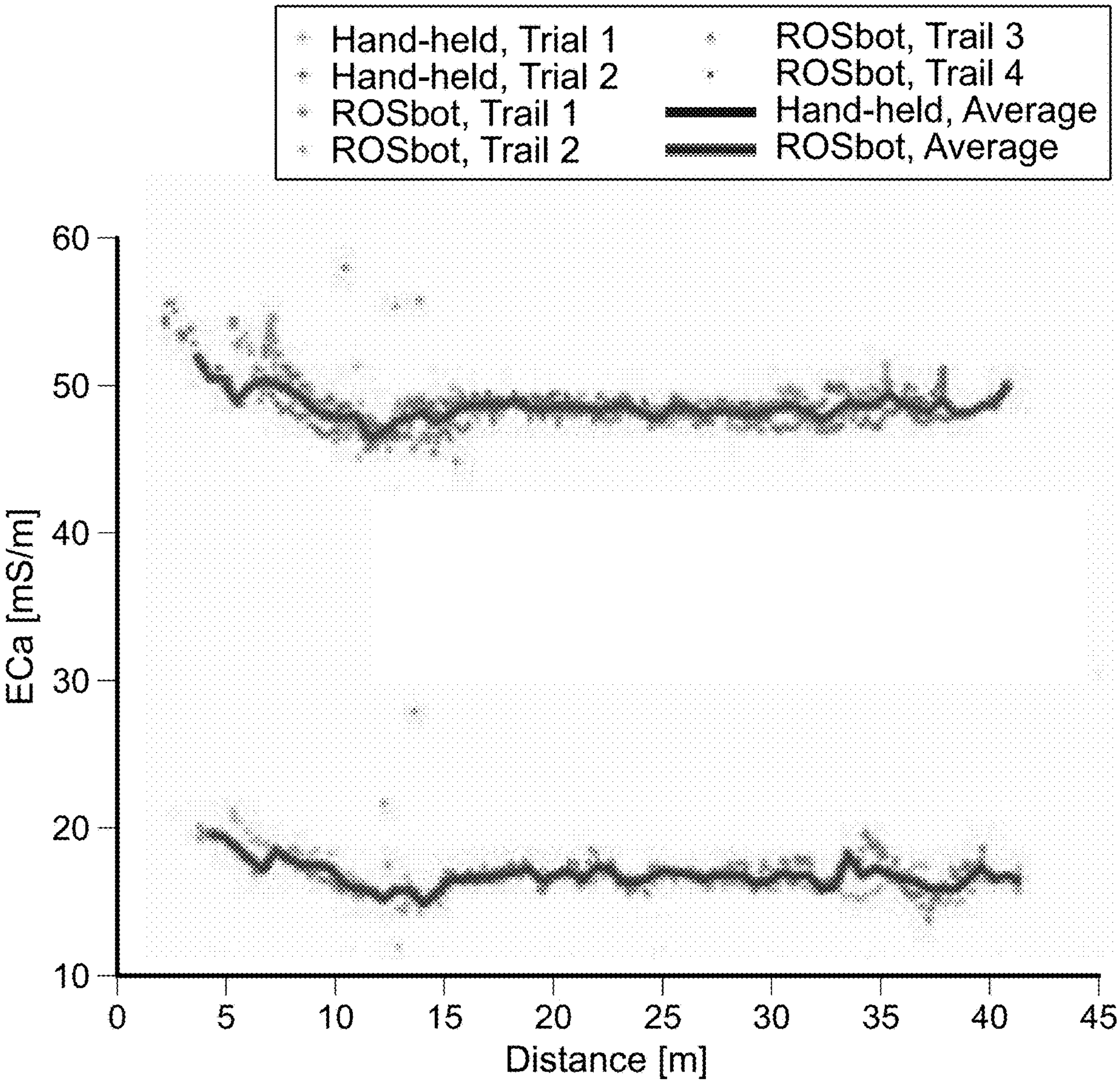
FIG. 7: ECa Measurements Comparison. Raw data measured with hand-held approach (top) and ROSbot (bottom) are scattered in dots for different trials. Average measurements are plotted in lines.

Results: Since the mechanical constraints impacted the sensor placement, the goal here is to determine if the presence of the robot introduced a constant linear offset into the ECa Measurements. FIG. 7 shows ECa measurements captured via a hand-held manual data acquisition process and when mounted on the robot. The roboticized- and manually-collected datasets were filtered to remove outliers, averaged, and then compared. The average of the hand-held ECa data set was 16.9 mS/m. The average of the dataset collected with ROSbot was 48.6 mS/m. The average difference was 31.7 mS/m. The slope of the linear relationship between the two datasets was 0.69 with a Pearson correlation coefficient of 0.72. A stronger correlation would be preferred, yet the obtained accuracy offers an acceptable trade-off between sensor measurement accuracy and compact robot design.

E. Geospatial Soil ECa Tests

Objective: Generate ECa maps at a selected study site and compare the roboticized and manually-collected measurement data.

Setup: In the extensive field test conducted, the study site was a 50 m×30 m drip-irrigated olive orchard located within the Agricultural Experimental Station of the University of California in Riverside (33° 58'24.5"N 117°19'10.3"W). Soils ([0, 0.7] m depth range) at the site were sandy loam, with sand content ranging between 54.6% and 65.9%. On Mar. 12, 2021, two ECa surveys were carried out at the study site to compare hand-held measurements with these acquired with our proposed integrated robotic soil sensor platform. In addition to the ECa measurements, GNSS position was recorded to compare the results. The robot also recorded its pose (position and orientation), although these measurements were not available during the manual hand-held process. The hand-held survey collected 461 ECa measurements, whereas the ROSbot survey collected 6901. Collected data were sampled at the same frequency, but the robot was moving slower than the human counterpart, thus leading to the increased number of samples via the roboticized approach.

Figures 8A, 8B:
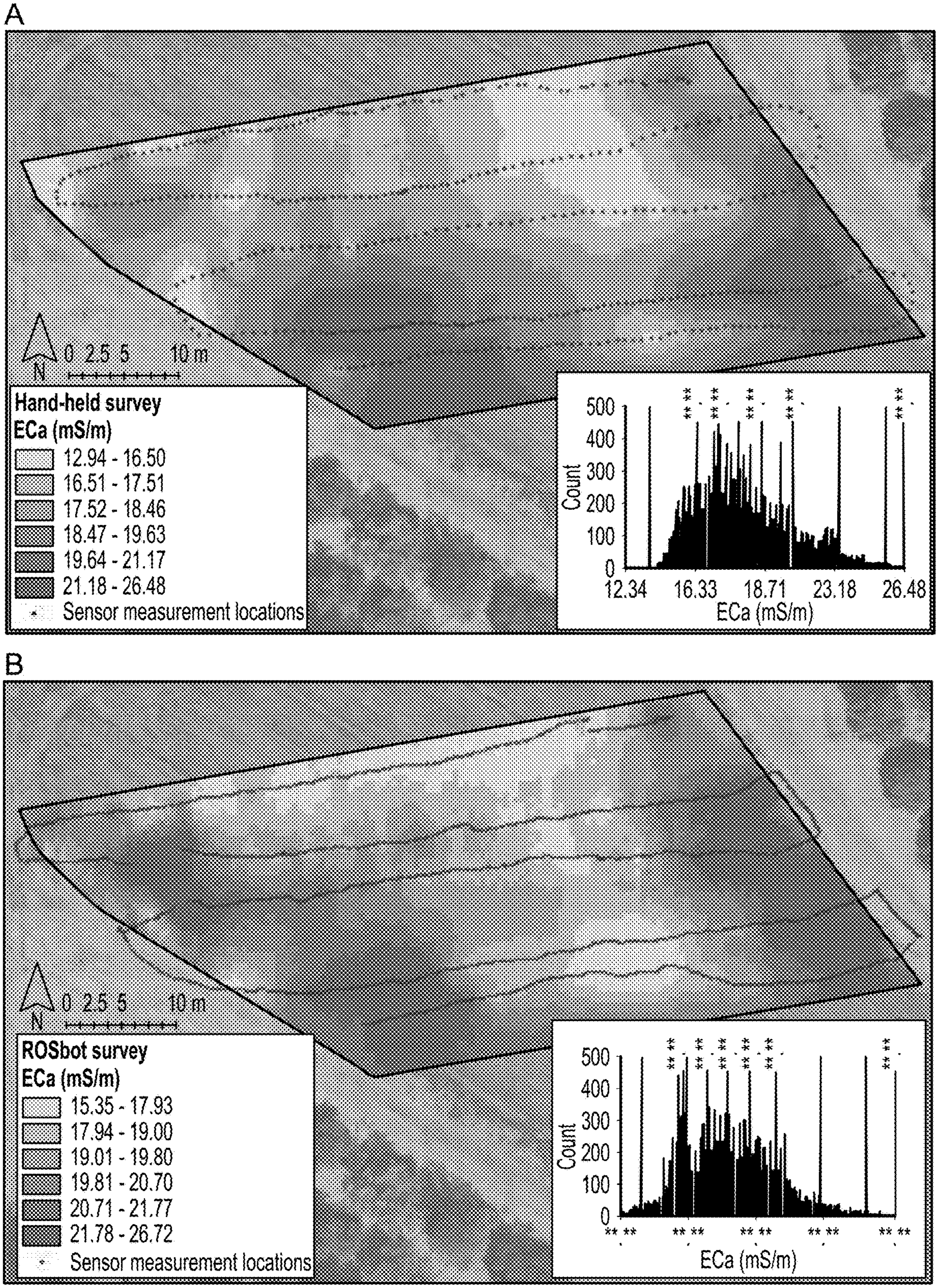
FIG. 8A and FIG. 8B: Maps of soil apparent electrical conductivity (ECa) for the 0-0.7 m soil profile at the study site: A) hand-held survey and B) ROSbot semi-autonomous survey. Scales are characterized with the quantile method. The maps' ECa frequency distribution are reported on a histogram on the bottom-right of each panel.
Figure 9:
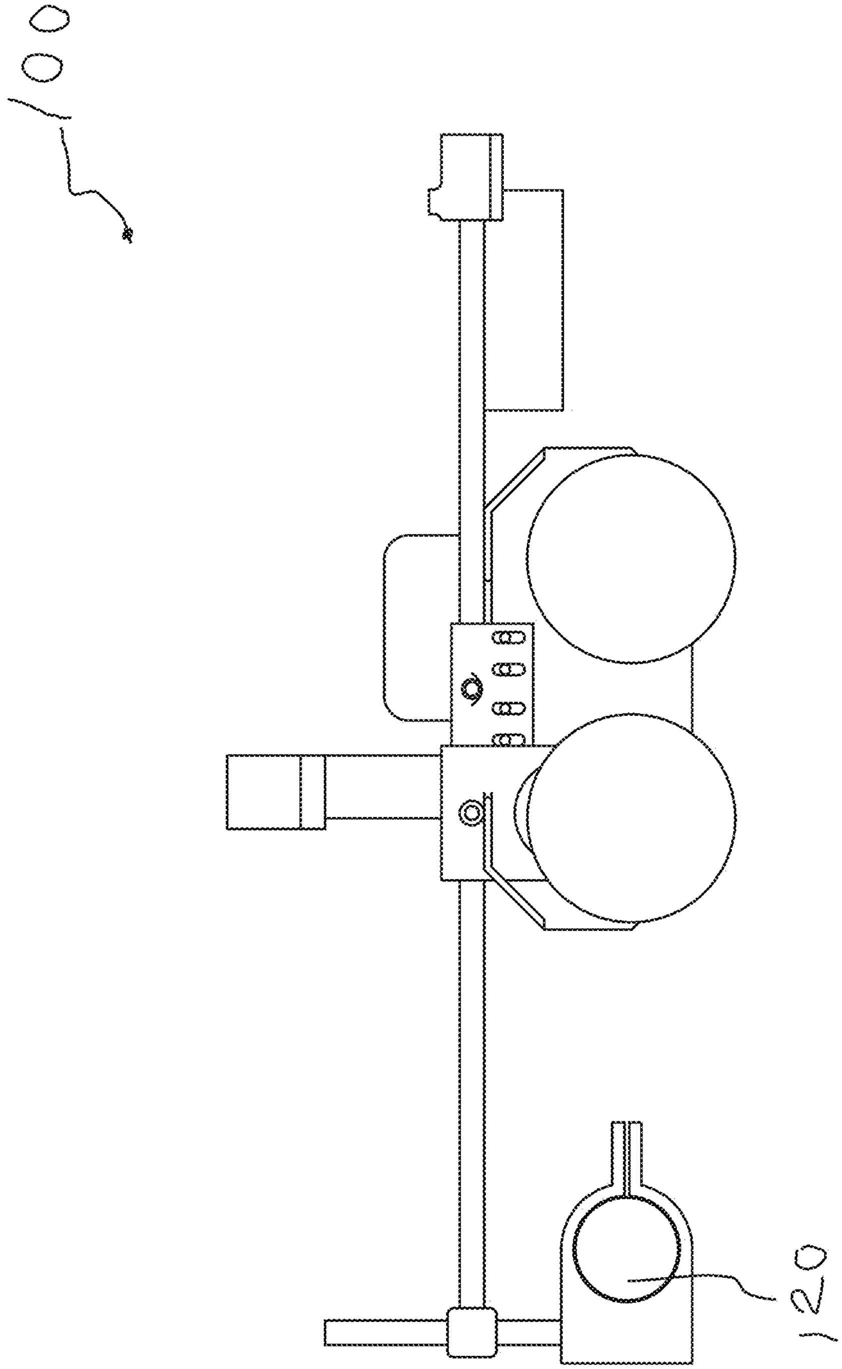
FIG. 9: Side view of apparatus in accordance with some embodiments of the present disclosure.
Figure 10:
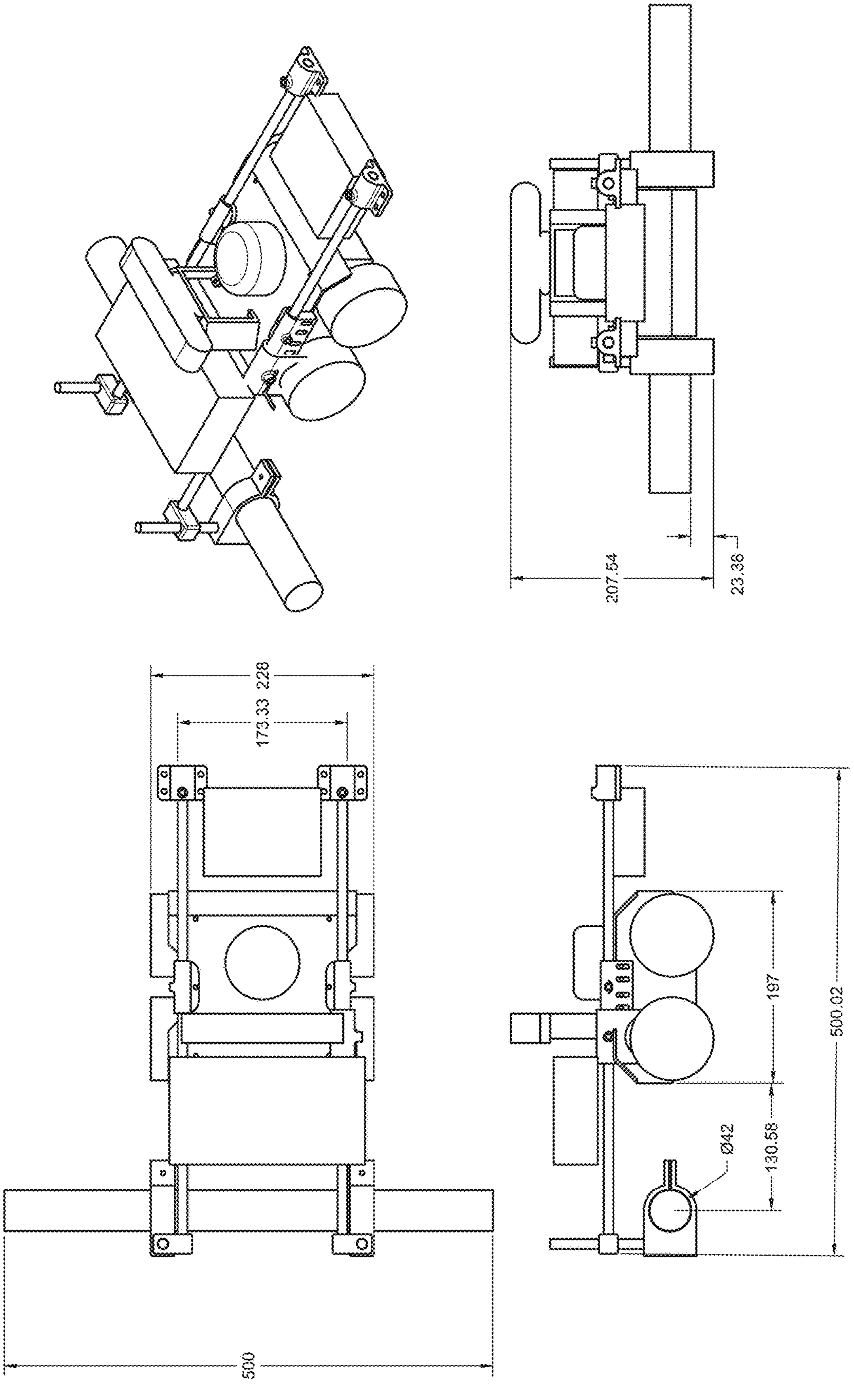
FIG. 10: Four views of some embodiments of the apparatus in accordance with some embodiments of the present disclosure including example dimensions. All dimensions are approximate and may change by +/−10-20% and be within the scope of the disclosure. The mass of the system is approximately 3.5 kg+/−about 10-20%.

Following commonly used data filtering procedures, the ECa data were normalized with a natural logarithm transformation. Then, also in line with the standard of practice, any values outside the range of plus or minus 2.5 standard deviation around the average values were removed because deemed as outliers. The hand-held ECa dataset had 2 outliers, whereas the ROSbot dataset had 137. The increased number of outliers in roboticized measurements is linked to the fact that those measurements were substantially more compared to manually-collected ones. The average of the hand-held ECa dataset was 19.0 mS/m. The average ECa value measured with the ROSbot was 53.5 mS/m. The difference (34.5 mS/m) was removed from all ECa measurements in the ROSbot dataset, to compare the variability and spatial distribution of the two datasets. In ArcMap 10.8 (ESRI, Redlands, CA), the ECa for the two datasets were spatially interpolated using simple kriging with exponential semi variogram to generate maps with 0.5 m×0.5 m resolution. These spatial maps are displayed in FIG. 8.

Results: The ECa map obtained from the hand-held survey had mean=18.78 mS/m, standard deviation=2.31 mS/m, minimum=12.94 mS/m, and maximum=26.48 mS/m. The ECa map derived from the ROSbot survey had mean=19.94 mS/m, standard deviation=1.85 mS/m, minimum=15.35 mS/m, and maximum=26.72 mS/m (Table III). The two maps revealed similar ECa spatial patterns, with the highest ECa values observed at the SE and SW portions of the study site, and the lowest ECa measured in the N and the center of the site. At the pixel-by-pixel level, the maps had a Pearson correlation coefficient=0.65. This indicates that there are some inconsistencies between the maps, possibly associated with: non-constant influence of the ROSbot on the sensor measurements, different sensor distance to soil and tilt across the two surveys, and higher detail (and variance) captured in the ROSbot survey than in the hand-held one. Observed geolocation inaccuracies are because of the employed low-resolution GPS that also introduces inconsistencies.

While the robot collected data at a slower rate than manual operation, this actually provides more accurate measurements. Current commercial practices can suffer from sensor biases and inconsistent practices. A fleet of robots could provide more consistent data and broader coverage of field regions (such as near tree roots, under dense canopies) where a human could not regularly access.

TABLE III

ECa Map Statistics.

| Survey | μ | σ | MIN | MAX |
|---|---|---|---|---|
| Hand-held | 18.78 | 2.31 | 12.94 | 26.48 |
| ROSbot | 19.94 | 1.85 | 15.35 | 26.72 |

All values are in mS/m.

Key Findings: The robot prototype demonstrates the feasibility of conducting ECa surveys using an EMI sensor mounted on a small, portable robotic platform. The ECa geospatial measurements provide real-time spatial information that can be used to infer soil water status. Precision irrigation (i.e. for distinct zones in a field) or traditional irrigation (i.e. the whole field is managed uniformly) can be scheduled based on soil water status spatial information derived from the proposed platform. The size of the platform is particularly advantageous because it brings the ECa sensor closer to the sample regions of interest such as irrigation drip-lines and tree roots where current handheld, human operated surveys cannot access. This integration approach highlights some of the design trade-offs with respect to the sensor position relative to the robotic platform, and quantifies how the robot might bias the sensor readings. The system is capable of gathering the data necessary to create spatial maps and accurate spatio-temporal soil moisture information, which is key to increasing the environmental and economic sustainability of irrigation management in precision and traditional agricultural systems.

A ROSbot 2.0 pro wheeled mobile robot was used to investigate the effect the robot body and carried sensors have on EMI sensor readings. Through a series of experiments an appropriate configuration was determined for mounting the sensor on the robot so as to minimize interference without compromising the robot's mobility and operational envelope. A software stack via the Robot Operating System (ROS) was developed to enable autonomous logging of geo-referenced ECa measurements. The platform was evaluated in spatial mapping of a 50 m×30 m drip-irrigated olive orchard, and compared against a spatial map created via manually-taken measurements with the handheld sensor. Results demonstrated the efficacy and reliability of the proposed method, thus confirming the viability of the use of small-factor mobile robots in spatio-temporal SM mapping. Accurate spatio-temporal soil moisture information is key to increasing environmental and economic sustainability of precision irrigation.

In summary, the mobile platform's small and engineered form factor allows it to gain access to and traverse the root zone under tree canopies for commercial orchards. The mobile platform utilizes carbon-fiber rods to hold and position the sensor without introducing a measurement bias. The platform is optimized for size, weight, and power (SWaP). The mobile platform is particularly suited for making soil measurements for orchard specialty crops (almonds, citrus, and other trees) in contrast to systems designed and optimized for row crops. Using a ground based mobile platform instead of an aerial "drone" allows for denser spatial resolution, which is useful when generating the soil moisture maps. Thus, less interpolation and more accurate soil moisture values are obtained with the platform of the present disclosure.

Agricultural geophysics employs non-invasive sensing techniques to characterize soil spatial variability and provide valuable insights into soil-plant-management relationships. Specifically, geospatial information on soil characteristics can indicate crucial metric used to describe the soil characteristics and water content of an area. As such, it has been used widely across applications such as in agriculture, water management, geological mapping, and engineering surveys. Information about bulk density, minerals content, pH, soil temperature, and more, can be evaluated by measuring the ECa of the field and generating a profile of the surveyed land. Thus, approximating the ECa spatial variability of a field can provide a broader understanding of the water flow through the ground, pinpoint any spots with irregular soil patterns, and finally indicate the necessity of supplying additive plant nutrients or different irrigation approaches.

This disclosure describes a mid-sized ground mobile robot solution that is able to conduct semi-autonomous and on-demand continuous EMI ECa measurements under various and larger field environments, and obtain a field-scale ECa map. The disclosure includes a solution is based on the Clearpath Jackal UGV, which is equipped with a customized and adjustable platform which can carry the EMI instrument GF CMD-Tiny. The robot supports teleoperation via Bluetooth, it can directly navigate through sending desired waypoints and can execute trajectories as it utilizes its onboard GPS and RTK positioning data along with local and global planners to reach desired goals. The design, hardware and software system integration and testing of this platform have been fully presented and evaluated in both simulated and real field-scale scenarios, including over bare fields and in muddy terrains. The proposed robot platform demonstrates high efficiency in terms of portability, traversability as well as data collection since the robot is found capable of collecting data with high linearity compared to handheld (no-robot) cases.

The following disclosure discusses key components (off-the-shelf as well as fabricated in-house) and the overall system design, and offer key system integration information. The disclosure further includes a thorough study of the tradeoffs regarding EMI sensor placement on the mobile robot that involves tools and processes we develop for both experimental testing and testing in simulation. Details and key findings from an initial testing phase validate the preliminary efficacy of the overall system are also disclosed. Full system evaluation and testing results across multiple trials in two distinctive fields are also presented.

System Design and Integration of Key Components

A. Soil Conductivity and Employed Sensor

Electromagnetic induction can help measure the soil apparent electrical conductivity of a field. The main operating principle is based on the evaluation of the induced magnetic field from the ground as transmitted by an electromagnetic conductivity meter. Specifically, the EMI transmitter emits a harmonic signal toward the ground and generates a magnetic field. Since the receiver is placed with the same dipole orientation as the transmitter, it captures the secondary (induced) magnetic field which relates to the ground conductivity, namely out-of-phase measured in mS/m and the in-phase that is a relative metric to the primary magnetic field and measures the magnetic susceptibility of the area.

Figure 11A:
FIG. 11A, FIG. 11B, and FIG. 11C: (A) Instance of the manual data collection process using the handheld EMI sensor. Manually-collected data serve as ground truth in this work. (B) The robot described this disclosure, in some embodiments, a Clearpath Jackal UGV wheeled robot, carrying a GF CMD-Tiny EMI instrument (long orange cylinder) for ECa measurements alongside a Polaris ATV. (C) GNSS positioning information for the robot to navigate autonomously as well for geo-localization and cross-reference of obtained sensor measurements is provided via an RTK-Base station.
Figure 11B:

In this disclosure a CMD-Tiny meter from GF Instruments, which features a compact and lightweight build, was used. This instrument has a control unit module that is used for configuring and logging the EMI measurements and the CMD probe that is the main magnetic sensing module. The latter component has a cylindrical shape with 50 cm length and 4.25 cm of diameter, and the total setup weighs 425 g (FIG. 11A). This EMI instrument can obtain soil conductivity measurements from 0.35 m up to 0.7 m in-ground depth according to its setup and selected resolution.

B. Mobile Robot Setup

Figures 1A, 1B:
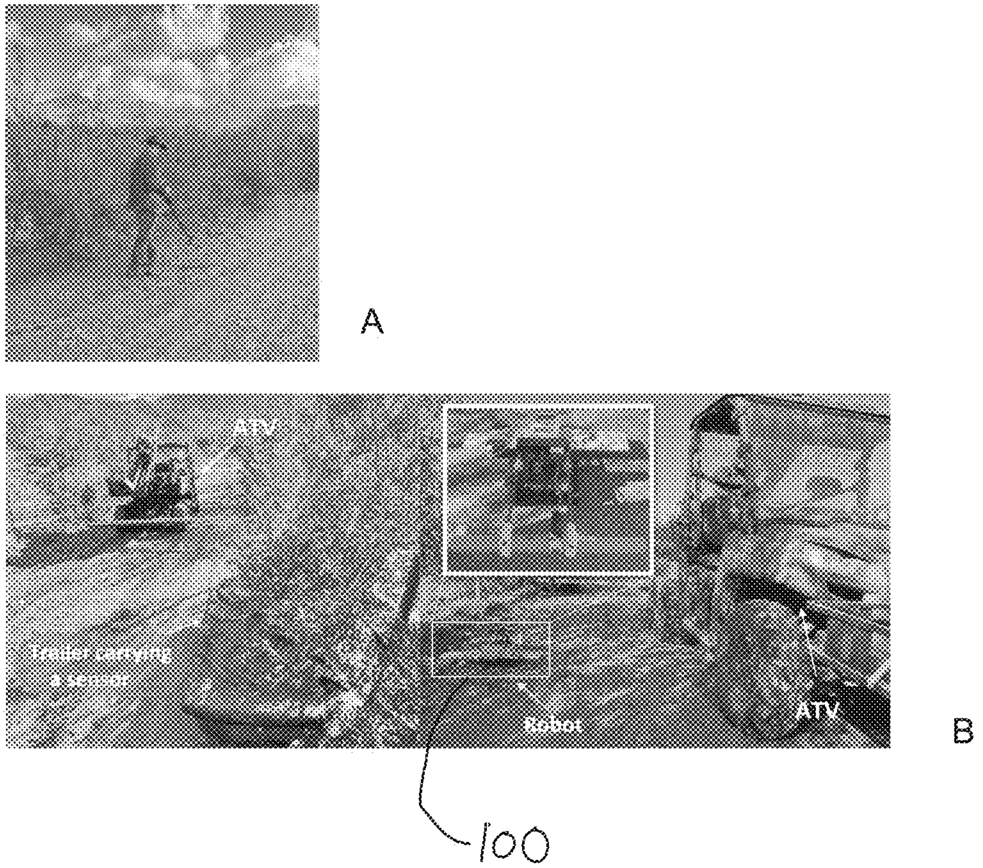
FIG. 1A and FIG. 1B: Soil moisture (SM) survey techniques using electromagnetic induction (EMI) sensors in traditional and precision agriculture. Current methods include manually-collected data obtained by walking the sensor in the field (FIG. 1A), and data obtained by a person driving a field vehicle that pulls the sensor secured on a trailer (FIG. 1B). Both methods are labor-intensive. In contrast, the disclosed method seeks to automate this process via the use of an apparatus, such a small and portable agricultural robotics (FIG. 1B). Herein, in some embodiments, the apparatus 100 includes a ROSbot 2.0 Pro wheeled robot which is retrofitted with a CMD-Tiny EMI soil sensor (inset image in bottom right panel) to conduct SM surveys over a 50 m×30 m drip-irrigated olive orchard is shown. The robot prototype is significantly smaller than the ATV and sensor trailer. Due to its small size, it is able to navigate closer to the drip-lines at the base of the trees and exert more control over the spatial component of apparent Soil Electrical Conductivity (ECa) measurements. The robot contains all necessary equipment to perform the measurement including the EMI sensor, a GNSS receiver, and router to provide a local field network.

The Clearpath Robotics Jackal robot platform, which is a UGV designed for use in outdoor and rugged all-terrain environments, was used in these experiments. The Jackal has been used in agricultural robotics research, autonomous exploration, as well as social-aware navigation. The robot's dimensions are 50.8×43.2×25.4 cm with a payload area of 43×32.25 cm for mounting various (OEM and custom) onboard modules. Its available payload capacity reaches 20 kg. The robot features an onboard NVIDIA Jetson AGX Xavier computer that is responsible for all onboard computation. On the sensors and actuators side, the robot is equipped with a GNSS receiver, an IMU module, and motorized wheel encoders (besides the custom payloads (described below) developed in this work, or additional sensors like stereo cameras and LiDAR that are routinely deployed on the robot for autonomous navigation). Additionally, the Jackal is a ROS-compatible robot, as it uses the ROS navigation stack and the ROS environment for its main functionality. The total operating time of this robot can reach up to 4 hrs depending on the use and type of the operating environment. Importantly, the required operating time on the field can vary depending on field size and type, and the desired field mapping resolution. For instance, the surveys conducted herein took place over a total period of 1.5 hrs (3 surveys each lasting for 0.5 hrs), in a 30×15 m field, and with the robot moving with a stable linear speed of 1 m/s. Under these settings, the total battery consumption never exceeded 40% during our experiments in each case, for performing the total ECa mapping of the field. The operational time of the Jackal can be expanded by the use of a secondary/additional battery. If an increased amount of surveying time and operation in even larger fields are desired, an alternative commercial wheeled robot can be employed instead (e.g., the Clearpath Robotics Husky, and Warthog UGV, or the Amiga from Farm-ng); the described method can directly apply to such robots as well. FIG. 1B depicts one embodiment of the apparatus 100—the Jackal robot equipped with various onboard sensors, in comparison to a Polaris ATV that is typically used for mechanized EMI measurements.

C. Positioning System Integration for Field Navigation

High-in-accuracy Global Navigation Satellite Systems (GNSS) are used (along with field sensors) in precision agriculture to generate, extract, and obtain field observations with spatial information. In many cases, Real-Time Kinematic (RTK) positioning is applied to provide cm-level accuracy on the captured data by using real-time corrections through an established and calibrated base station.

Figure 11C:

The Holybro H-RTK F9P GNSS series is used as the high-in-accuracy positioning module for our field experiments, which integrates a differential high-precision multi-band GNSS positioning system. By selecting specific points on the field, the RTK base station is calibrated to obtain its position at cm-level and telemetry is used to establish communication with the robot's onboard autopilot hardware. FIG. 11C illustrates an H-RTK F9P RTK base station establishment in an outdoor environment. On the robot side, the Holybro Pixhawk 4 autopilot module in rover airframe (UGV mode) is used, along with the Holybro SiK Telemetry V3 100 Mhz and the GNSS receiver to capture the RTK corrections from the base station. The MAVROS software is utilized to parse the positioning data and use them with the onboard computer through a USB connection at a rate of 10 Hz. In this way, the Jackal robot is able to reliably georeference every captured measurement in the field.

On the navigation side, the robot's captured positions are described in the World Geodetic System 1984 (WGS-84). Additionally, the Jackal uses an extended Kalman Filter, which fuses information from the onboard IMU and the wheel encoders to provide the state estimation of the robot (odometry). In this work, the Jackal is required to be able to follow a predefined GNSS-tagged trajectory, and the navsat transform node from the ROS navigation stack is used to meet this requirement. Through this approach, initially all the requested geotagged targets are transformed to the Universal Transverse Mercator (UTM) coordinate system. Given this information and through the positioning data of the robot's odometry, a static transformation is generated to describe both the UTM coordinates of the robot and the targets' position into the local robot's frame. In this way, the requested trajectory can be georeferenced and transformed into Jackal's local frame and thus the robot can follow it. It is worth mentioning that, in case the robot gets into a position where there is limited satellite visibility (i.e. GPS-denied environments), it continues geotagging the captured measurements based on pose belief estimation via fusion of the onboard IMU and wheel encoders odometry data. This method is autonomous-ready in the sense that it can directly be integrated with waypoint navigation determined readily by onboard sensors where task allocation and motion planning for (newly-perceived) obstacle avoidance can happen online. Also, mapped modalities from the flora and the fauna during the survey, can even enhance and provide a multi-modal belief about the field conditions.

Additionally, on the traversing side, the focus is on open-world navigation without the existence of obstructive objects in the path that may cause the robot to get out of track to bypass them. The robot can get over small tree branches or crops as a farm worker would do, but the ground should be relatively uncluttered for the ECa inspection as in a typical survey scenario. Also, as Jackal is an IP62 rugged robot, it has a capable high torque 4×4 drivetrain allowing it to navigate through muddy and uneven parts similar to a common ATV. In the described experiments, the system was tested in both dry and muddy environments to demonstrate our system's efficacy. The robot supports a 20 cm wheel diameter (up to 30 cm) and a variety of tire models, such as square (plastic) spike sets, which can make it even more versatile for challenging terrain types that require higher traction.

D. Robot Configuration and the Design of the Sensor Mounting Platform

Figure 12:
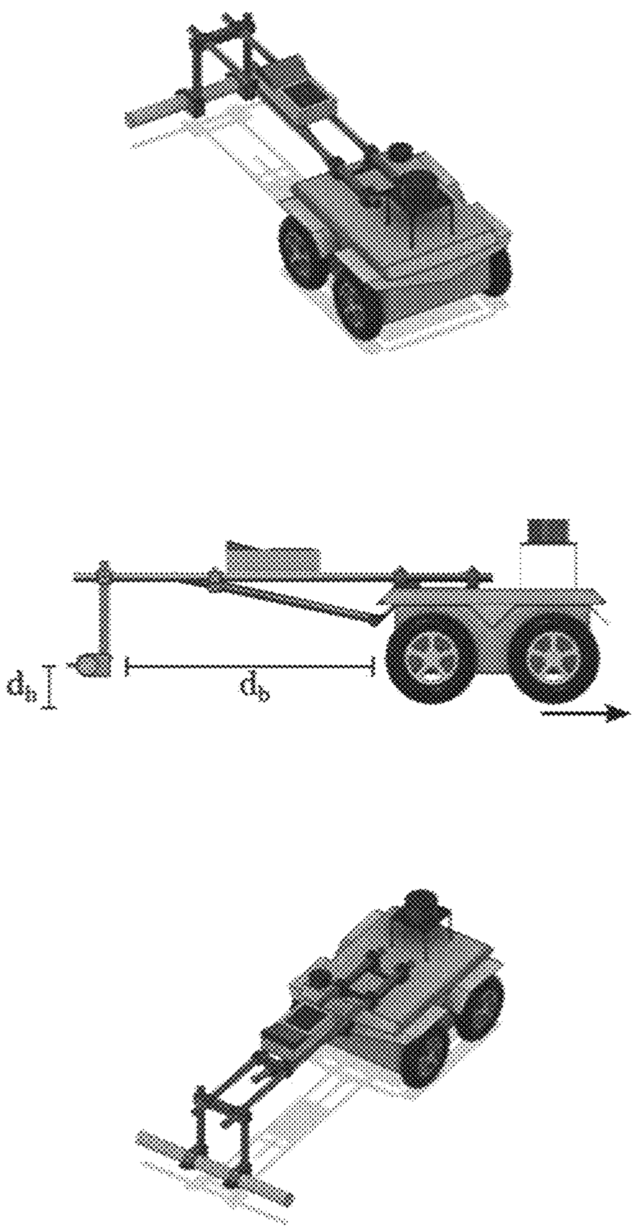
FIG. 12: CAD rendering of one embodiment of the disclosed apparatus—a Jackal's platform to hold the GF CMD-Tiny instrument. The parameters $d_h$ and $d_b$ indicate the adjustable height and distance of the sensor probe, respectively.

In this disclosure, the CMD-Tiny meter is attached on the Jackal robot. The design of the sensor platform and the definition of its adjustable parameters. The prototype renderings are depicted in FIG. 12. As the Jackal robot has a limited payload area, a module that can be attached onto the robot's top plate and extend outwards so that the sensor can get in close proximity to the ground is designed and used. In this way, the robot can carry the EMI sensor and obtain soil conductivity measurements while navigating in a continuous manner. However, the sensor's sensitivity in magnetic field measurements to other metallic and/or electronic components (like the robot itself) in view of module placement on the robot required a study of some key tradeoffs.

In particular, the EMI measurements can be distorted by the presence of other magnetic fields caused by the robot, as well as by random oscillations caused by the robot's movement. Thus, one solution would be to place the sensor as far as possible from the robot (i.e. large value for parameter $d_b$) and as close to the ground as possible (i.e. small value for parameter $d_h$). However, as distance $d_b$ increases (FIG. 2), the moment arm of the payload increases, which in turn can lead to higher power consumption of the robot. In addition, the magnitude of the oscillations (which directly affects EMI measurement consistency) will also increase. Finally, the longer the distance the worse the capability of the robot to traverse uneven terrain and/or negotiate dips and bumps that are bound to exist in the field in practice, as possible sensor collisions with the ground can occur if height $d_h$ is not sufficiently large. For these reasons, an adjustable platform is designed to support multiple configurations of the CMD-Tiny meter's control unit and probe position, relative to the robot's main body, and study the tradeoff between measurement consistency and robot traversability to identify an optimal sensor placement as described below.

FIG. 12 provides multiple views of the designed platform in CAD (Fusion 360), with all the designed parts included in the final assembly. PVC tubes of 80 cm length, 10 mm diameter, and SCH 80 wall thickness serve as the basis for an expandable and rigid structure to mount the sensor (cylindrical part) as well as its associated data collection logger (rectangular part placed on top of the two long PVC tubes). Additionally, a shorter PVC tube of 30 cm length, has been installed along with an intermediate support mounted on the Jackal's front bumper to enhance the stability of the overall EMI module. On the robot side, two supports are installed on the Jackal's top chassis to mount the two PCV tubes, and a unified support has been installed on the opposite side to hold the sensor's cylindrical probe. The latter support is crucial in allowing for reconfiguring the position and height from the ground of the probe and can be sturdily fixed in place when in use. Also, the total length of the sensor holder platform can be modified by the supports which are installed on the top chassis. Fabricated components of the platform were all 3D printed in polylactic acid (PLA) material.

Development and Calibration for Optimal Sensor Placement

The optimal sensor placement in terms of the robot body is determined by two factors: 1) electromagnetic interference from the robot chassis and its onboard electronics, and 2) robot terrain traversability. The optimal solutions to each of these factors on their own are in fact opposing each other. Indeed, to minimize electromagnetic interference, the sensor should be placed as far from the robot as possible. On the contrary, the longer the extension of the sensor holding platform from the robot's center of mass, the worse it becomes to overcome obstacles without risking to collide the sensor with the ground (FIG. 2), in addition to increasing the moment arm of the cantilever which in turn would increase the required motor torque to move without tilting forward (that also leads to higher power consumption and lower operational time). Substantially optioma sensor placement in two distinct settings is described. First, the robot's interference on the EMI measurements is experimentally benchmarked for a given fixed distance from the ground ($d_h$=5 cm) and for varying distances of the probe ($d_b \in [10, 100]$ cm). Second, terrain traversability while considering a subset of viable distances identified from the first step and two distinctive sensor height values to better understand the role of robot oscillations onto potential probe collisions with the ground. To make this process systematic, a realistic simulated environment is created and this initial set of traversability evaluation in simulation is conducted. This process yields a set of candidate probe placement distances ($d_b$) as a function of probe height off the ground ($d_h$). Additionally, feasibility experimental testing is performed in measuring continuous ECa over small areas to both narrow down the range of viable configurations and to validate optimal sensor placement).

of values for better understanding of the robot's electromagnetic interference, sampling points were either irrigated recently or non-irrigated. At the beginning of each experiment, handheld measurements were performed with the CMD-Tiny sensor, with no presence of any device that may generate additional electromagnetic fields. These measurements serve as the baseline. With these as reference, the UGV with the CMD-Tiny sensor were placed in different configurations and the data collection process was repeated, each time increasing their relative distance within the range of [10, 100] cm at a step of 10 cm. Soil conductivity data collected from these field tests are shown on Table I (Soil Conductivity Measurements in Evaluating Robt Electromagnetic Interverence) below.

TABLE I

Soil Conductivity Measurements in Evaluating Robot Electromagnetic Interference

| Field Type | | Distance between the robot and the probe ($d_b$) for constant probe height off the ground ($d_h$ = 5 cm) | | | | | | | | | |
|---|---|---|---|---|---|---|---|---|---|---|---|
| mS/m | ∞ | 10 cm | 20 cm | 30 cm | 40 cm | 50 cm | 60 cm | 70 cm | 80 cm | 90 cm | 100 cm |
| Bare Field | 13.9 | 39.1 | 85 | 38 | 26.2 | 19.8 | 17.1 | 15.6 | 14.9 | 14.6 | 14.6 |
| | 9.9 | 36.8 | 58.4 | 28.8 | 18 | 13.4 | 11.6 | 10.8 | 10.4 | 10.2 | 10.1 |
| | 10.9 | −2 | 88.7 | 38.8 | 24.4 | 16.2 | 13.2 | 12.1 | 11.8 | 11.4 | 11.2 |
| | 13.2 | −17.8 | 78.4 | 33.8 | 22.5 | 18.1 | 15 | 14.1 | 13.7 | 13.3 | 13.1 |
| | 10.3 | 66 | 61.8 | 30.3 | 20.2 | 15.4 | 12.8 | 11.5 | 11 | 10.7 | 10.5 |
| Mean (μ) | 11.64 | 24.42 | 74.46 | 33.94 | 22.26 | 16.58 | 13.94 | 12.82 | 12.36 | 12.04 | 11.90 |
| Standard Deviation (σ) | 1.80 | 33.83 | 13.67 | 4.47 | 3.26 | 2.46 | 2.15 | 1.98 | 1.89 | 1.85 | 1.90 |
| Olive Tree Grove | 25.3 | 77.8 | 90.2 | 51.9 | 37.4 | 30.6 | 28 | 26.5 | 26 | 25.6 | 25.5 |
| | 26 | 47.2 | 96.1 | 51.3 | 36.3 | 30.5 | 28.1 | 27 | 26.6 | 26.4 | 26.2 |
| | 21.8 | 7.8 | 106.3 | 50.6 | 34.1 | 27.8 | 24.4 | 23.1 | 22.4 | 22.1 | 21.9 |
| | 30.3 | 50.8 | 105.3 | 55.2 | 41.3 | 35.2 | 33.1 | 31.6 | 31 | 30.8 | 30.6 |
| | 23.2 | 59.4 | 87.9 | 48.1 | 32.3 | 29 | 25.6 | 24.5 | 24.1 | 23.8 | 23.6 |
| Mean (μ) | 25.32 | 48.60 | 97.16 | 51.42 | 36.28 | 30.62 | 27.84 | 26.54 | 26.02 | 23.74 | 25.56 |
| Standard Deviation (σ) | 3.25 | 25.69 | 8.44 | 2.56 | 3.43 | 2.81 | 3.34 | 3.23 | 3.24 | 3.28 | 3.28 |
| Citrus Tree Grove | 27.3 | 73.9 | 90.7 | 51.7 | 35.7 | 31.4 | 29.2 | 28.3 | 27.9 | 27.6 | 27.5 |
| | 23 | 69.2 | 85.2 | 47.2 | 33.6 | 27.7 | 25.3 | 24.2 | 23.6 | 23.4 | 23.2 |
| | 29.2 | 73.1 | 90.5 | 53.5 | 39 | 33.6 | 31.3 | 30.2 | 29.8 | 29.5 | 29.3 |
| | 32.2 | 35.6 | 101.7 | 57.8 | 43.1 | 37.2 | 34.7 | 33.4 | 32.8 | 32.5 | 32.3 |
| | 22.7 | 50.3 | 96.5 | 48.9 | 33.1 | 27.6 | 25.3 | 24.6 | 23.4 | 23.1 | 23 |
| Mean (μ) | 26.88 | 60.42 | 92.92 | 51.84 | 36.9 | 31.50 | 29.16 | 28.14 | 27.50 | 27.22 | 27.06 |
| Standard Deviation (σ) | 4.07 | 16.87 | 6.33 | 4.11 | 4.17 | 4.08 | 4.03 | 3.87 | 4.05 | 4.02 | 4.00 |

A. Determination of Robot Interference in Soil Conductivity Measurements

The first step to be examined concerns the robot's electromagnetic interference in the soil conductivity measurements. Specifically, the robot is equipped with a high-torque 4×4 motored drivetrain and various onboard sensors such as a 3D LiDAR and the GNSS receiver. Given this setup, the robot generates electromagnetic fields that may interfere with the electromagnetic field generated by the GF CMD-Tiny sensor as well as the secondary current read by the sensor, and thus cause distorted measurements.

Experimental Procedure: To examine and mitigate the robot's interference on the EMI measurements, three independent field experiments were conducted under different robot-sensor configurations in which the sensor was placed at predefined positions away from the robot's body to monitor the level of saturation. The fields that were selected for this purpose included a bare field, an olive tree grove, and an orange tree grove, which are located at the USDA-ARS U.S. Salinity Laboratory at the University of California, Riverside (33 58'21.936" N, −117 19'13.5732" E). In each field experiment, five distinct field points were selected to measure the soil conductivity at. To get a broad spectrum Column "∞" represents the handheld measurements where there is no appearance of external electromagnetic interference; the reported values are used as reference measurements. The columns starting from 10 cm until 100 cm represent the soil conductivity measurements that were made at the corresponding relative distances of the robot and the sensor's probe, at the same locations as in the handheld case. Mean and one-standard deviation values from the five trials in each of 33 distinctive cases shown on Table I are also provided.

Key Findings: Results of this first experimental benchmark reveal that the optimal placement of the EMI sensor has a lower threshold of $d_b$=40 cm away from the UGV body chassis. Specifically, numerical values reported in Table I show that the saturation is notable in the measurements when the sensor is less than 40 cm away from the robot's body. Shorter distances ({10, 20, 30} cm) exhibit both significantly higher mean value but also more variability (i.e. higher one-standard deviation) across all three fields. Especially the $d_b$=10 cm case exhibits excessive interference and clear evidence of saturation (the bare field depicts this most clearly). In contrast, larger $d_b$ values exhibit smaller interference as it can be readily verified by the reported means and one-standard deviations that converge to the baseline values. In addition, it can be observed that after some threshold distance, means and one-standard deviations do not vary significantly. In this work, this upper threshold is selected at $d_b$=70 cm.

Another interesting and unexpected observation concerns the cross-field variability. The olive and citrus orchards that are regularly irrigated yield similar values across all tests, whereas the bare field (not irrigated) has lower ECa values (as expected). However, the measured values appear to converge faster (i.e. in shorter distances) in the irrigated fields compared to the bare field. We can associate this finding with the fact that in irrigated fields the reported ECa values are a function of both actual soil electrical conductivity and electromagnetic interference from the robot, and the former dominates more rapidly as the probe distance increases. In contrast, in the bare field the actual ECa level attains much lower values, hence readings are more susceptible to electromagnetic interference and larger distances appear to be required to dampen down the interference's effect. This finding can be a useful tool to correlate soil salinity over the same field before and after planting, and while growing.

Figure 13A:
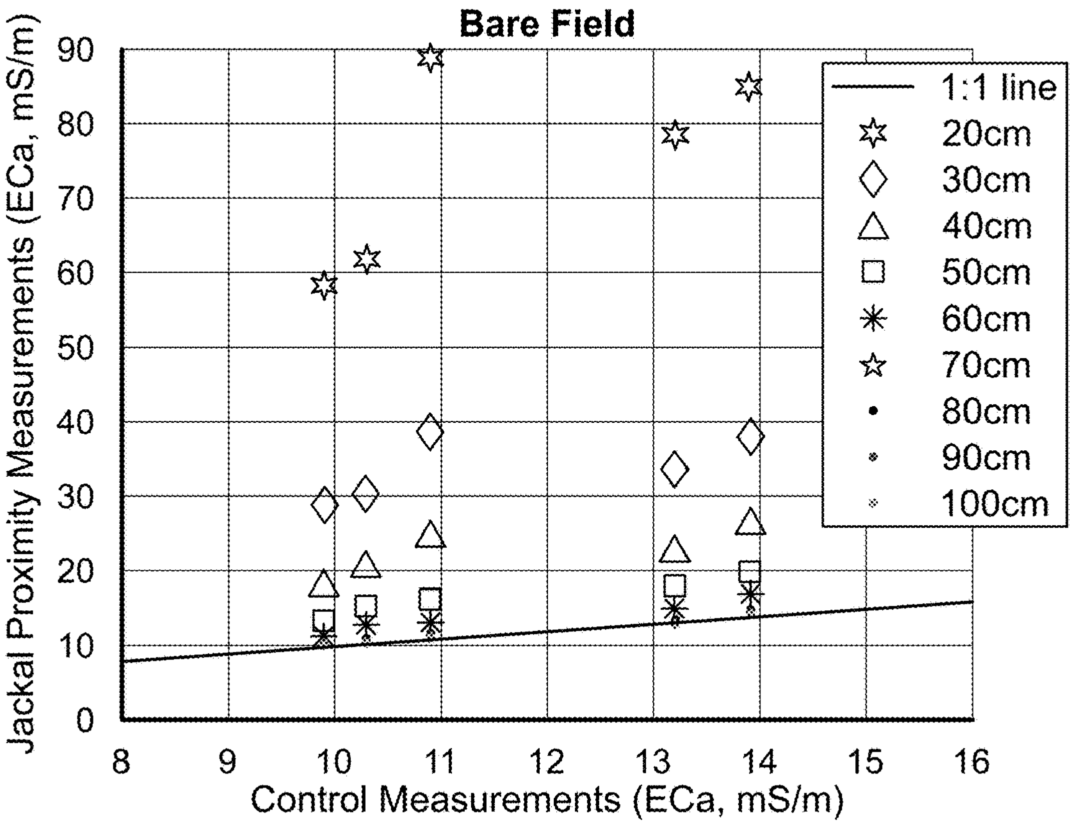
FIG. 13A, FIG. 13B and FIG. 13(C): 1:1 control lines of soil conductivity measurements for the different robot-sensor distances at the three fields.
Figure 13B:
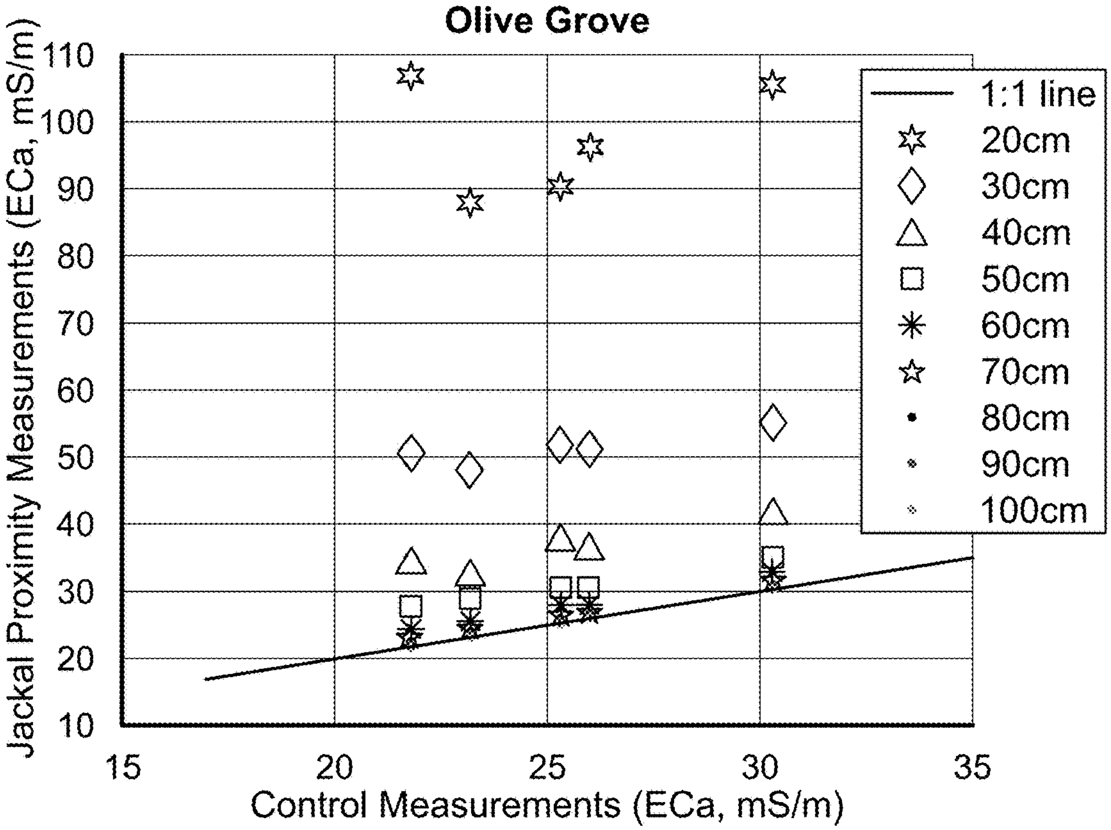
Figure 13C:
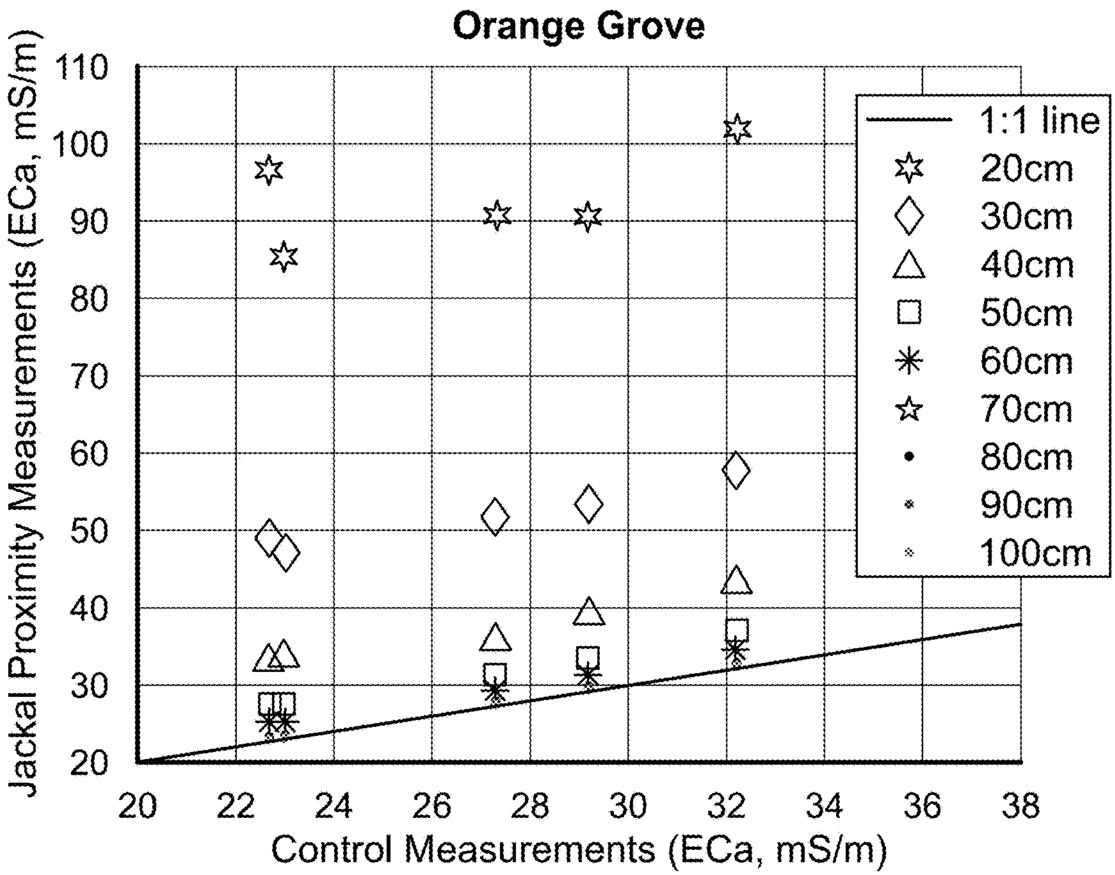
Figure 14A:
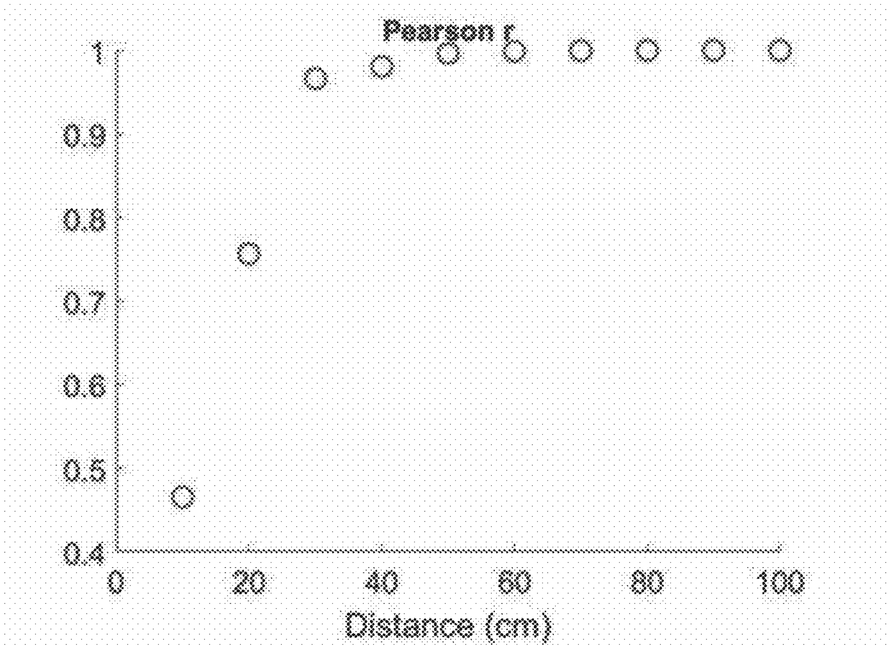
FIG. 14A, FIG. 14B, FIG. 14C and FIG. 14D: Data analysis of the different robot-sensor distances with respect to the handheld-collected (baseline) data. (A) Pearson correlation test; (B) error percentage in measurements; (C) the slope value; and (D) the intercept value are depicted.
Figure 14B:
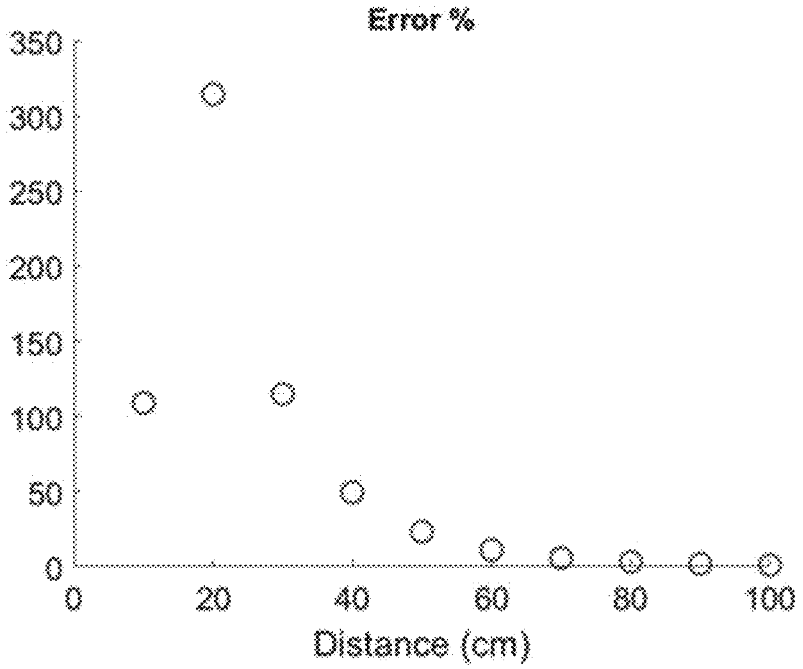
Figure 14C:
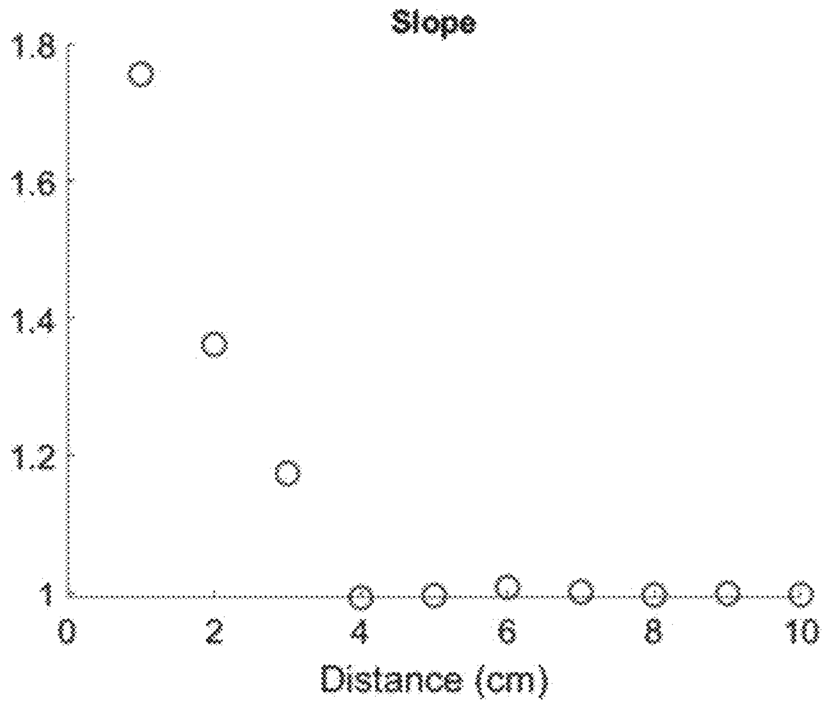
Figure 14D:
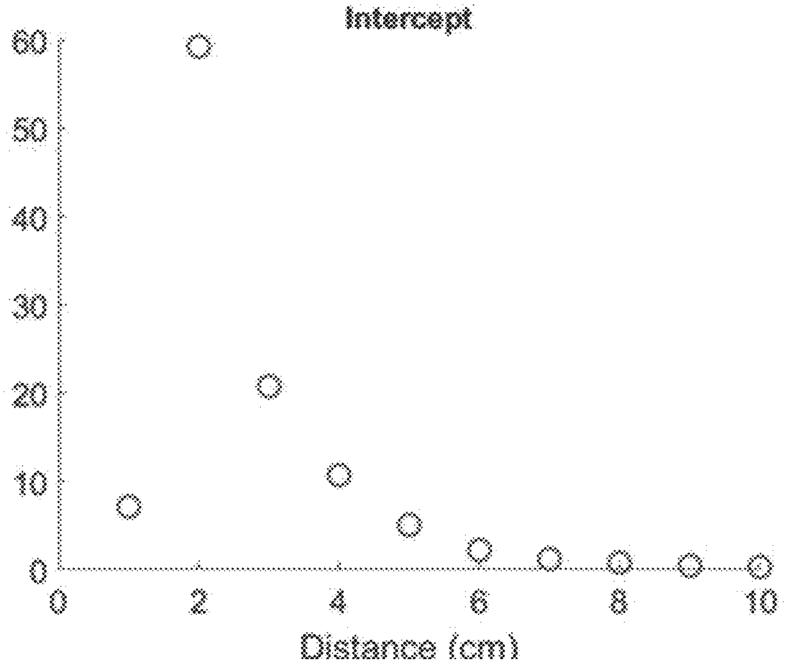
Figure 15A:
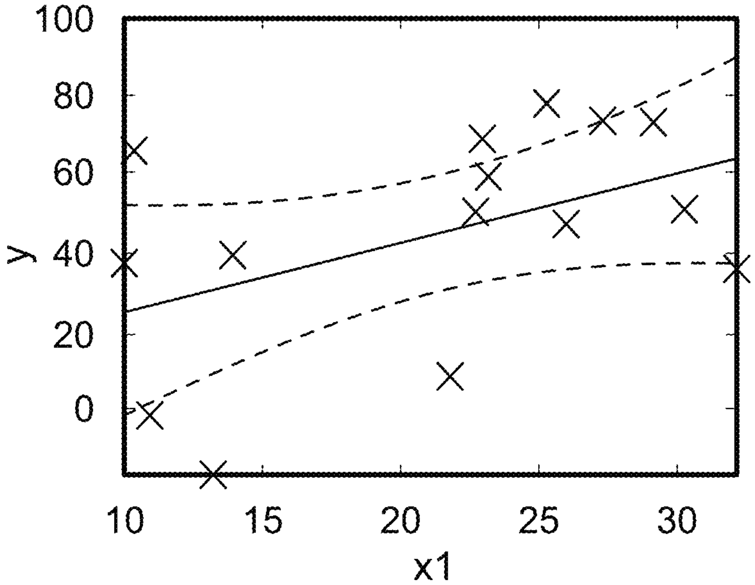
FIG. 15(A-J): Linear regression graphs of the captured conductivity data with respect to the baseline values, for evaluating the robot interference in the EMI measurements. Figs. (A)-(J) correspond to each of the cases in the range [10, 100] cm of robot-sensor distance, respectively. Upper and lower bounds of the fit are depicted with continuous curves.
Figure 15B:
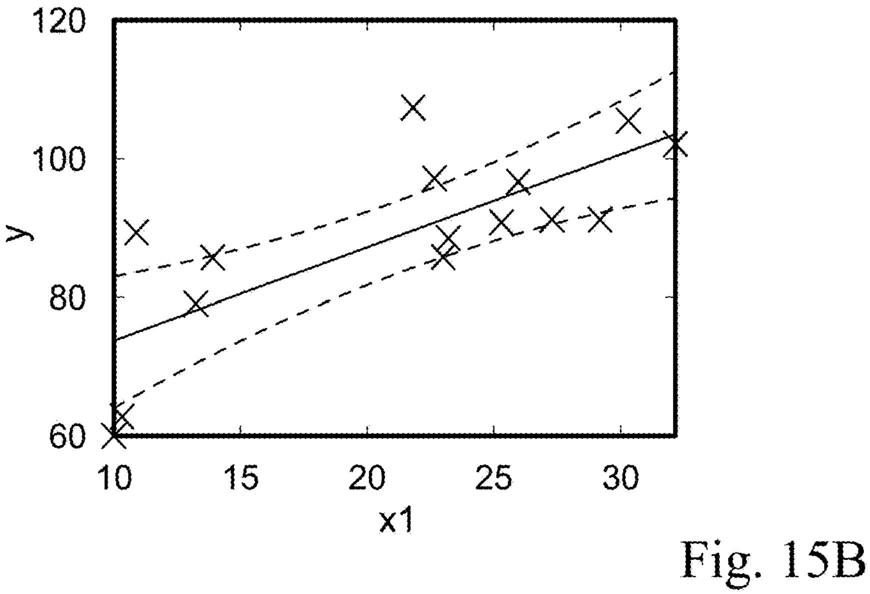
Figure 15C:
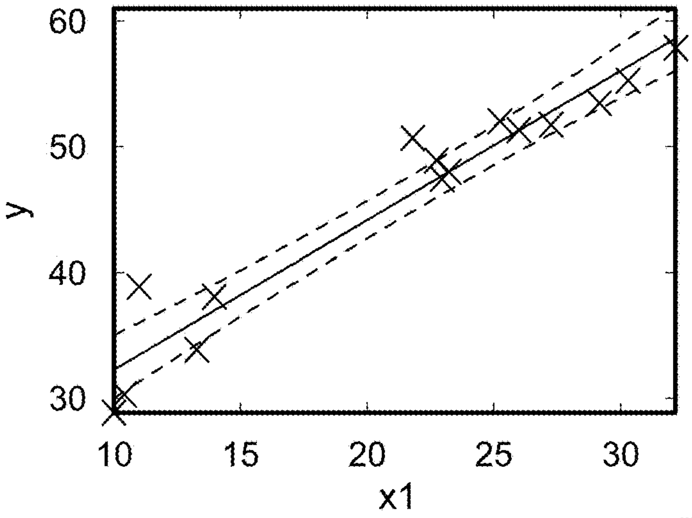
Figure 15D:
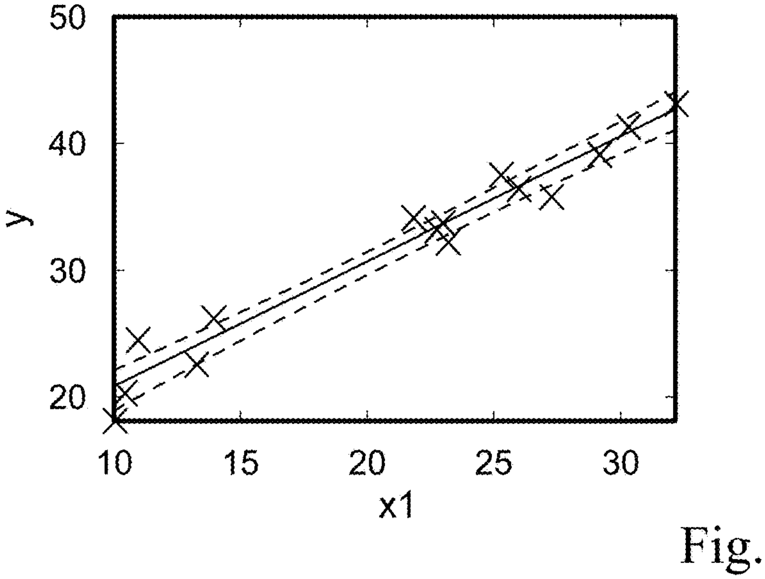
Figure 15E:
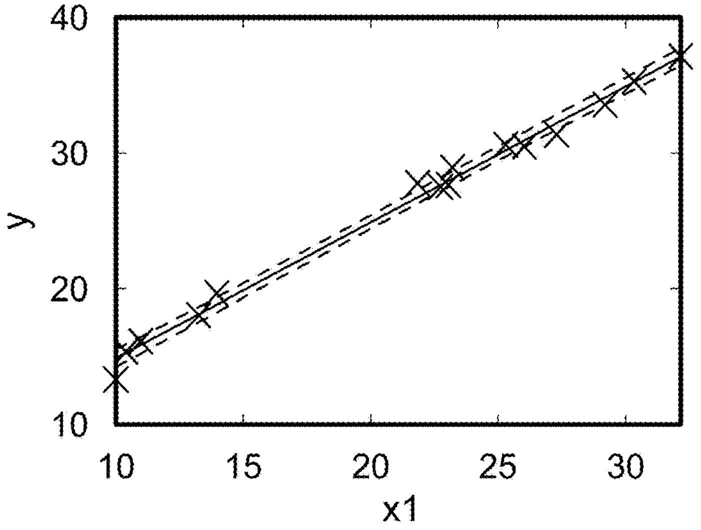
Figure 15F:
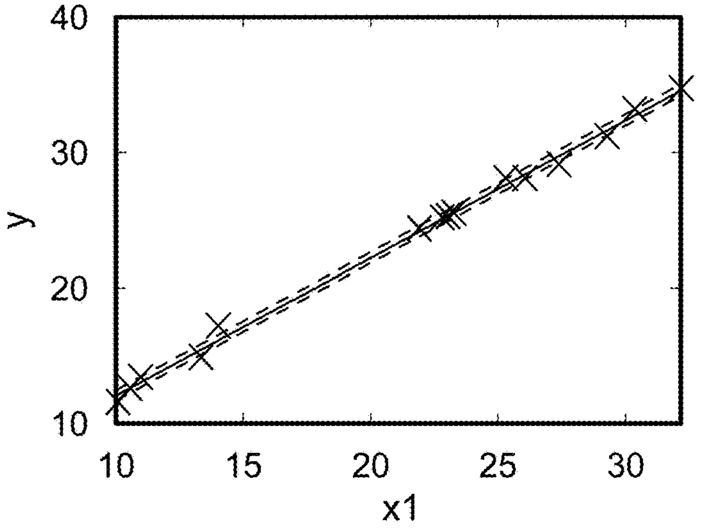
Figure 15G:
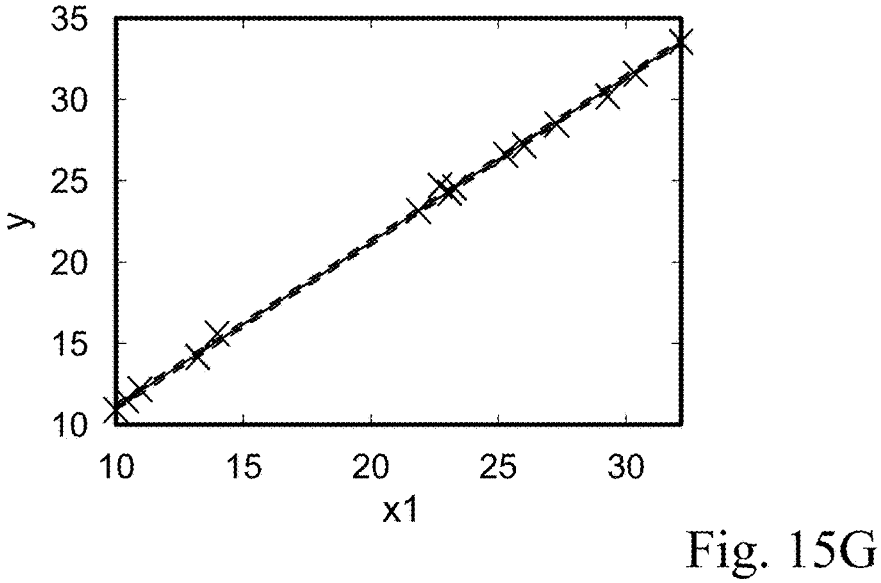
Figure 15H:
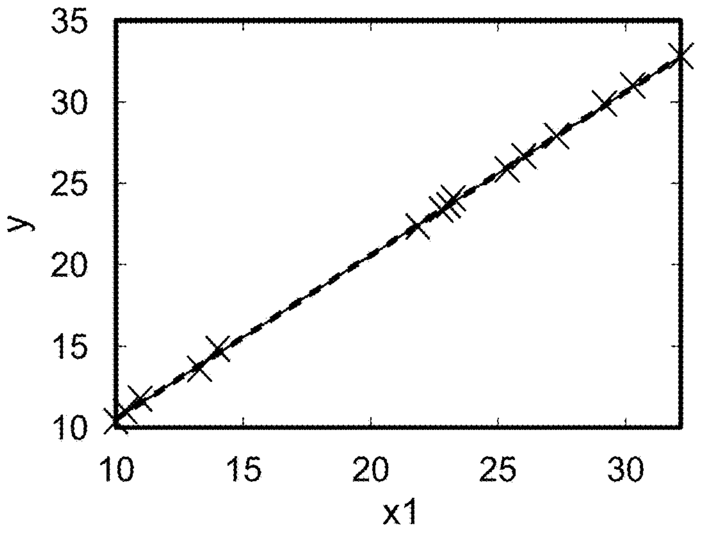
Figure 15I:
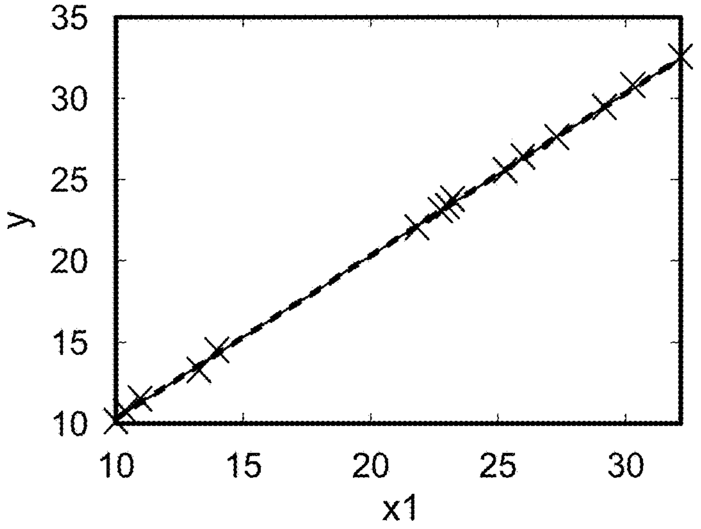
Figure 15J:
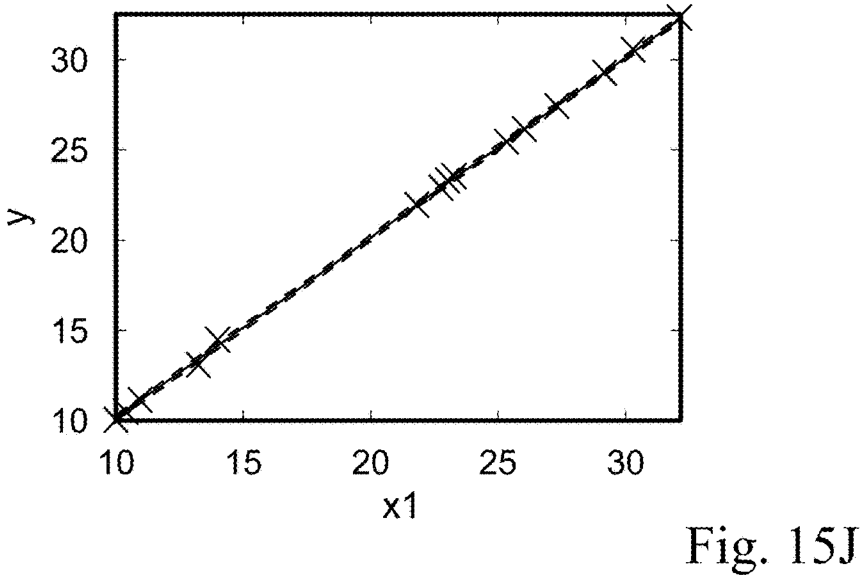

The selection of the lower and upper thresholds for $d_b$ can be justified by inspecting measurement linearity compared to the baseline (FIG. 13) and via a Pearson correlation test (FIG. 14) and subsequent linear regression (FIG. 15). According to the 1:1 control lines in all three panels of FIG. 13 that correspond to each tested field, the saturation is notable in the measurements when the sensor is less than 40 cm away from the robot's body; obtained values for 30 cm and below clearly: deviate from the other cases, while obtained values of 70 cm are getting closely clustered together and approaching the 1:1 control line. The case of $d_b$=40 cm appears to be the switching point. While it could be argued based on Table I and FIG. 13 that this case demonstrates high differentiation from the baseline (especially at the bare field), the Pearson correlation test (FIG. 14A) yields a value of 0.98 for the distance of 40 cm, which approximates the value of 1 and thus can be considered as a constant linear offset. Slopes and linear regression results also provide additional supporting evidence for picking $d_b$=40 cm as the lower threshold for further analysis. It can also be readily verified that there are no significant differences from setting the probe further than 70 cm away from the robot body, as obtained values appear to have stabilized very close to the respective baseline measurement, in all three fields. Considering that the further we place the probe the worse its terrain traversability capacity (see below), $d_b$=70 cm is an appropriate upper threshold for further analysis. Finally, FIG. 14D shows the intercept coefficient decrease as the probe distance increases which corroborates all previous observations.

Keeping the sensor at a certain distance and farther from the robot's body frame leads to a decrease of the included noise in the conductivity measurements because of electromagnetic interference and increases the linearity of the given readings with respect to the reference (handheld) measurements is validated. As such, we select the fixed distances of $d_b \in \{40, 50, 60, 70\}$ cm to further evaluate the robot's traversability capacity and thus help select the optimal one. Note that the case of 10 cm has significant interference and widely varied values (at cases even negative as shown in Table I) and is henceforth not shown in these graphs to improve visual clarity of the figure.

B. Evaluation of Robot Platform Maneuverability Though Gazebo Simulation

With the set of candidate sensor-to-body distance values being identified ($d_b \in \{40, 50, 60, 70\}$ cm), the next step is to examine the robot's ability to move over various uneven terrain fields while carrying the probe without the probe colliding with the ground as the robot negotiates dips and bumps. In general, each platform configuration may have a distinct effect on the robot's traversability capacity, sensor stability, and thus sensor readings. In an effort to make this process scalable and generalizable, a realistic simulation environment and test robot traversability and probe oscillations for different sensor placement configurations over varied sets of emulated terrains is developed.

Figure 16A:
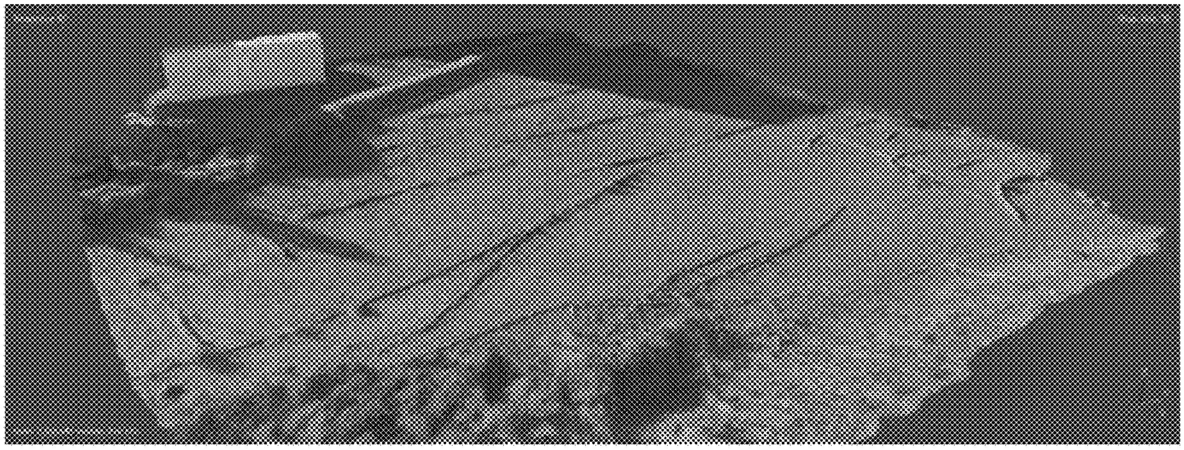
FIG. 16A and FIG. 16B: Instances of the simulated environment created in this disclosure. (A) Final 3D mesh in the Agisoft Metashape software. (B) The simulated Jackal robot equipped with the designed sensor platform spawned in the simulated environment.
Figure 16B:
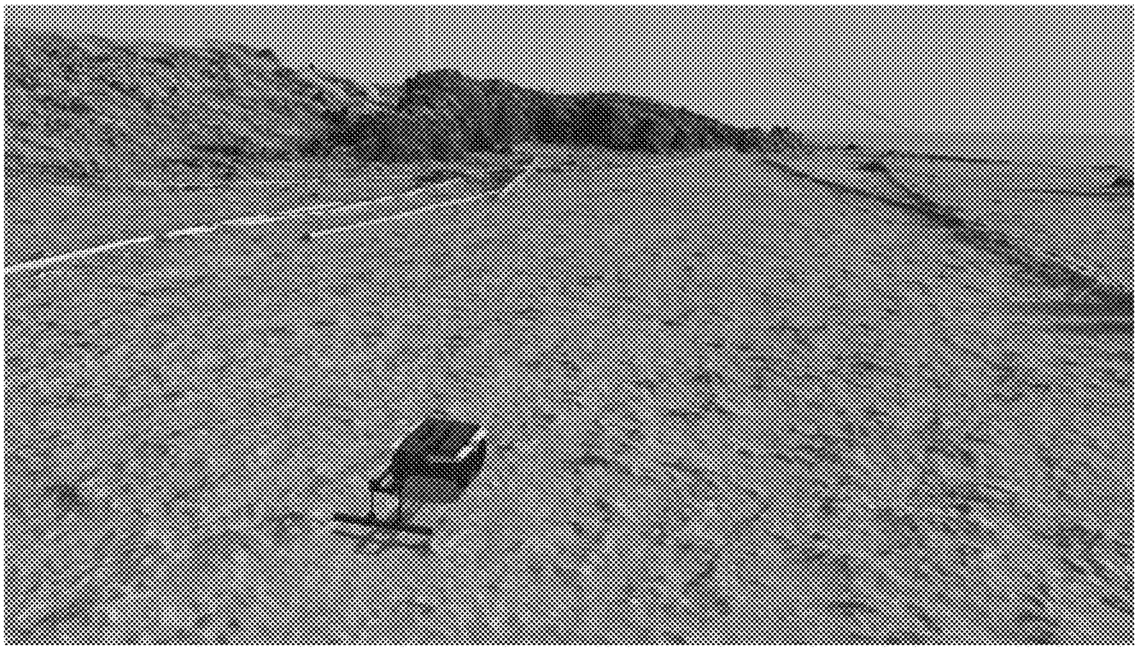

Experimental Procedure: While employing the Gazebo Robotics simulator three key steps were considered: 1) generation of 3D model maps based on aerial imagery, 2) generation of the robot and sensor models, and 3) set up of the simulated experiments and measured variables. The first step allows for the generation of a realistic emulated environment based on real imagery data. The photogrammetric software Agisoft Metashape was used to create a 3D world model based on aerial imagery data that were captured just south of the Center for Environmental Research & Technology (CERT) at the University of California, Riverside (33 59'59.563267" N, −117 20'5.769141" E). By using 97 aerial photos obtained from different positions above the CERT field, photo alignment and stitching was applied through the Agisoft Metashape libraries and generated a colored pointcloud of 25904 points. In addition, by enhancing the sparse pointcloud with more correspondences from the stitching process, a dense pointcloud was generated containing ≅9 million points; the latter was then transformed into a 3D mesh model by applying point interpolation. FIG. 16A shows the final form of the 3D mesh of the generated world, inside the Agisoft Metashape interface, and FIG. 16B depicts the integration of the world into the Gazebo simulator along with the simulated real-scale robot.

Figure 17A:
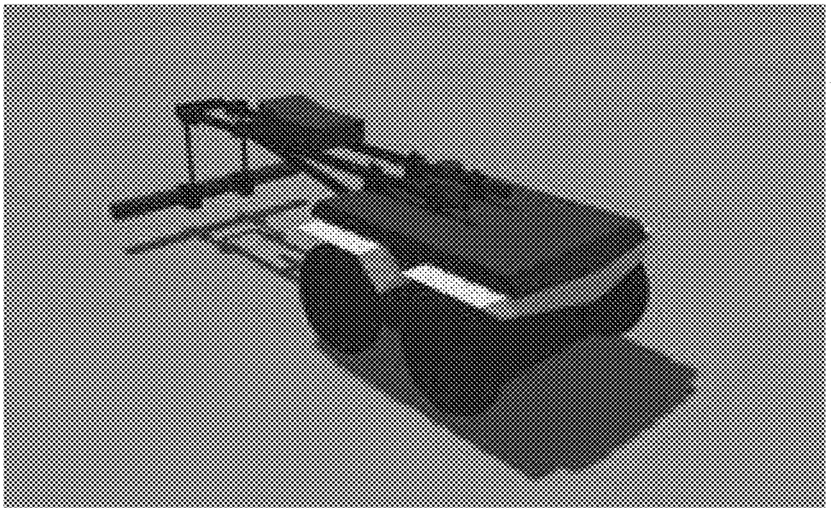
FIG. 17A, FIG. 17B and FIG. 17C: (A) Detailed view on the simulated robot with the sensor mounted. (B) Generated 3D models of the EMI platform in the configuration. (C) Time series chart of level deviations of the sensor during its random roam in the simulated environment.
Figure 17B:
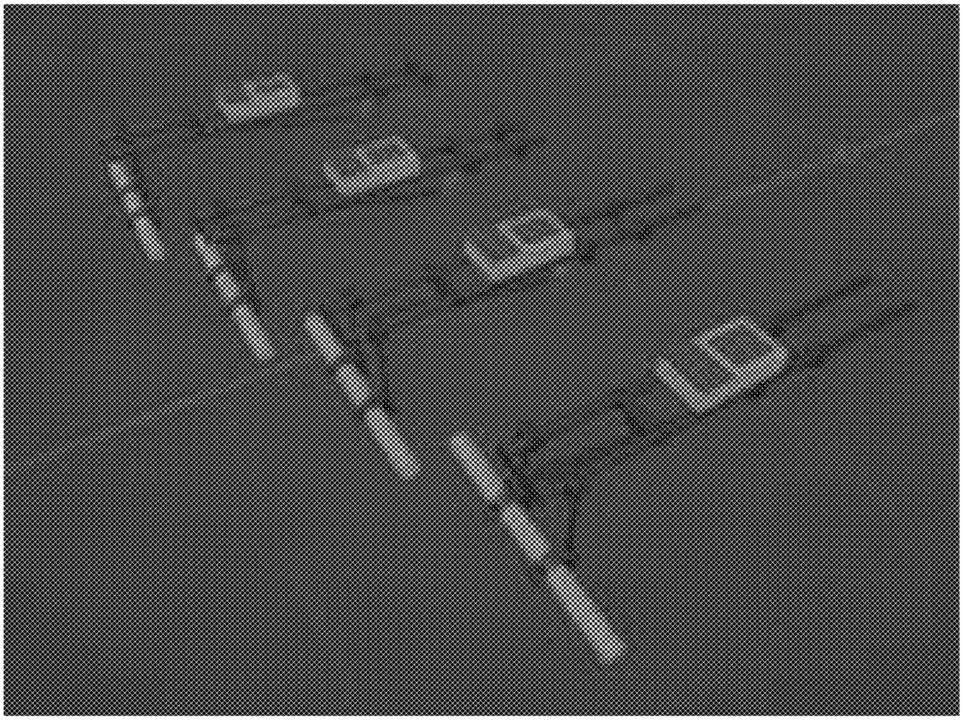
Figure 17C:
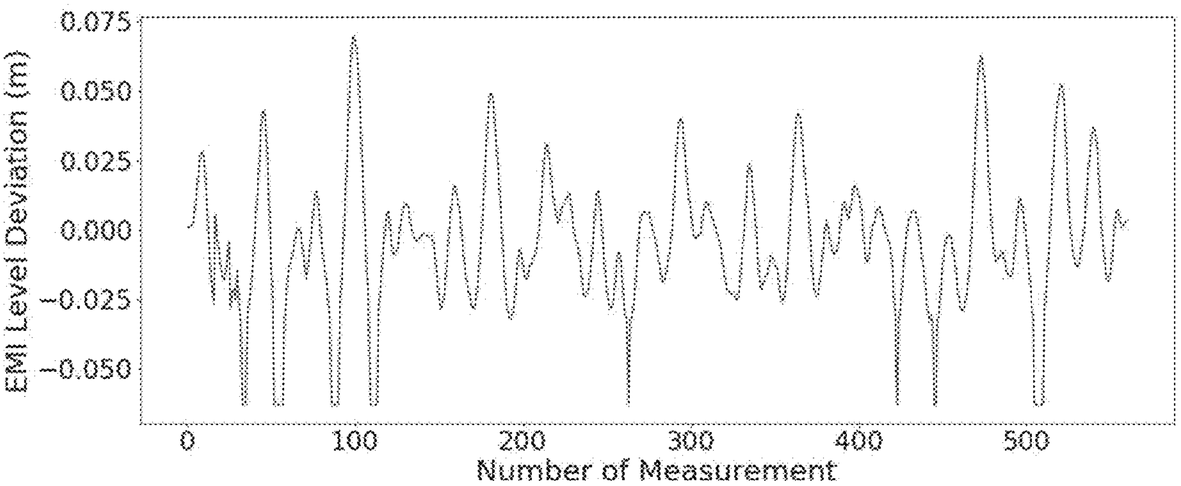

A Gazebo model for the Clearpath Robotics Jackal robot employed herein is already publically available. A custom Gazebo model was developed for the GF CMD-Tiny sensor and integrated into the main robot model. FIG. 17 depicts these models. Four separate Gazebo models of the sensor were generated (FIG. 17B), each corresponding to one of the considered probe distances $d_b \in \{40, 50, 60, 70\}$ cm. The sensor's height off the ground was adjusted to be $d_h \in \{6, 11\}$ cm, which approximates the average height of sensor placement during handheld continuous measurements. The simulated Jackal model weighs 17 kg, similarly to the real one, and the sensor platform with the onboard CMD-Tiny sensor is at 4 kg. To evaluate the GF CMD-Tiny sensor oscillations in the z-axis during the Jackal's movement, a ranging plugin was also developed in Gazebo, to provide continuous information about the distance of the EMI sensor from the ground. The Gazebo plugin publishes continuously the ranges of the sensor body to the ground through a sensor msgs/LaserScan ROS topic, thus allowing us to capture the deviation data in real-time (one such example is shown in FIG. 17C). Note that the simulated setup features the same ROS libraries as the real robot does, and it can be teleoperated or commanded to move to a goal pose (i.e. position and orientation) in the local frame, as it has an integrated RTK-GNSS antenna as well.

Figure 18:
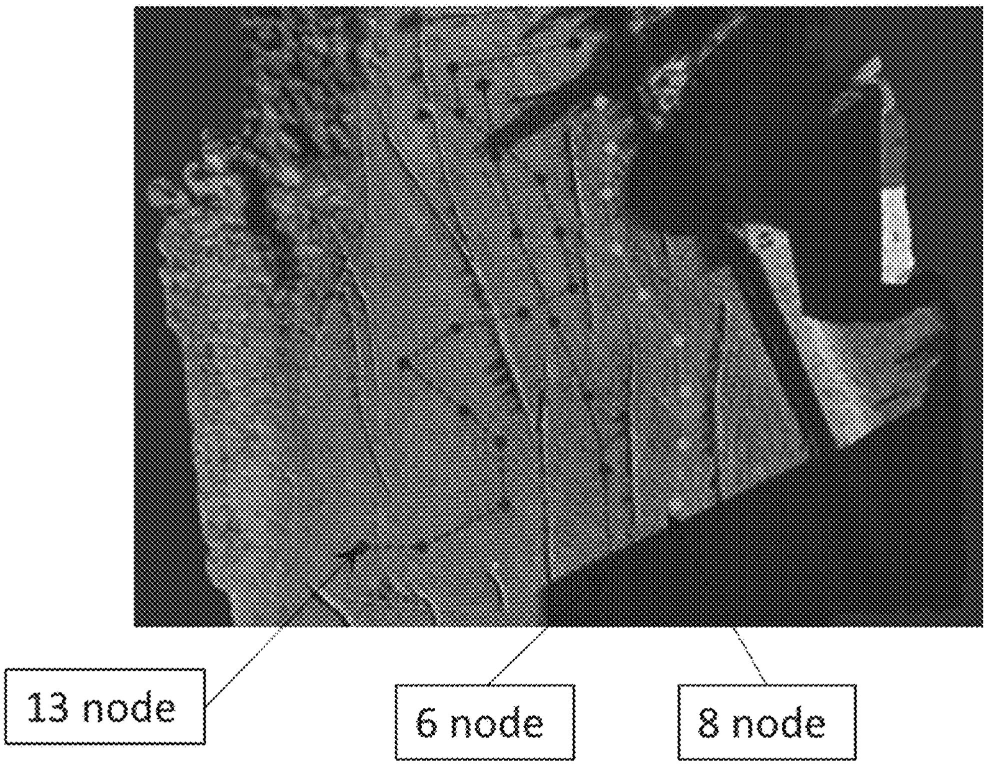
FIG. 18: Planned trajectories for testing robot traversability in the simulated Gazebo world. The blue (6-node) trajectory lies on a smooth region of the map, the green (8-node) is on an uneven/rocky land area of the map, and lastly the red (13-node) contains a longer trajectory over mixed type terrain (best viewed in color).

To evaluate the rigidity and robustness of the designed platform three independent simulated experiments inside the emulated field in the Gazebo world for the selected platform configurations (parameters $d_b$ and $d_h$) were conducted. In these experiments, the Jackal was commanded to follow specific trajectories of different in difficulty terrain types, namely a straight path in a slightly planar area, a straight path in a more rocky area, and a complex path with mixed type terrain (FIG. 18). During the trajectory following, the robot measures the vertical oscillations of the EMI sensor with respect to the ground. Each individual case is repeated for five times, thus giving rise to a total of 120 (simulated) experimental trials in this specific benchmark.

Key Findings: Results of this second experimental benchmark are contained in Table II (Measured sensor oscillations during simulated surveys in the Gazebo environment) below.

TABLE II

Measured Sensor oscillations during simulated surveys in the Gazebo environment

| | Smooth Land | | | Rocky Land | | | Mixed-terrain Land | | |
|---|---|---|---|---|---|---|---|---|---|
| $d_b$-$d_h$ | Mean (cm) | σ (cm) | Variance (cm$^2$) | Mean (cm) | σ (cm) | Variance (cm$^2$) | Mean (cm) | σ (cm) | Variance (cm$^2$) |
| 40 cm-6 cm | −0.50 | 2.57 | 6.61e−02 | −0.51 | 3.15 | 9.94e−02 | −0.54 | 2.58 | 6.65e−02 |
| 50 cm-6 cm | −0.60 | 3.13 | 9.81e−02 | −0.52 | 3.13 | 9.97e−02 | −0.68 | 2.80 | 7.83e−02 |
| 60 cm-6 cm | −0.83 | 2.97 | 8.81e−02 | −0.49 | 3.24 | 0.10 | −0.79 | 3.02 | 9.10e−02 |
| 70 cm-6 cm | 0.68 | 4.11 | 0.17 | −0.61 | 3.91 | 0.15 | −0.71 | 3.20 | 0.1 |
| 40 cm-11 cm | −0.84 | 2.97 | 8.83e−02 | −0.78 | 3.37 | 0.11 | −1.03 | 3.35 | 0.11 |
| 50 cm-11 cm | −1.12 | 3.39 | 0.11 | −1.03 | 4.07 | 0.17 | −1.25 | 3.66 | 0.13 |
| 60 cm-11 cm | −1.47 | 4.37 | 0.19 | −0.93 | 3.94 | 0.16 | −1.57 | 4.47 | 0.20 |
| 70 cm-11 cm | −1.23 | 3.69 | 0.14 | −1.62 | 4.76 | 0.23 | −1.50 | 4.04 | 0.16 |

First, note that the increase of the sensor distance relative to the robot body makes the robot less stable and in turn leads to increased probe oscillations when traversing uneven terrain. However, it turns out that the cases of $d_h$={50, 60} cm lead to very similar platform oscillations in terms of reported variance, which in fact are close to the shortest case of 40 cm and more steady compared to the longest 70 cm case. In more detail, and with reference to Table II, the increase of the distance in the probe placement results in increased mean and variance of position deviations while moving, for both tested sensor height off the ground. Mounting the sensor closer to the robot's body and by keeping a shorter robot-sensor footprint, the robot is more stable in either smoother or more rough terrain types. For the $d_h$=6 cm case, placing the sensor at $d_b$={50, 60} cm achieves similar results by keeping ≅1 cm of difference in standard deviation of the 70 cm case. Also, even though 40 cm is the less shaky solution overall, the cases of $d_b$={50, 60} cm have less than ≅0.5 cm difference in standard deviation. Additionally, by comparing across experiments, the 50 cm case appears to score less than $10^{-4}$ $m^2$ of variance. These observations are consistent also in the case of $d_h$=11 cm, by having the smallest sensor displacement when $d_b$=40 cm and with the cases of $d_b$={50, 60} cm performing equivalently. Based on these observations, the cases of setting $d_b$={50, 60} cm may offer the best trade-off in terms of noise and steadiness compared with the shorter 40 cm case, in which the probe is placed close to the robot's chassis and is affected more by the electromagnetic interference as shown in Section III. A second observation from these results concerns the sensor's height off the ground, $d_h$. Inspection of the results for different sensor height values $d_h$ in Table II, we notice a similar oscillating behavior, whereby a shorter height (i.e. $d_h$=6 cm) might be preferred to reduce variations from the ground. This becomes even more critical considering that, during real surveys, it is hard for a farm worker that uses the handheld sensor to keep the sensor consistently at a stable height off the ground while walking. For these reasons $d_h$=6 cm is used.

C. Preliminary Feasibility Experimental Testing of Boundary Configurations

The last set of calibration tests for optimal sensor placement included validation of the preliminary feasibility of the robot-sensor setup to measure ECa continuously. Based on the aforementioned results, these validation experiments for the two boundary cases of probe distance (i.e. $d_b$={40, 70} cm), at a constant height of $d_h$=6 cm were studied. This approach provided a better understanding of the effects of placing the sensor closer or further away from the robot on continuous ECa measurements.

Figure 19A:
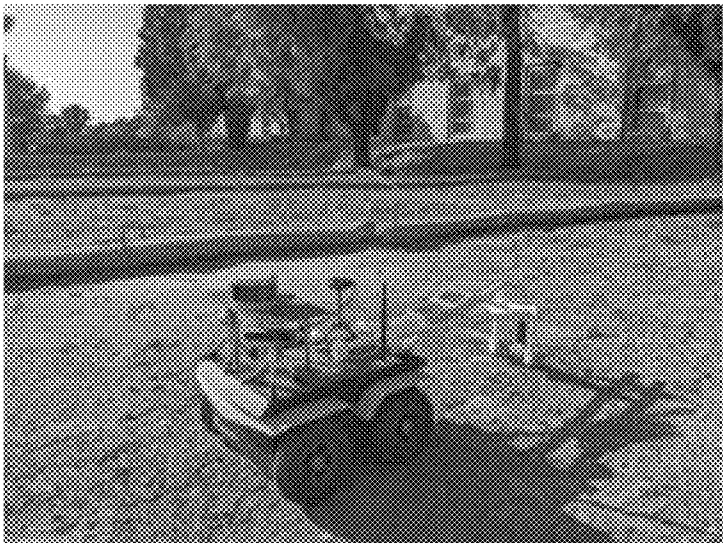
FIG. 19A, FIG. 19B and FIG. 19(C): (A) The Jackal robot equipped with the platform holding the CMD-Tiny instrument at the configuration of $d_b$=50 cm and $d_h$=6 cm. (B) Instance of robot during the soil ECa data collection for validation. (C) Validation testing considered two distinctive trajectories, one following a straight line and another performing a U-shaped curve.
Figure 19B:
Figure 19C:
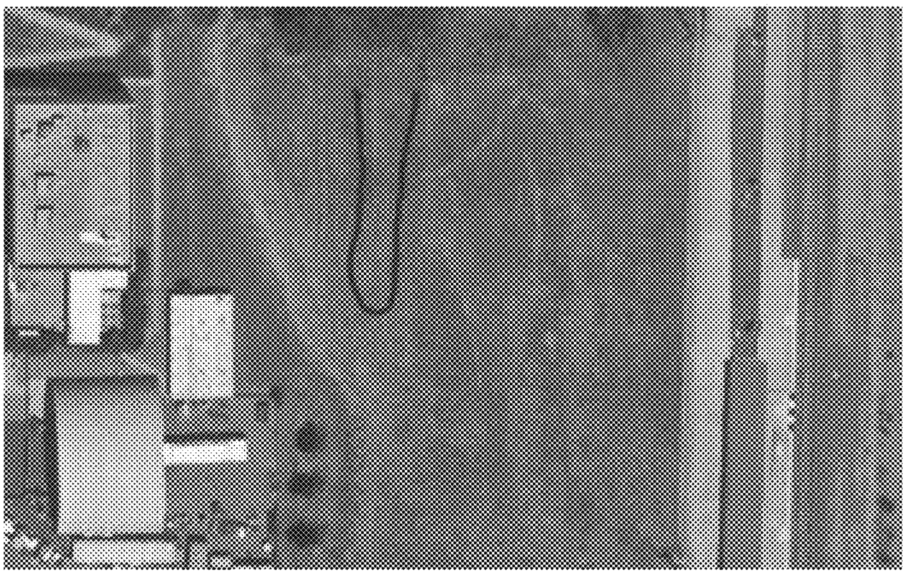

Experimental Procedure: The validation experiments took place in the same field that was emulated for the aforementioned simulation testing. Without loss of generality, two distinct cases: 1) a straight-line trajectory with $d_b$=70 cm and $d_h$=6 cm, and 2) a U-shaped trajectory with $d_b$=40 cm and $d_h$=6 cm were considered. In each case we conducted three independent trials. The starting and end positions as well as intermediate waypoints were the same for each set of trials. The physical setup, experimental field, and the two types of trajectories are depicted in FIG. 19. Manual data collections with the handheld sensor (three for each trajectory type) were also performed to serve as the baseline. In total, 12 experimental trials were considered for validation in the bare field (six robotized and six manual). Obtained soil ECa measurements were georeferenced via RTK-GNSS in the robotized measurement and the sensor's embedded GPS in the manual measurements. Collected soil ECa data were used to generate a custom raster of the surveyed area; then kriging interpolation through exponential semivariogram was used to obtain the ECa map which was embedded onto satellite imagery via the ESRI ArcGIS 10.8.2 software.

Figure 20A:
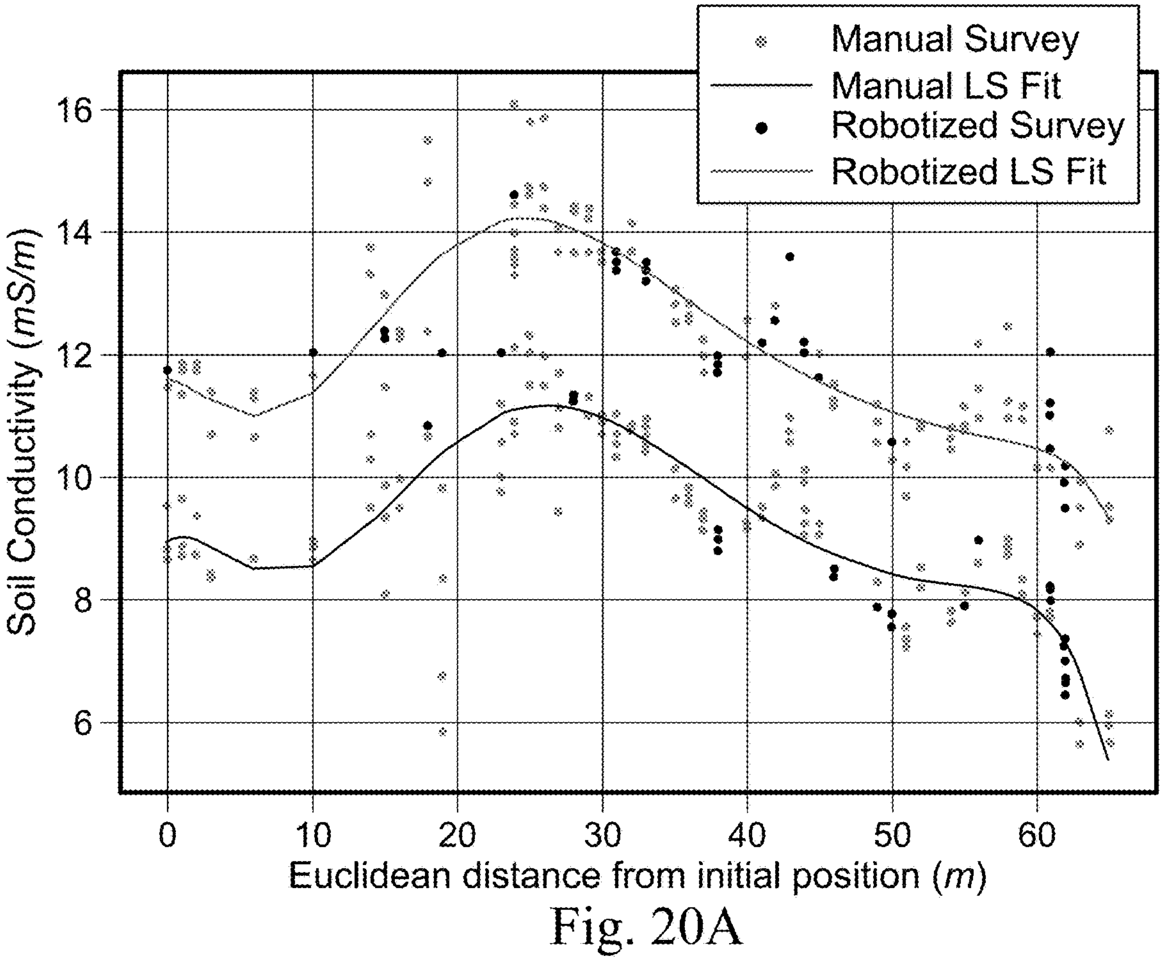
FIG. 20A, FIG. 20B, and FIG. 20C: (A) The soil conductivity curves of the straight-line trajectory case in the bare field. Fitted graphs of both measurement curves correspond to an 8th grade least squares fit. (B)-(C) Soil ECa maps corresponding to manually-collected (handheld) and robotized-collected data, respectively, computed by applying kriging interpolation through exponential semivariogram. Each panel also contains the value-based color scale, the map statistics, and the histogram of the conductivity values.
Figure 20B:
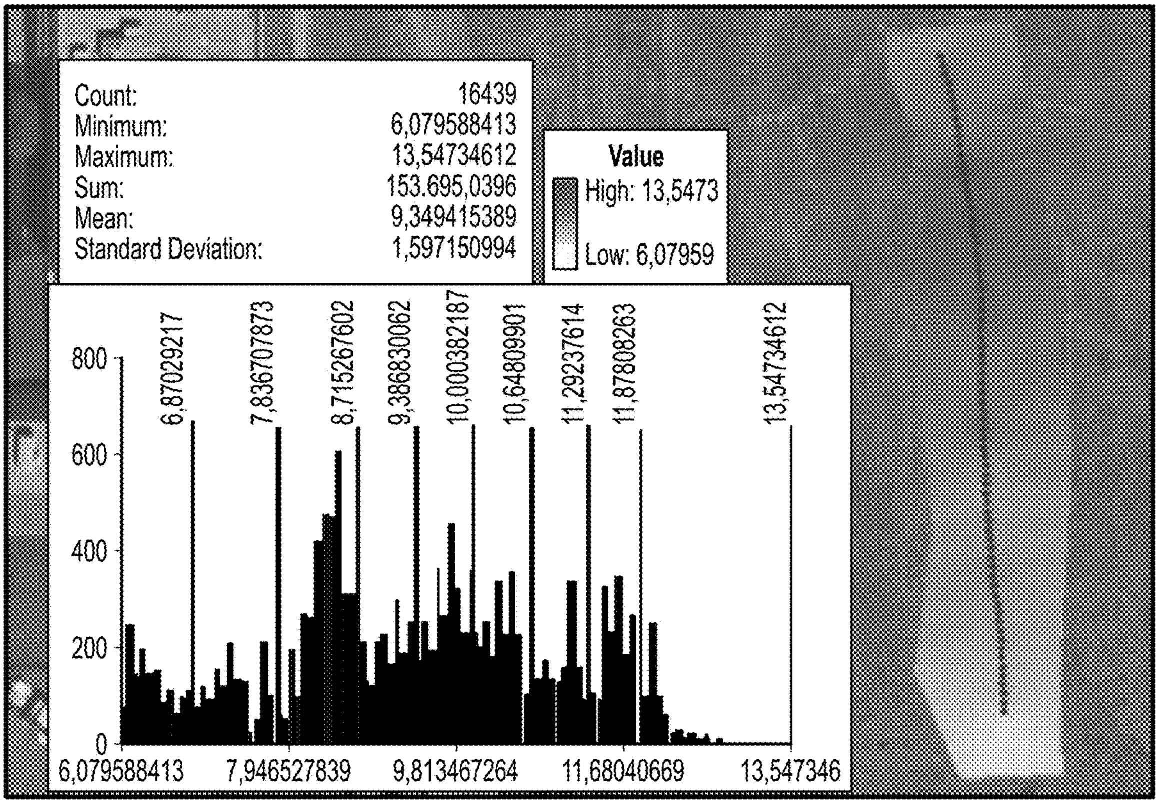
Figure 20C:
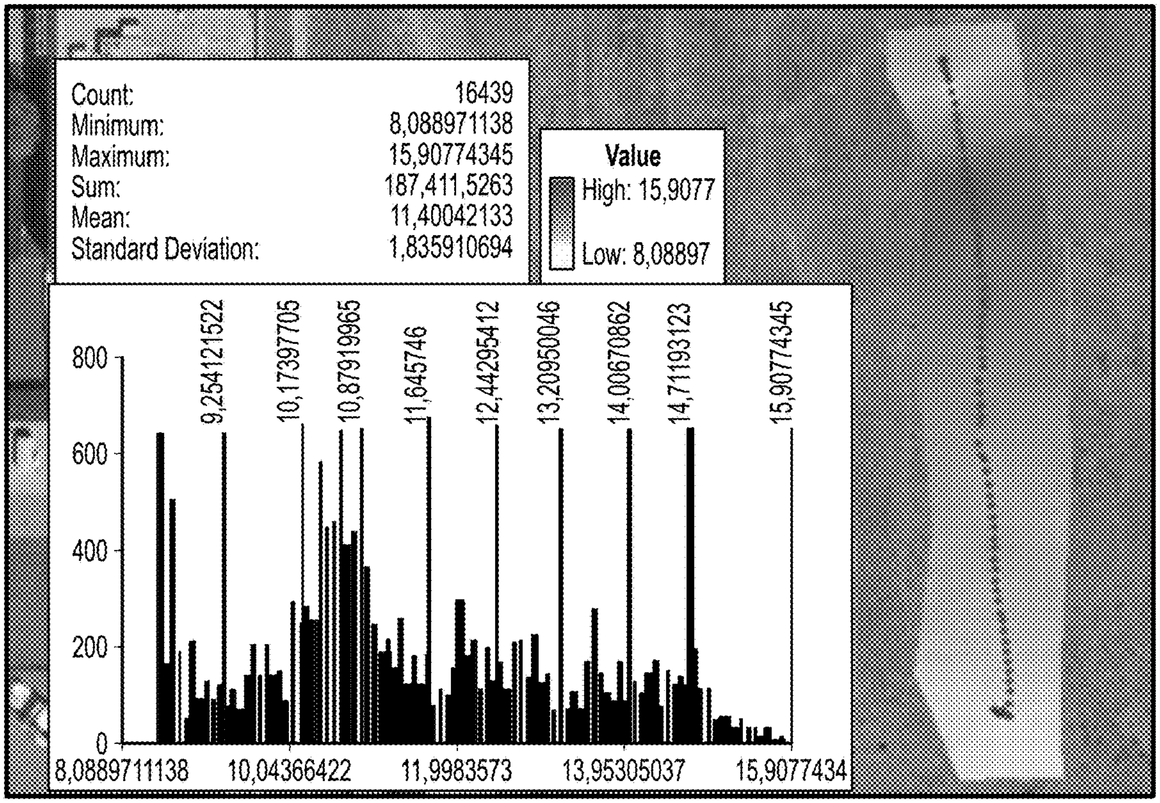
Figure 21A:
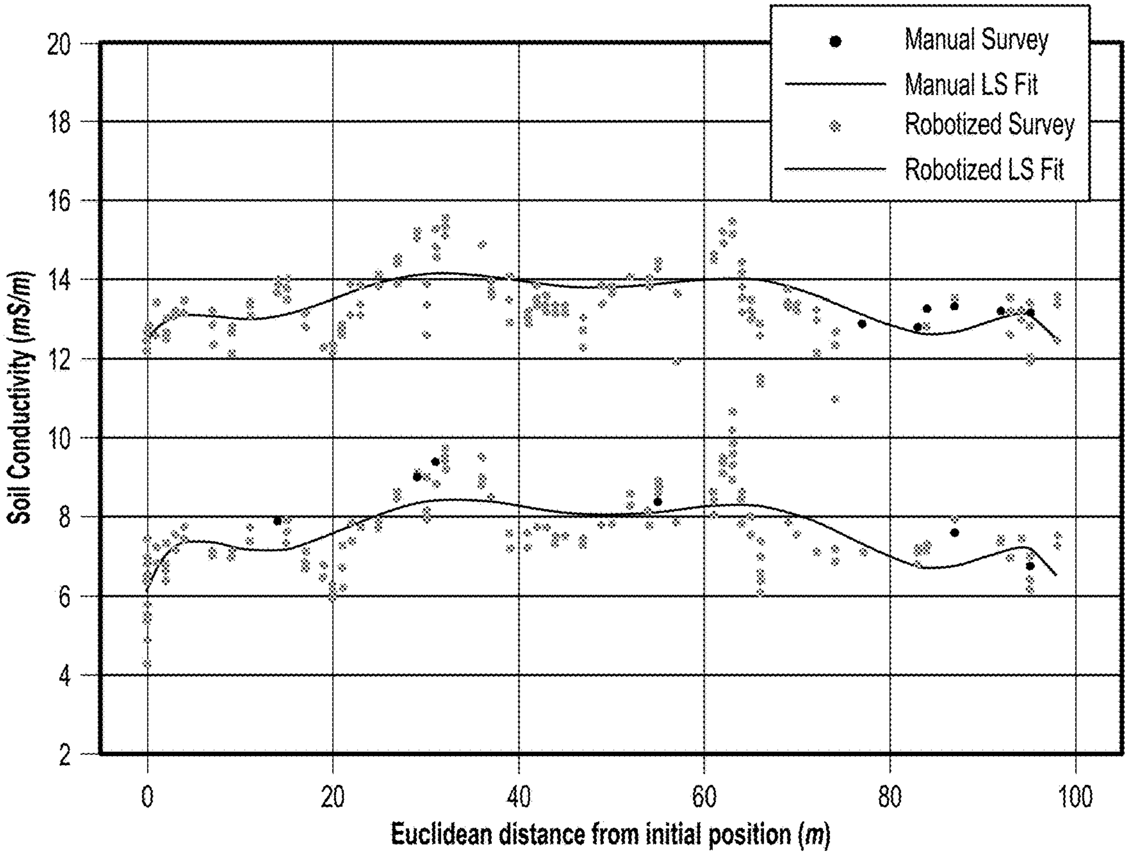
FIG. 21A, FIG. 21B, and FIG. 21C: (A) The soil conductivity curves of the U-shaped trajectory case in the bare field. Fitted graphs of both measurement curves correspond to an 8th grade least squares fit. (B)-(C) Soil ECa maps corresponding to manually-collected (handheld) and robotized-collected data, respectively, computed by applying kriging interpolation through exponential semivariogram. Each panel also contains the value-based color scale, the map statistics, and the histogram of the conductivity values.
Figure 21B:
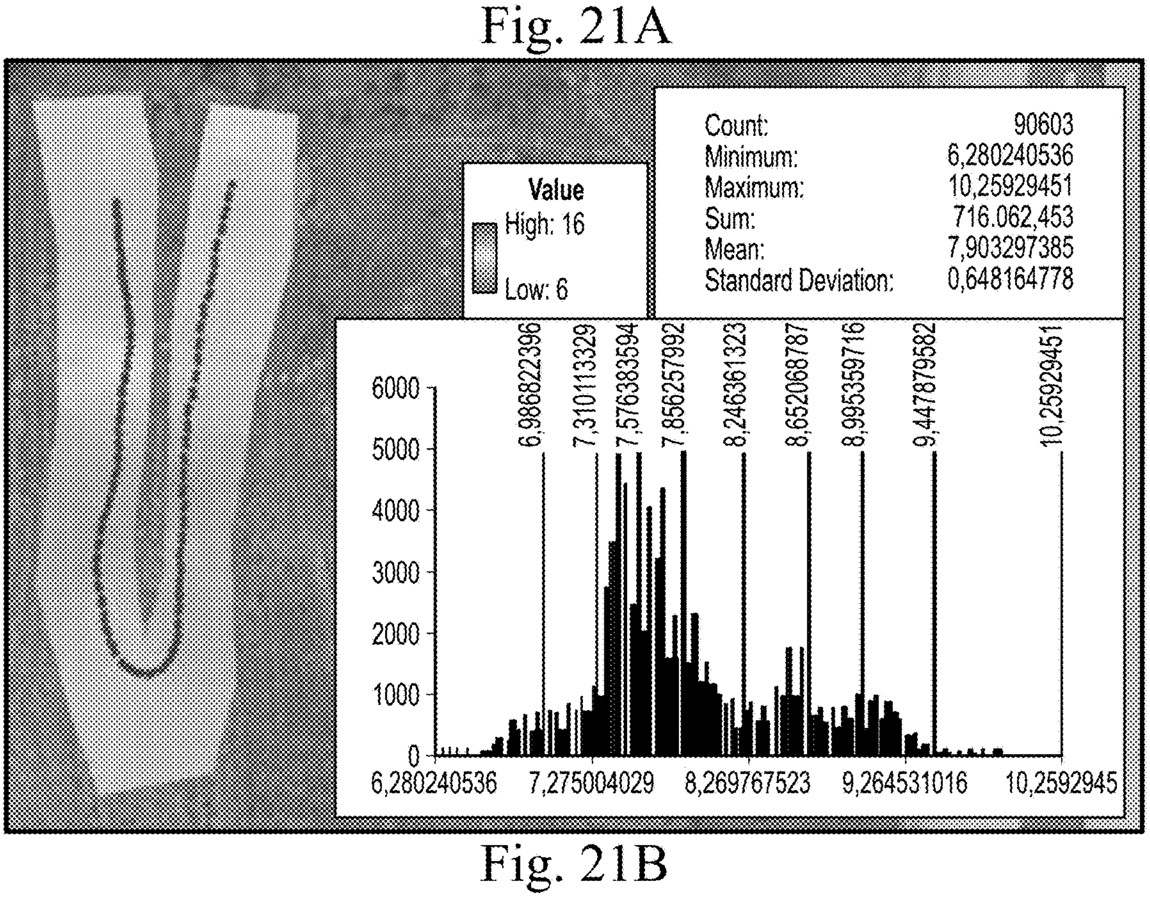
Figure 21C:
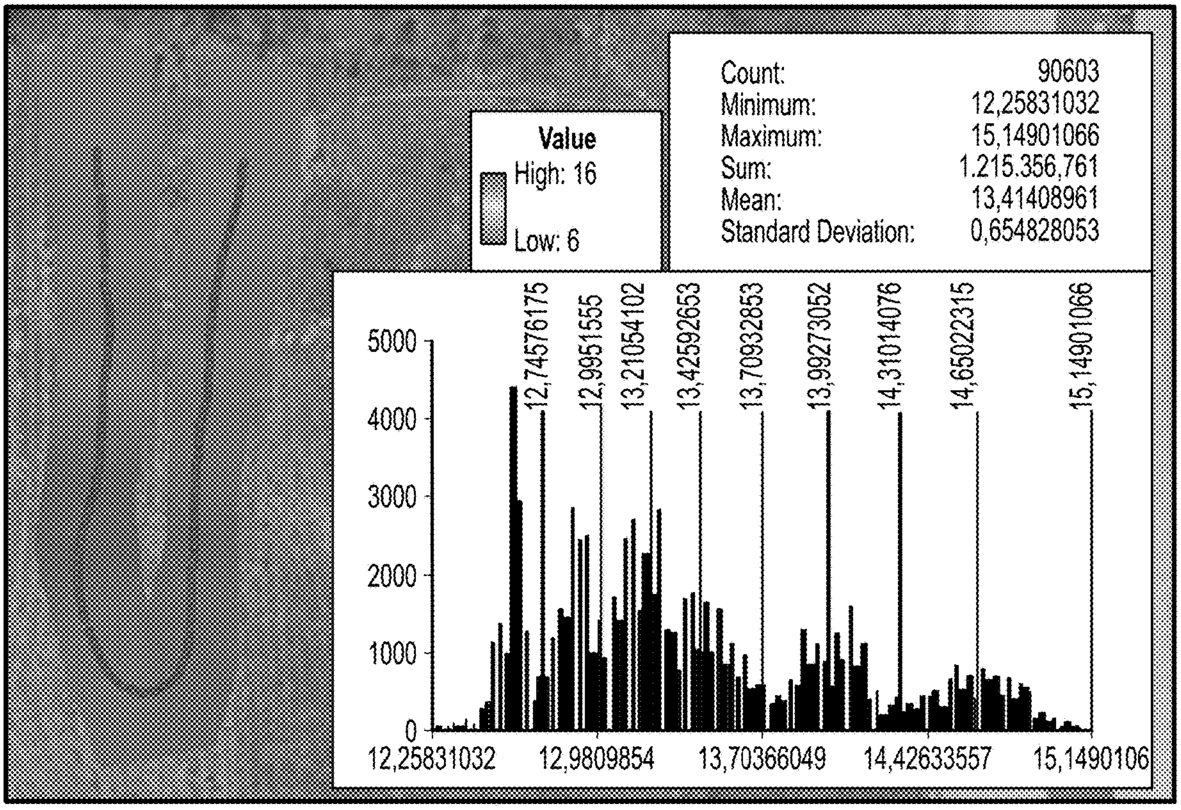

Key Findings: Obtained results visualized based on aggregated soil conductivity plots and the corresponding ECa maps for the cases of $d_b$=70 cm (straight line trajectory) and $d_b$=40 cm (U-shaped trajectory) are depicted in FIG. 20 and FIG. 21, respectively. Foremost, results validate that the shorter probe distance placement demonstrates a higher difference on average sensor readings compared to the longer distance setting against the manual baseline data (case $d_b$=40 cm, robotized: {μ=13.32, σ=0.99} mS/m and manual: {μ=7.55, σ=0.92} mS/m; case $d_b$=70 cm, robotized: {μ=11.40, σ=1.83} mS/m and manual: {μ=9.34, σ=1.59} mS/m). Despite this increased difference, however, the standard deviations are close between robotized and manual measurements in both cases. This indicates that there is consistency among the two types of measurements, and that the observed offsets in robotized measurements compared to their respective manual baselines can be in fact treated as constant offsets. Further evidence in support of the constant offset presence can be obtained by the Pearson Correlation Coefficient (PCC). In both cases (straight line and U-shape), the robotized ECa measurements showcase high linearity with their manual counterparts. Specifically, by removing outlier measurements that lie out of the $\pm 2\sigma$ measurement distribution, the straight-line trajectory attains a PCC of 0.95 whereas the U-shaped trajectory reaches a PCC of 0.88 (despite significant electromagnetic interference as demonstrated in static tests discussed below), compared with manual measurements that were conducted on exactly the same paths. These findings can be visually corroborated by the obtained ECa maps in panels (B) and (C) of FIG. 20 and FIG. 21, with the main difference being that the color differential in the shorter probe placement case of $d_b$=40 cm (FIG. 21) being more pronounced due to the larger constant offset in measurements compared to the longer probe placement case of $d_b$=70 cm (FIG. 20).

In all, these preliminary feasibility testing validates THAT trustworthy continuous ECa measurements can be performed with the developed robotic setup even at the two boundary configurations. Results verify the system's high linearity with respect to manually-collected (handheld) data, and that the constant additive offset on the overall ECa measurements caused by the robot's electromagnetic interference does not significantly affect the linearity of obtained measurements in the end. Putting everything together, the conclusion is that the configuration $\{d_b$=60 cm, $d_h$=6 cm$\}$ can serve as an appropriate tradeoff that combines lower robot-to-sensor signal interference and higher maneuverability, and it is thus selected as the optimal configuration to conduct field-scale experiments. These are discussed next.

In some embodiments, the configuration $\{d_b$=60 cm, $d_h$=6 cm$\}$ can serve as the substantially optimal one.

Field-Scale Experiments

The analysis helped determine a substantially optimal sensor setup ($\{d_b$=60 cm, $d_h$=6 cm$\}$) for the robot that balances between electromagnetic interference caused by the robot including the robot's electronic components and robot traversability capacity of uneven terrain. The analysis also helped validate the preliminary feasibility of collecting continuous soil ECa measurements over small bare-field areas, with obtained results being trustworthy and consistent to manually-collected baselines. Next, robot-assisted continuous soil ECa measurements over larger fields is described.

Figure 22A:
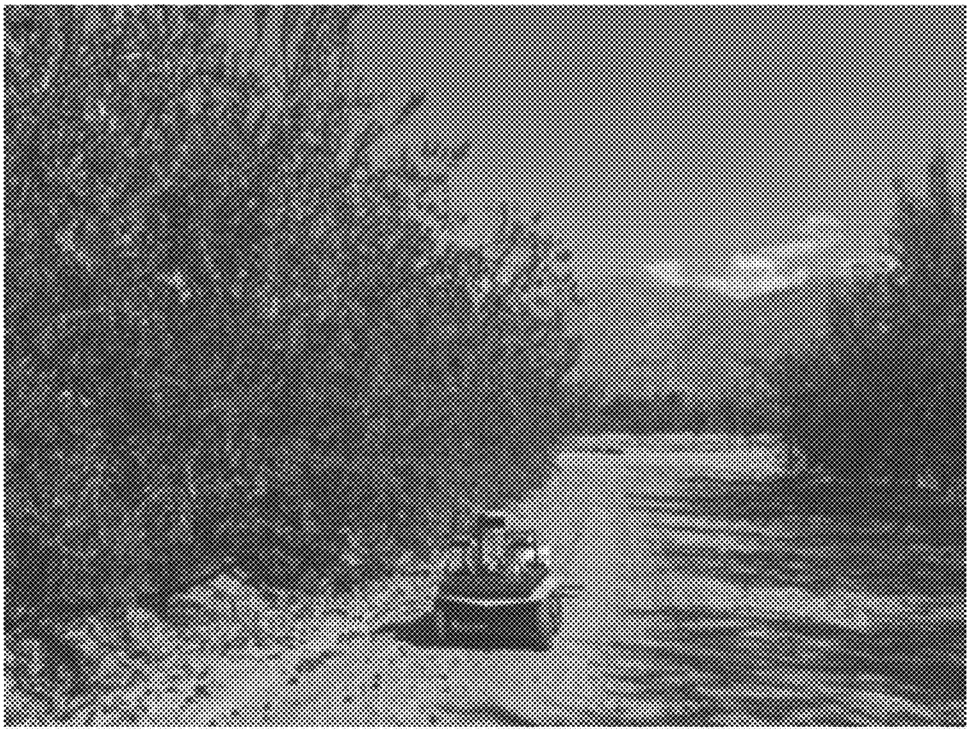
FIG. 22A, FIG. 22B, and FIG. 22C: Field-scale data collections instances: (A) robotized in the olive tree grove and (B)/(C) manual/robotized in the orange tree grove.
Figure 22B:
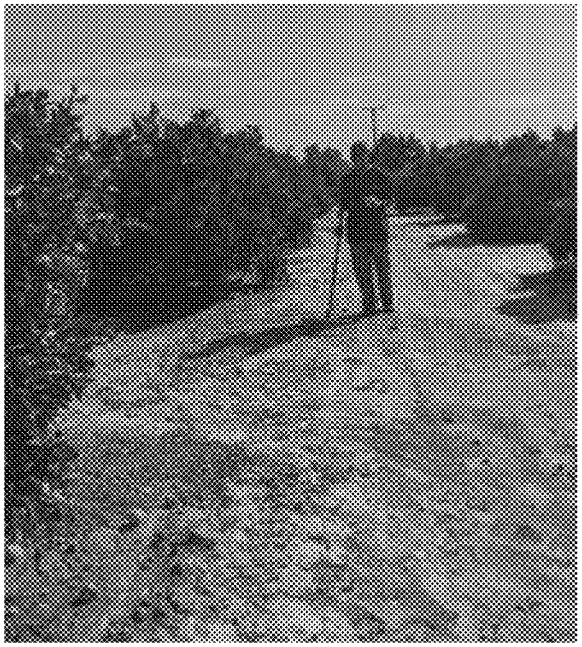
Figure 22C:
Figure 23A:
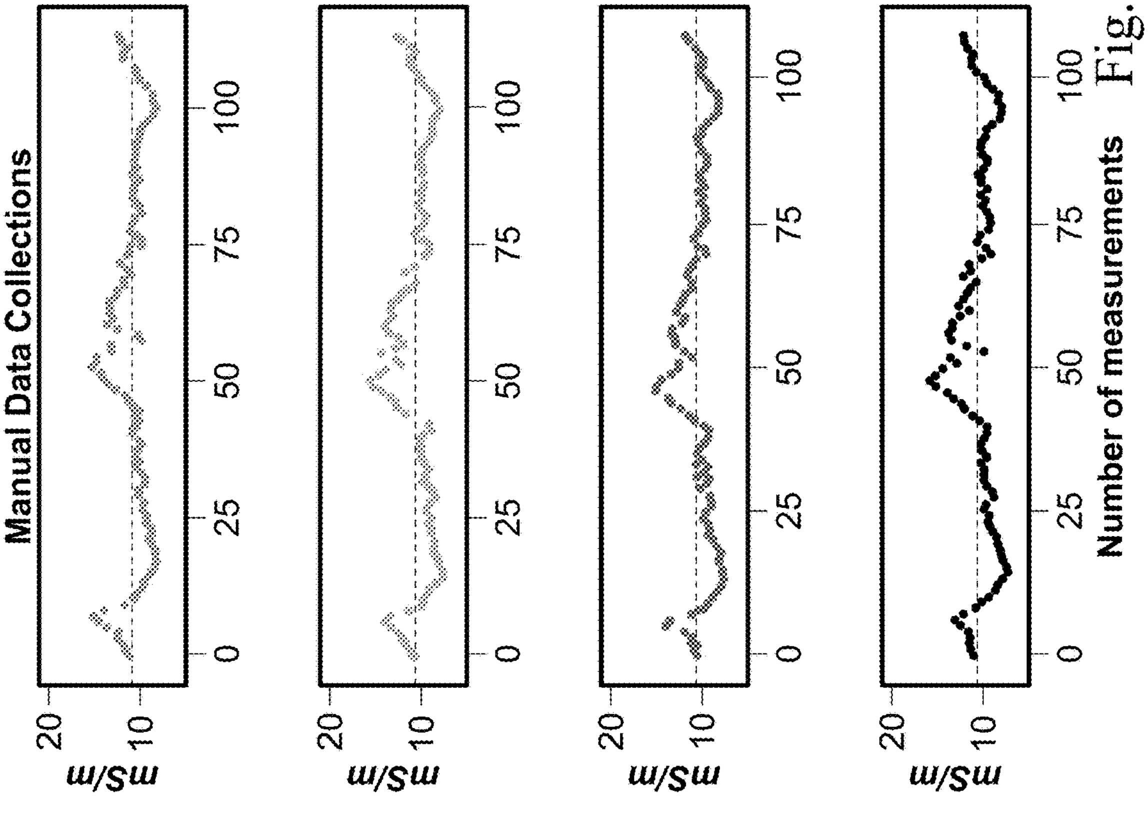
FIG. 23A, FIG. 23B, and FIG. 23C: Olive tree grove case. (A) and (B) Graphs of the raw conductivity measurements by using directly the sensor and via the robot, respectively. (C) Soil conductivity plots of both handheld and robot cases. Fitted plot of both measurement curves is an 8th grade least squares fit.
Figure 23B:
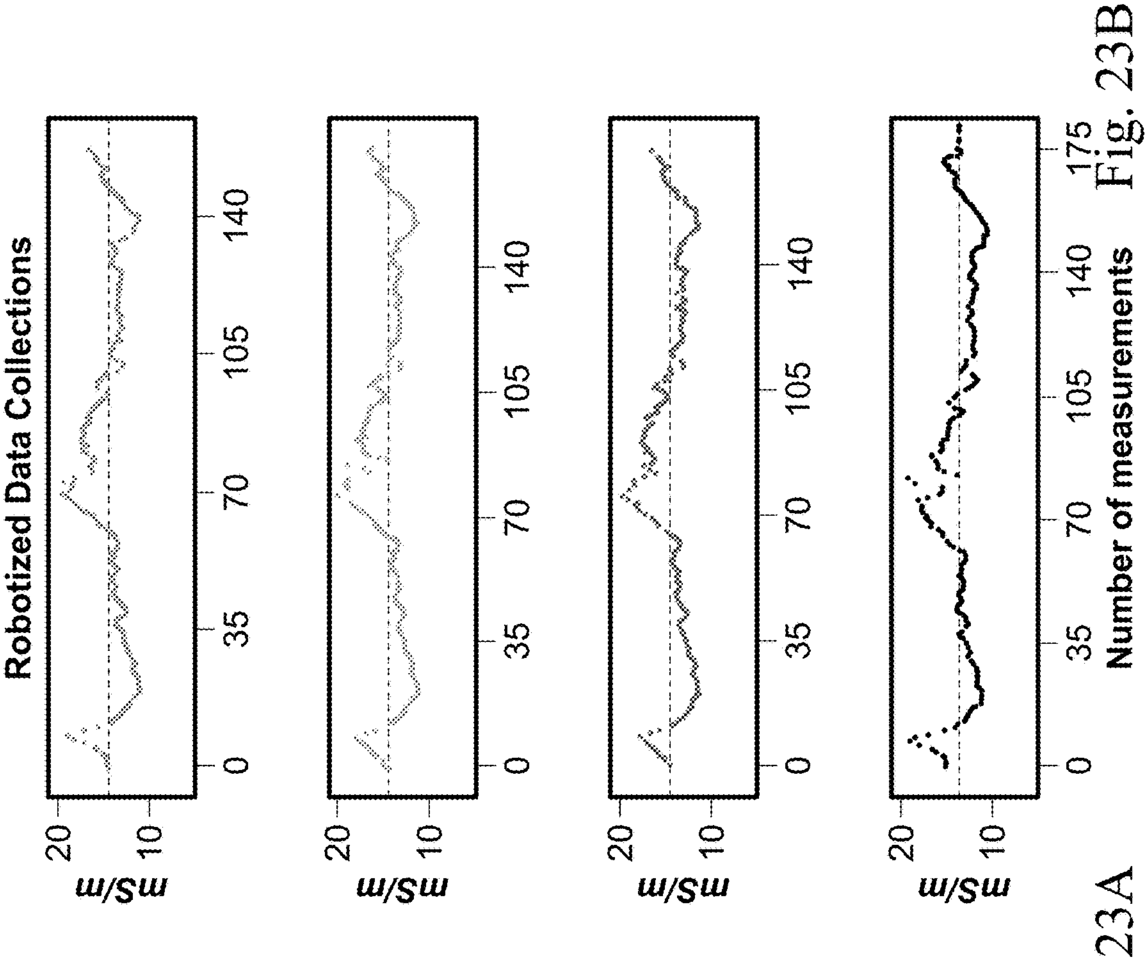
Figure 23C:
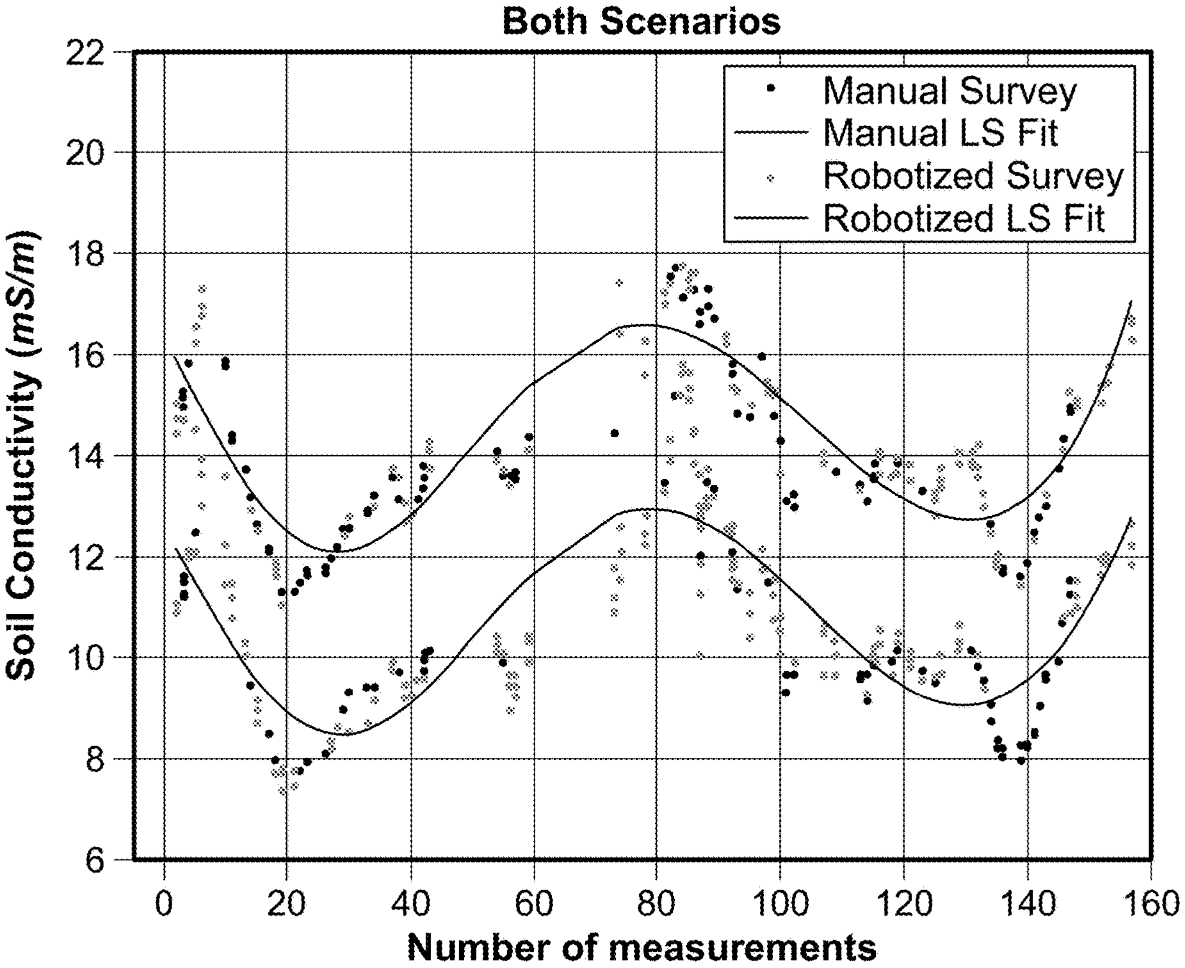
Figure 24A:
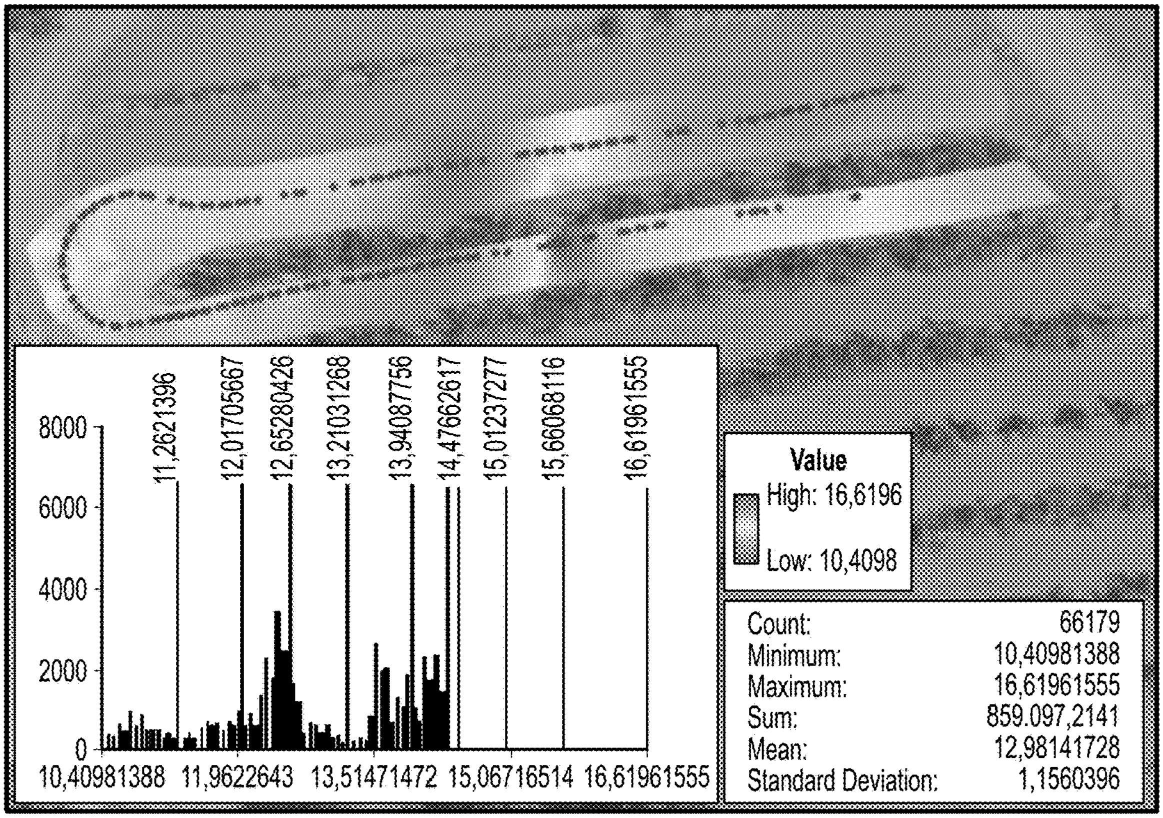
FIG. 24A and FIG. 24B: Obtained soil ECa maps in the olive tree grove for (A) the manual and (B) robotized cases. Maps have been created by applying kriging interpolation through exponential semivariogram. Each map also depicts the value-based color scale, the map statistics, and the histogram of the conductivity values.
Figure 24B:
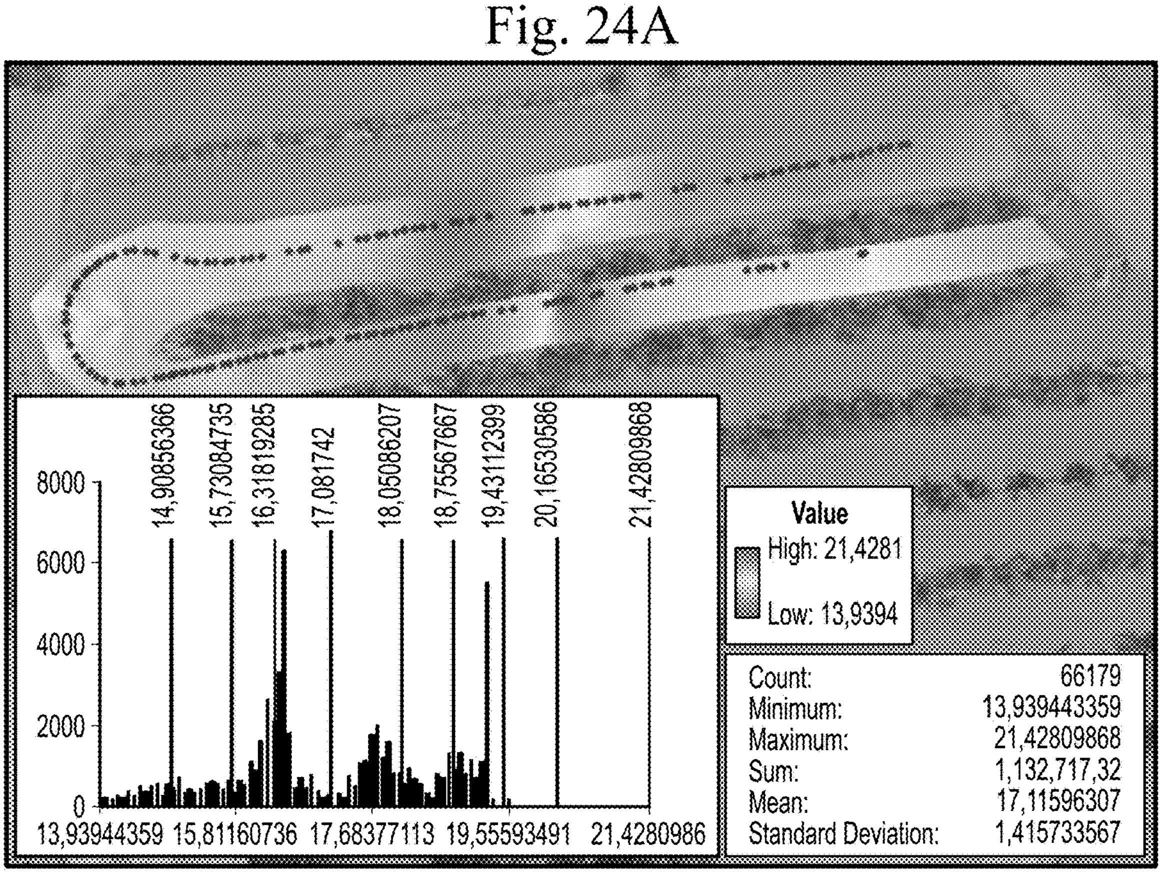
Figure 25A:
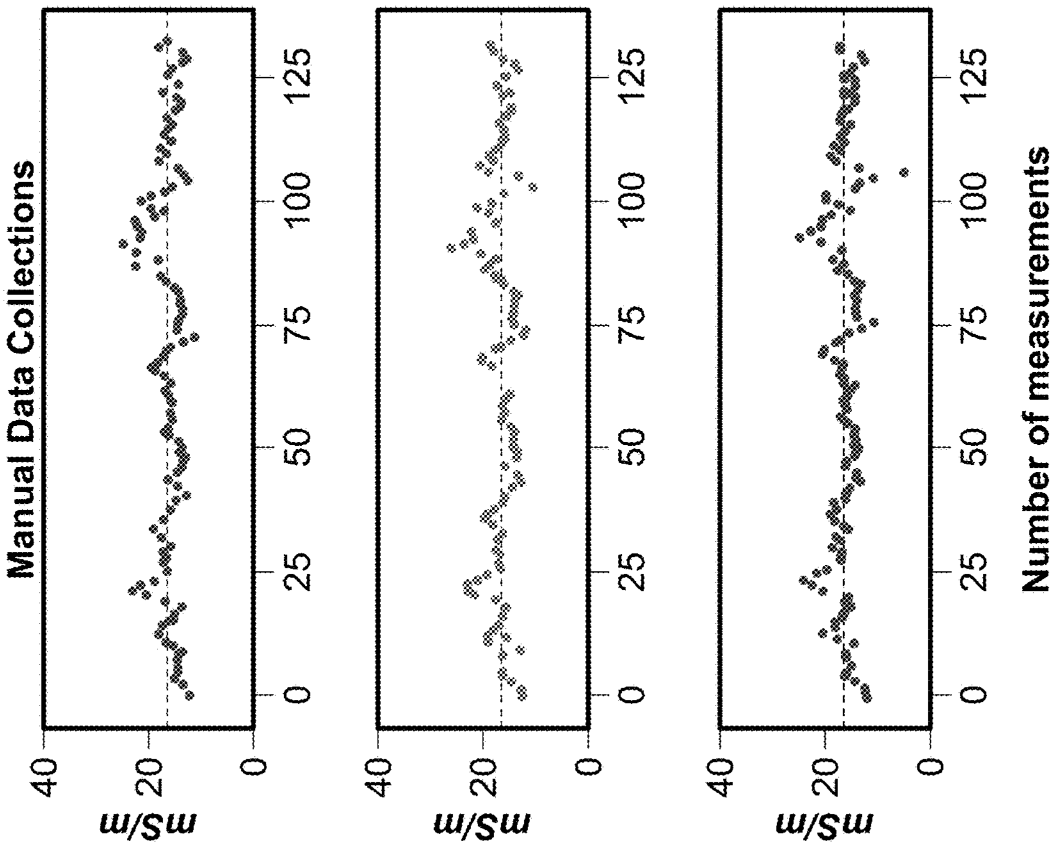
FIG. 25A, FIG. 25B, and FIG. 25C: Citrus tree grove case. (A) and (B) Graphs of the raw conductivity measurements by using directly the sensor and via the robot, respectively. (C) Soil conductivity plots of both handheld and robot cases. The color-shaded areas indicate the filled areas of soil conductivity values of the corresponding manual and robotized measurements. Fitted plot of both measurement curves is an 8th grade least squares fit.
Figure 25B:
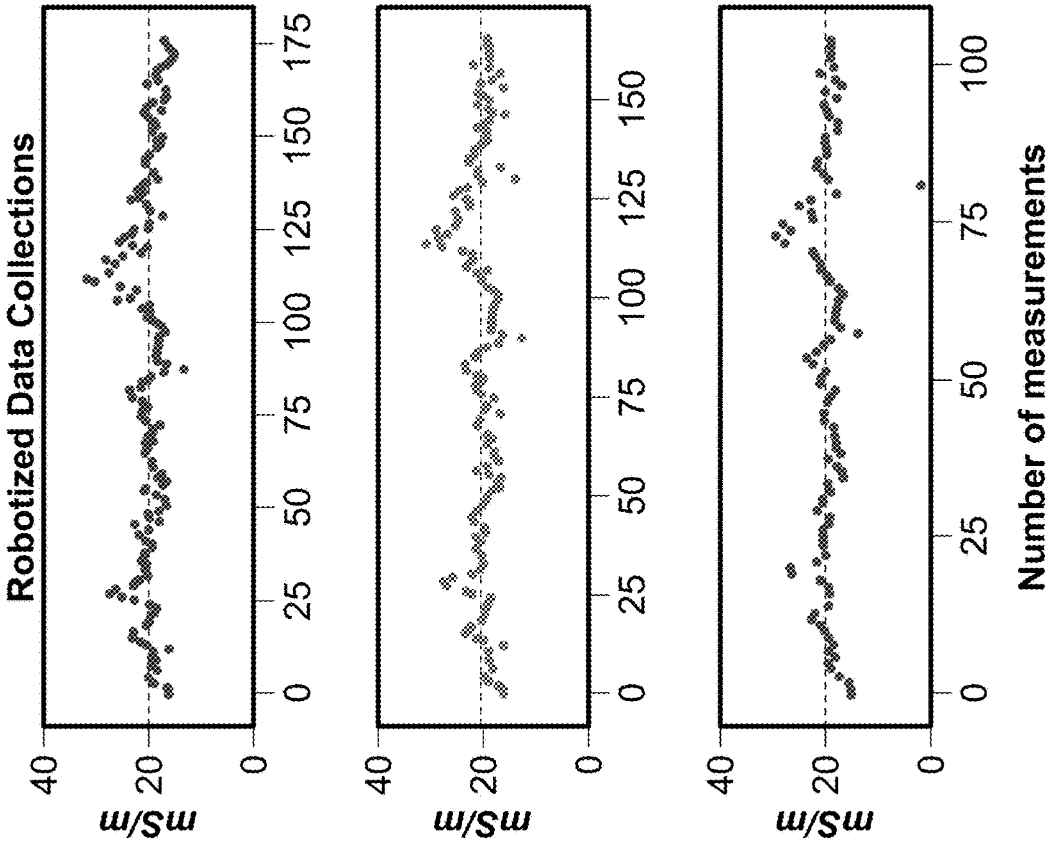
Figure 25C:
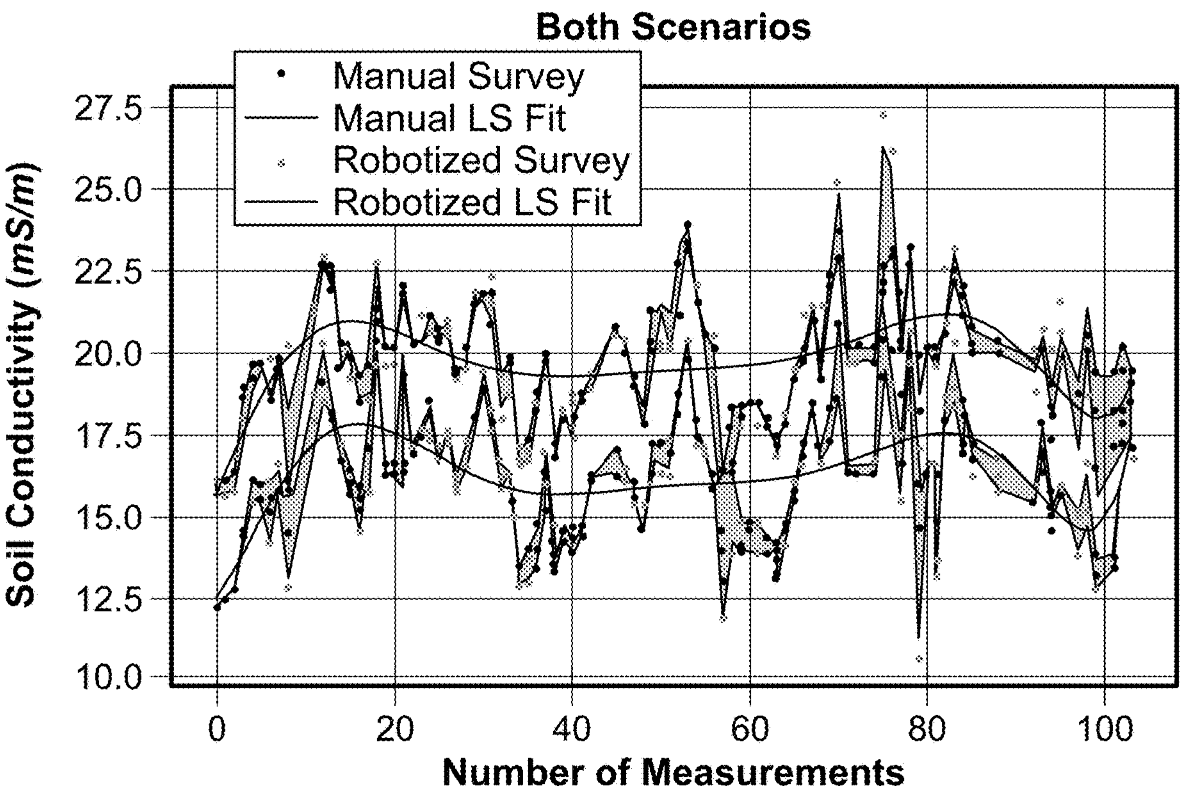

Experimental Procedure: Continuous soil ECa measurements were performed in two distinctive fields, an olive tree grove (not irrigated recently with respect to data collections) and a citrus tree grove (irrigated prior to data collections). The arid canopy of olive trees is located close to the USDA-ARS U.S. Salinity Laboratory at the University of California, Riverside (UCR) (33 58'21.936" N, −117 19'13.5732" E), whereas the freshly irrigated citrus orchard is located within the UCR Agricultural Experimental Station fields (AES; 33 57'52.0272" N, −117 20'13.7184" E). It is worth noting that the latter case in fact contained various soil conditions (highly irrigated/wet parts and arid parts), and hence helped evaluate 1) the proposed robot's performance in the same survey as terrain conditions vary, and 2) if the robot-assisted soil conductivity curves and soil ECa maps match those corresponding to manual data collections. Experimental setups and snapshots of the two fields are depicted in FIG. 22. For the olive tree grove an area of two full tree rows covered following a U-shaped trajectory was considered, whereas for the citrus tree grove an area of roughly three tree rows covered following an S-shaped trajectory was considered. Manual data collections with the handheld sensor (three in each field) were also performed to serve as the baseline. In total, 12 experimental trials were conducted for overall system field-scale evaluation in the olive and citrus tree groves (six robotized and six manual). Obtained soil ECa measurements were georeferenced via RTK-GNSS in the robotized measurement and the sensor's embedded GPS in the manual measurements. Collected soil ECa data were used to generate a custom raster of the surveyed area; then kriging interpolation through exponential semivariogram helped obtain the ECa map which was embedded onto satellite imagery via the ESRI ArcGIS 10.8.2 software.

Key Findings: Results from field-scale experiments for olive and citrus tree groves are shown in FIG. 23-26. Collected raw data from each considered case, aggregated soil conductivity data comparing robotized to manual baselines, as well as the corresponding ECa maps are presented. It can be readily verified from the graphs that robot-assisted continuous ECa measurements approximate very well the manually-collected baselines in both cases.

For the case of the olive tree grove (arid field) raw measurement plots (FIG. 23A and FIG. 23B) match either very well. The visual observation is corroborated via the mean measurement plots (FIG. 23C), where PCC reaches a score of 0.97. The mean conductivity value in the robotized case is 14.23 mS/m, compared to the 10.56 mS/m mean value of the manual case, which represents a fixed increase which can be seen by the curvature of the polynomial fits. Additionally, the standard deviations are closely matching robotized: 1.65 mS/m; manual: 1.75 mS/m) which demonstrates consistency across both soil ECa measurement means. Closely matching in some embodiments is less than about 5%. Closely matching in some embodiments is less than about 10%. closely matching in some embodiments is less than about 15%. Output ECa maps (FIG. 24) are also very similar, with a PCC value of 0.97 in a pixel-wise correlation. It is notably clear that the robotized results are close to the manual ones, in spite of the constant positive offset on the level of the measured soil apparent electrical conductivity.

Figure 26A:
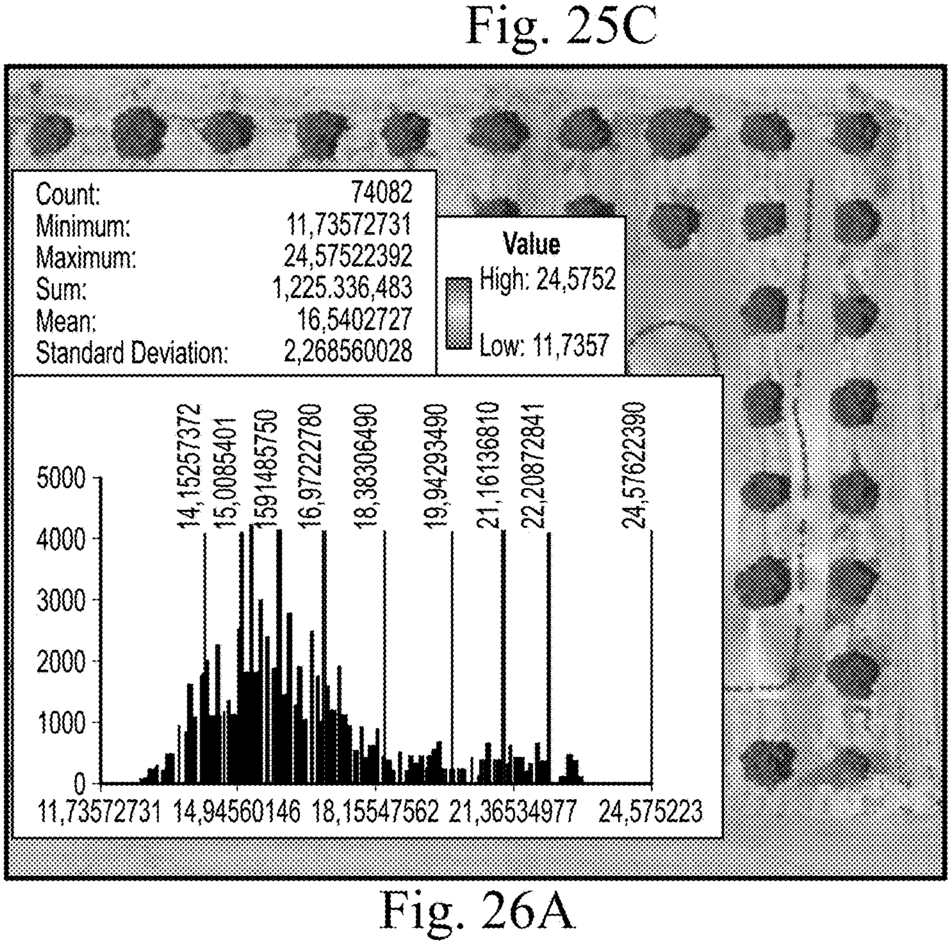
FIG. 26A and FIG. 26B: Obtained soil ECa maps in the citrus tree grove for (A) the manual and (B) robotized cases. Maps were created by applying kriging interpolation through exponential semivariogram. Each map also depicts the value-based color scale, the map statistics, and the histogram of the conductivity values.
Figure 26B:
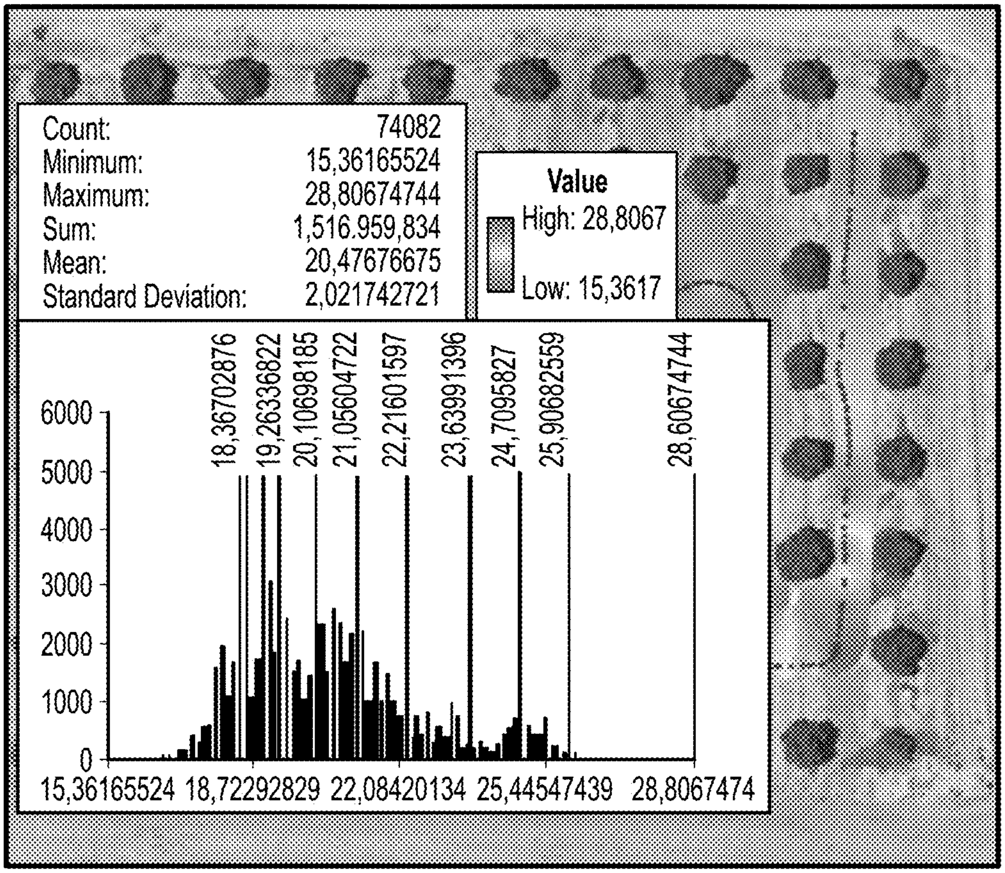

Similar observations can be readily made for the case of the citrus tree grove. Note that the citrus tree grove was recently irrigated prior to data collection, hence there was more terrain variability; this ranged from muddy soil to normally irrigated areas and more dry parts of the field areas. From a robot operation standpoint, the robot system demonstrates robust behavior even in this diverse and more demanding survey case, and it is noteworthy that the robot's traversability in the irrigated turf was efficient even when navigating over mud. Raw data graphs (FIG. 25A and FIG. 25B) demonstrate several notable peaks in soil conductivity measurements that were caused when traversability in the muddy terrain and the well-irrigated soil. These peaks were captured in both manual and robot-assisted surveys. The graphs shown in FIG. 25C have a PCC 0.90, which demonstrates the robot's robustness in even muddy and quite diverse soil-ECa-level fields. The polynomial fits of both plots (FIG. 25C) present similar curvature with an additive offset increase in the robot's case, caused by the electromagnetic interference, whereas the pixel-wise correlation of the output ECa maps reaches a value of 0.96 (FIG. 26).

Visual inspection of the obtained soil ECa maps also supports the aforementioned findings.

The disclosure described embodiments of a robotized system to perform precise and continuous soil apparent electrical conductivity (ECa) measurement surveys. The methods and apparatus described includes a ground mobile robot equipped with a customized and adjustable platform to hold an Electromagnetic Induction (EMI) sensor. The substantially optimal placement of the EMI sensor is determined by satisfying two competing objectives; the minimization of static electromagnetic interference in measurements and the facilitation of robot traversability in the field. Extensive experimental evaluation across static calibration tests and over different types of fields concludes to the optimal EMI configuration setup to be used for large-field testing. Throughout a series of real field experiments, it is demonstrated that that the obtained robot-assisted, soil conductivity measurements present high linearity compared to the ground truth (data collected manually by a handheld EMI sensor) by scoring more than 90% in Pearson correlation coefficient in both plot measurements and estimated ECa maps generated by kriging interpolation. The proposed platform can deliver high-linearity scores in real survey scenarios, at an olive and citrus grove under different irrigation levels, and serve as a robust tool for large-scale ECa mapping in the field, with the potential development of a fully-autonomous behavior. Further embodiments can include integration within a task and motion framework for informative proximal sampling, as well as integration with physical sampling means to perform multiple tasks simultaneously.

Figure 27:
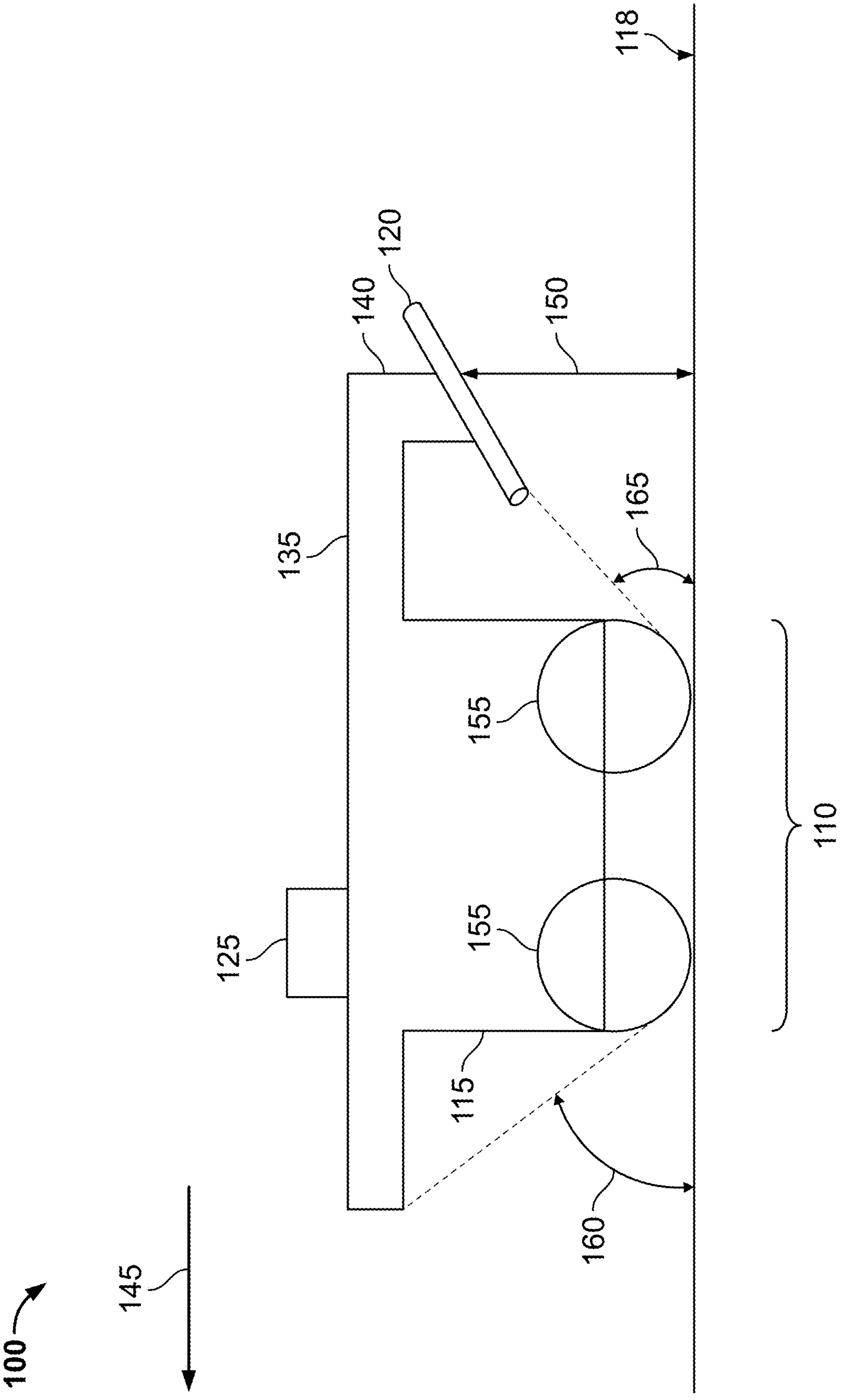
FIG. 27 shows a block diagram of an apparatus including a mobile platform, a sensor, and a control system in accordance with some embodiments of the present disclosure.

FIG. 27 shows a block diagram of an apparatus 100 including a mobile platform 110, a sensor 120, and a control system 125 in accordance with some embodiments of the present disclosure. In some embodiments, the mobile platform is a robot, such as the robots described throughout the disclosure. The mobile platform 110 including a chassis 115. In operation, the mobile platform 100 traverses an agricultural field 118. Example agricultural fields include citrus fields and olive fields. The sensor 120 is physically couped to the mobile platform 110. I operation, the sensor 120 makes one or more soil apparent electrical conductivity measurements in the agricultural field 118. The control system 125 is mounted on the chassis 115 and communicatively coupled to the sensor 120. In some embodiments, the control system 125 is communicatively coupled to the sensor 120 through a wireless connection. In some embodiments, the control system 125 is hardwired to the sensor 120. In some embodiments, the control system 125 is a control system, such as the control systems described above.

In some embodiments, the mobile platform 110 has an optimal chassis to sensor distance 130 that is optimum for avoiding electrical interference between the sensor 120 and the chassis 115. In operation the sensor 120 is positioned at an operational distance from the chassis that is less than the optimal chassis to sensor distance 130. The control system 125 provides geo-referencing and autonomous logging of the one or more soil apparent electrical conductivity measurements.

The mobile platform 110 includes an adjustable platform 135 to hold the sensor 120. In some embodiments, the sensor 120 is physically coupled to the mobile platform 110 by non-conductive rods, such as carbon-fiber rods 140. In some embodiments, the mobile platform 110 has a direction of travel 145 and the sensor 120 is oriented substantially perpendicular to the direction of travel 145.

The apparatus 100 includes a ground clearance distance 150 that defines an operational distance between the sensor 120 and the agricultural field 118. In some embodiments, the ground clearance distance 150 is between about forty-five and fifty-five millimeters. In some embodiments, the ground clearance distance 150 is between thirty-five and sixty-five millimeters. In some embodiments, the ground clearance distance 150 is between twenty-five and seventy-five millimeters. The mobile platform 110 includes wheels 155 to contact the agricultural field 118. In some embodiments, the sensor 120 is tuned such that the one or more soil apparent electrical conductivity measurements have high-accuracy to a soil depth of about 0.7 meters. High-accuracy, as used herein, means the measurements that are within 5% of the equivalent manual measurement.

In some applications, the agricultural field 118 includes terrain deviations and in some embodiments, the mobile platform 110 includes an approach angle α 160 and a departure angle β 165 selected to enable the mobile platform 110 to traverse the agricultural field 118 and make useful measurements. In some applications, the agricultural field 118 includes micro-irrigated orchard systems and the terrain deviations are about twenty-five millimeters or less.

Figure 28:
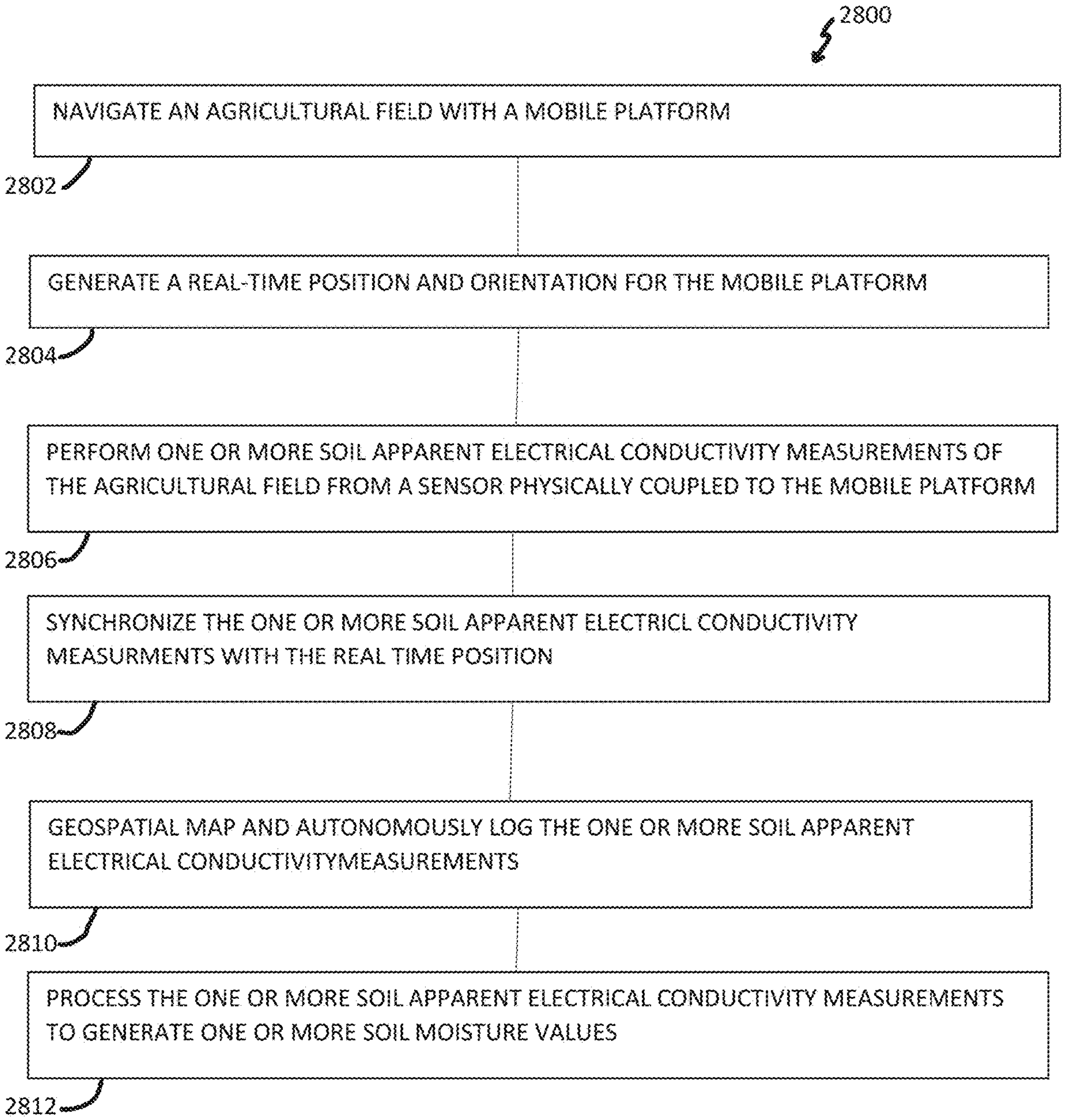
FIG. 28 shows a flow diagram of a method in accordance with some embodiments of the present disclosure.

FIG. 28 shows a flow diagram of a method 2800 in accordance with some embodiments of the present disclosure. The method 2800 includes navigating an agricultural field with a mobile platform (block 2802); generating a real-time position and orientation for the mobile platform (block 2804); performing one or more soil apparent electrical conductivity measurements of the agricultural field from a sensor physically coupled to the mobile platform (block 2806); synchronizing the one or more soil apparent electrical conductivity measurements with the real-time position (2808); geospatial mapping and autonomously logging the one or more soil apparent electrical conductivity measurements (2810); and processing the one or more soil apparent electrical conductivity measurements to generate one or more soil moisture values (2812).

In some embodiments, navigating the agricultural field with the mobile platform includes traversing a root zone under tree canopies of an olive grove. In some embodiments, navigating the agricultural field with the mobile platform includes navigating a muddy agricultural field. In some embodiments, the method further includes delivering high-linearity scores in real survey scenarios at a citrus grove under different irrigation levels by scoring more than about 90% in Pearson correlation coefficient in both plot measurements and estimated apparent electrical conductivity maps generated by kriging interpolation. In some embodiments, the method further includes utilizing a simulation software package that provides estimation of terrain traversability in relation to identifying substantially optimal sensor placement. In some embodiments, navigating the agricultural field with the mobile platform includes generating platform control commands from a waypoint-based trajectory planner. In some embodiments, navigating the agricultural field with the mobile platform includes navigating along one or more drip lines in the agricultural field. In some embodiments, the method further includes scheduling irrigation for the agricultural field based on the soil moisture values. In some embodiments, processing the one or more soil apparent electrical conductivity measurements to generate the one or more soil moisture values comprises including a correction factor in the processing to account for the mobile platform influencing the one or more soil apparent electrical conductivity measurements. In some embodiments, the method further includes displaying the soil moisture value in real time. In some embodiments, the method further includes determining the maximum practical sensor mounting distance dh and angles α and β that allow the robot to traverse uneven terrain with deviations of plus or minus about 25 millimeters from level after mounting the sensor on the mobile robot without tipping, stalling, or colliding the sensor into the ground.

Figure 29:
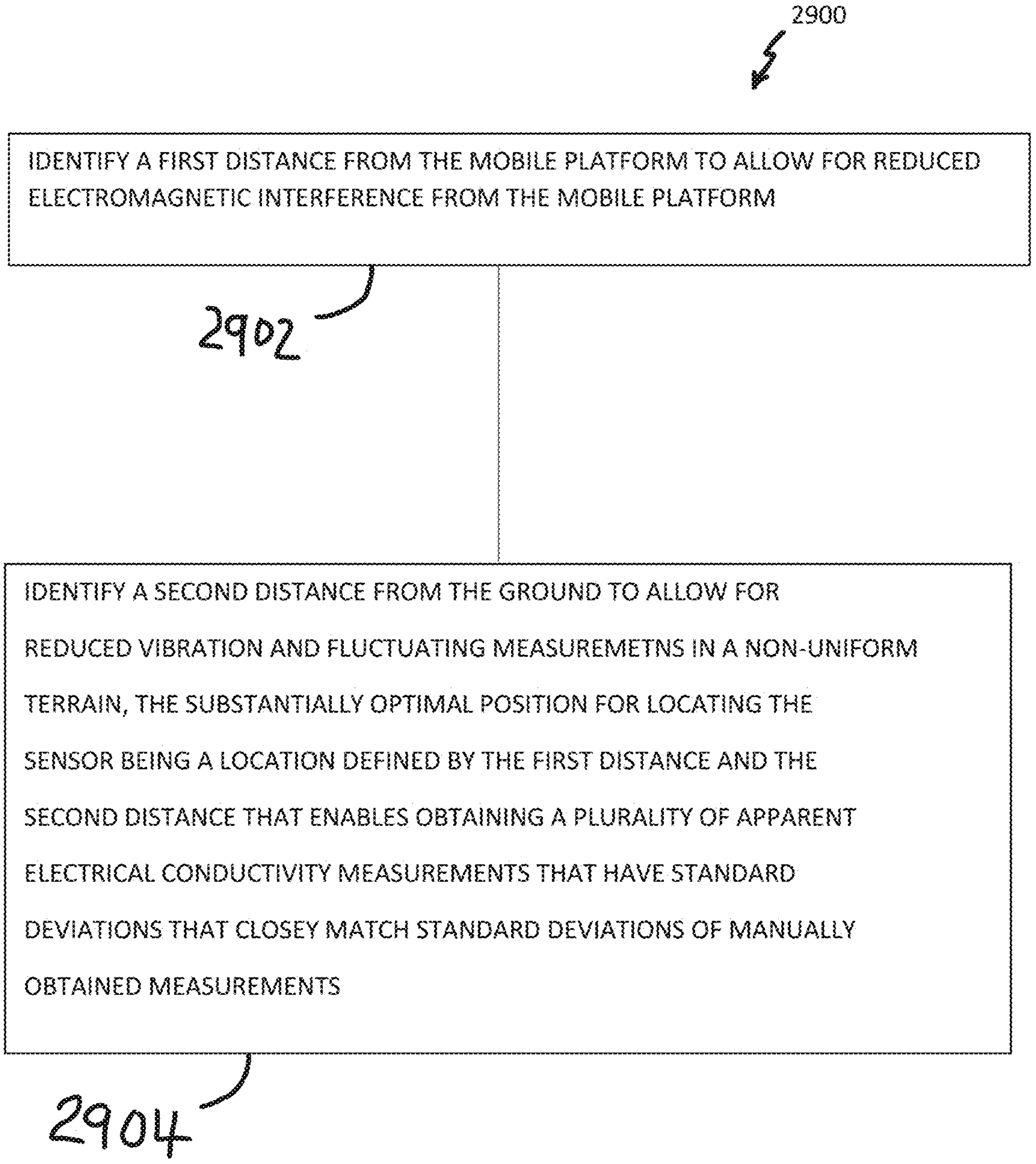
FIG. 29 shows a flow diagram of a method for identifying a substantially optimal position for positioning a sensor on a mobile platform in accordance with some embodiments of the present disclosure.

FIG. 29 shows a flow diagram of a method 2900 for identifying a substantially optimal position for positioning a sensor on a mobile platform, the method in accordance with some embodiments of the present disclosure. The method 2900 includes identifying a first distance from the mobile platform to allow for reduced electromagnetic interference from the mobile platform (block 2902); and identifying a second distance from the ground to allow for reduced vibration and fluctuating measurements in a non-uniform terrain, the substantially optimal position for locating the sensor being a location defined by the first distance and the second distance that enables obtaining a plurality of apparent electrical conductivity measurements that have standard deviations that closely match standard deviations of manually obtained measurements (block 2904). In some embodiments, identifying the first distance from the mobile platform to allow for reduced electromagnetic interference from the robot includes identifying a distance of about sixty centimeters. In some embodiments, identifying a second distance from the ground to allow for reduced vibration and fluctuating measurements in a non-uniform terrain comprises selecting a height of about six centimeters. In some embodiments, identifying a first distance from the mobile platform to allow for reduced electromagnetic interference from the robot includes identifying a distance of about sixty centimeters. In some embodiments, identifying a second distance from the ground to allow for reduced vibration and fluctuating measurements in a non-uniform terrain includes selecting a height of about six centimeters.

All publications, patents, and patent documents are incorporated by reference herein, as though individually incorporated by reference. Reference throughout this specification to "an embodiment," "some embodiments," or "one embodiment." means that a particular feature, structure, material, or characteristic described in connection with the embodiment is included in at least one embodiment of the present disclosure. Thus, the appearances of the phrases such as "in some embodiments," "in one embodiment," or "in an embodiment," in various places throughout this specification are not necessarily referring to the same embodiment of the present disclosure. Furthermore, the particular features, structures, materials, or characteristics may be combined in any suitable manner in one or more embodiments. Reference numbers are Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. An apparatus comprising:

a mobile platform including a chassis, the mobile platform to traverse an agricultural field;

a sensor physically coupled to the mobile platform, the sensor to make one or more soil apparent electrical conductivity measurements in the agricultural field; and a control system mounted on the chassis and communicatively coupled to the sensor, wherein the apparatus includes a ground clearance distance that defines an operational distance between the sensor and the agricultural field of between about forty-five and fifty-five millimeters.

2. The apparatus of claim 1, wherein the mobile platform has an optimal chassis to sensor distance that is optimum for avoiding electrical interference between the sensor and the chassis, the sensor positioned at an operational distance from the chassis that is less than the optimal chassis to sensor distance.

3. The apparatus of claim 2, wherein the control system provides geo-referencing and autonomous logging of the one or more soil apparent electrical conductivity measurements.

4. The apparatus of claim 1, wherein the mobile platform includes an adjustable platform to hold the sensor.

5. The apparatus of claim 4, wherein the mobile platform has a direction of travel, the sensor is oriented substantially perpendicular to the direction of travel.

6. The apparatus of claim 1, wherein the agricultural field includes terrain deviations and the mobile platform includes an approach angle α and a departure angle β selected to enable the mobile platform to traverse the agricultural field and make useful measurements.

7. The apparatus of claim 6, wherein the terrain deviations are about twenty-five millimeters or less.

8. A method comprising:

navigating an agricultural field with a mobile platform;

generating a real-time position and orientation for the mobile platform;

performing one or more soil apparent electrical conductivity measurements of the agricultural field from a sensor physically coupled to the mobile platform;

synchronizing the one or more soil apparent electrical conductivity measurements with the real-time position;

geospatial mapping and autonomously logging the one or more soil apparent electrical conductivity measurements; and processing the one or more soil apparent electrical conductivity measurements to generate one or more soil moisture values.

9. The method of claim 8, wherein navigating the agricultural field with the mobile platform comprises traversing a root zone under tree canopies of an olive grove.

10. The method of claim 8, further comprising delivering high-linearity scores in real survey scenarios at a citrus grove under different irrigation levels by scoring more than 90% in Pearson correlation coefficient in both plot measurements and estimated apparent electrical conductivity maps generated by kriging interpolation.

11. The method of claim 8, wherein navigating the agricultural field with the mobile platform comprises navigating along one or more drip lines in the agricultural field.

12. The method of claim 8, wherein processing the one or more soil apparent electrical conductivity measurements to generate the one or more soil moisture values comprises including a correction factor in the processing to account for the mobile platform influencing the one or more soil apparent electrical conductivity measurements.

13. A method of claim 8, further comprising determining the maximum practical sensor mounting distance $d_h$ and angles α and β that allow the robot to traverse uneven terrain with deviations of plus or minus 25 millimeters from level after mounting the sensor on the mobile robot without tipping, stalling, or colliding the sensor into the ground.

14. The method of claim 8, further comprising displaying the one or more soil moisture values in real time.

* * * * *